US011492626B2

(12) United States Patent
Van Eck Conradie et al.

(10) Patent No.: US 11,492,626 B2
(45) Date of Patent: Nov. 8, 2022

(54) MATERIALS AND METHODS FOR THE BIOSYNTHESIS OF SEVEN CARBON CHEMICALS IN THE PRESENCE OF METHANOL OXIDATION

(71) Applicant: INV Nylon Chemicals Americas, LLC, Wilmington, DE (US)

(72) Inventors: Alex Van Eck Conradie, Eaglescliffe (GB); Achuthanunni Chokkathukalam, Marske by the Sea (GB); Remi Ako Mbianyor Momo, Wilmington, DE (US)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 22 days.

(21) Appl. No.: 16/947,598

(22) Filed: Aug. 7, 2020

(65) Prior Publication Data

US 2021/0032632 A1 Feb. 4, 2021

Related U.S. Application Data

(63) Continuation of application No. 15/659,521, filed on Jul. 25, 2017, now abandoned.

(60) Provisional application No. 62/366,549, filed on Jul. 25, 2016.

(51) Int. Cl.
| | |
|---|---|
| *C12N 15/52* | (2006.01) |
| *C12P 7/42* | (2006.01) |
| *C12P 7/18* | (2006.01) |
| *C12P 13/00* | (2006.01) |
| *C12P 7/44* | (2006.01) |
| *C12P 7/40* | (2006.01) |
| *C08G 69/08* | (2006.01) |
| *C12N 9/04* | (2006.01) |
| *C12N 9/16* | (2006.01) |
| *C12N 9/00* | (2006.01) |

(52) U.S. Cl.
CPC .............. *C12N 15/52* (2013.01); *C08G 69/08* (2013.01); *C12N 9/0006* (2013.01); *C12N 9/16* (2013.01); *C12N 9/93* (2013.01); *C12P 7/18* (2013.01); *C12P 7/40* (2013.01); *C12P 7/42* (2013.01); *C12P 7/44* (2013.01); *C12P 13/00* (2013.01); *C12P 13/005* (2013.01); *C12Y 101/01001* (2013.01); *C12Y 101/01284* (2013.01); *C12Y 301/02012* (2013.01); *C12Y 603/04003* (2013.01)

(58) Field of Classification Search
CPC ...... C08G 69/08; C12N 15/52; C12N 9/0006; C12N 9/16; C12N 9/93; C12P 7/18; C12P 7/40; C12P 7/42; C12P 7/44; C12P 13/00; C12P 13/005; C12Y 101/01001; C12Y 101/01284; C12Y 301/02012; C12Y 603/04003
See application file for complete search history.

(56) References Cited

U.S. PATENT DOCUMENTS

| | | |
|---|---|---|
| 2014/0186904 A1 | 7/2014 | Botes et al. |
| 2014/0242655 A1 | 8/2014 | Pearlman et al. |

FOREIGN PATENT DOCUMENTS

| | | |
|---|---|---|
| WO | WO 2014/105793 A1 | 7/2014 |
| WO | WO 2014/105794 A2 | 7/2014 |
| WO | WO 2018/022613 A1 | 2/2018 |

OTHER PUBLICATIONS

Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Altschul et al. "Gapped Blast and PSI-Blast: A New Generation of Protein Database Search Programs", Nucleic Acids Research (NCIB NLM NIH), Bethesda Md., NAR, vol. 25, No. 17, Jul. 16, 1997, pp. 3389-3402.
Anton et al. "Polyamides, Fibers", Encyclopedia of Polymer Science and Technology, vol. 3, Oct. 22, 2001, pp. 584-612.
Ausubel et al., "Current Protocols in Molecular Biology", Greene Publishing Associates/Wiley Interscience, New York, Supplement 30, section 7.7.18, 1987, 1 page.
Barker et al, "Enzymatic Reactions in the Degradation of 5-Aminovalerate by Clostridium Aminovalericum", The Journal of Biological Chemistry, vol. 262, No. 19, Jul. 5, 1987, pp. 8994-9003.
Bar-Even, A., "Formate Assimilation: The Metabolic Architecture of Natural and Synthetic Pathways", Biochemistry, vol. 55, No. 28, Jun. 27, 2016, pp. 3851-3863. {Abstract}.
Becker et al, "Metabolic Flux Engineering of l-Lysine Production in Corynebacteriurn Glutamicum-Over Expression and Modification of G6P Dehydrogenase", Journal of Biotechnology, vol. 132, Oct. 31, 2007, pp. 99-109.

(Continued)

*Primary Examiner* — Iqbal H Chowdhury

(57) ABSTRACT

This disclosure describes methods for regulating the biosynthesis of pimelic acid, 7-aminoheptanoate, 7-hydroxyheptanoate, heptamethylenediamine, 7-aminoheptanol, or 1,7-heptanediol by channeling increased flux through the biosynthesis pathway to obtain an intermediate required for growth of the host microorganism.

11 Claims, 15 Drawing Sheets
Specification includes a Sequence Listing.

(56) References Cited

OTHER PUBLICATIONS

Bellmann et al., "Expression Control and Specificity of the Basic Amino Acid Exporter LysE of Corynebacterium Glutamicum", Microbiology, vol. 147, Jul. 1, 2001, pp. 1765-1774.
Bond-Watts et al., "Biochemical and Structural Characterization of the Trans-Enoyl-CoA Reductase from Treponema Denticola", Biochemistry, vol. 51, No. 34, 2012, pp. 6827-6837.
Brigham et al., "Engineering Ralstonia Eutropha for Production of Isobutanol from C02, H2, and O2", Advanced Biofuels and Bioproducts, Chapter 39, Jan. 2013, pp. 1065-1090.
Buchenau et al., "Tetrahydrofolate-Specific Enzymes in Methanosarcina Barkeri and Growth Dependence of this Methanogenic Archaeon on Folic Acid or P-Aminobenzoic Acid", Archives of Microbiology, vol. 182, Issue 4, Oct. 2004, pp. 313-325.
Buckel et al., "Glutaconate CoA-Transferase from Acidaminococcus Fermentans", European Journal of Biochemistry, vol. 118, 1981, pp. 315-321.
Budde et al., "Roles of Multiple Acetoacetyl Coenzyme A Reductases in Polyhydroxybutyrate Biosynthesis in Ralstonia Eutropha H16", Journal of Bacteriology, vol. 192, No. 20, Oct. 2010, pp. 5319-5328.
Bugg et al., "The Emerging Role for Bacteria in Lignin Degradation and Bio-Product Formation", Current Opinion in Biotechnology, vol. 22, 2011, pp. 394-400.
Bult et al., "Complete Genome Sequence of the Methanogenic Archaeon, Methanococcus Jannaschii", Science, ProQuest Technology Collection, vol. 273, No. 5278, Aug. 23, 1996, pp. 1058-1073.
Cantu et al., "Thioesterases: A New Perspective Based on Their Primary and Tertiary Structures", Protein Science, vol. 19, May 17, 2010, pp. 1281-1295.
Demain et al., "Manual of Industrial Microbiology and Biotechnology", 2nd Edition, Scale-Up of Microbial Processes, ASM Press, 1999, 5 pages.
Dziewit et al., "Genome-guided insight into the methylotrophy of Paracoccus aminophilus JCM 7686", vol. 6, 2015, pp. 1-13.
Elkins et al., "Substrate Specificity of the RND-Type Multidrug Efflux Pumps AcrB and AcrD of *Escherichia coli* Is Determined Predominately by Two Large Periplasmic Loops", Journal of Bacteriology, vol. 184, No. 23, Dec. 2002, pp. 6490-6498.
Fukui et al., "Expression and Characterization of (R)-Specific Enoyl Coenzyme A Hydratase Involved in Polyhydroxyalkanoate Biosynthesis by Aeromonas Caviae", Journal of Bacteriology, vol. 180, No. 3, Feb. 1998, pp. 667-673.
Genbank, "Acyl-[Acyl-Carrier Protein] Thioesterase [Lactobacillus Plantarum WCFS1 ]", Accession No. CCC78182.1, Feb. 27, 2015, 1 page.
Genbank, "Acyl-ACP Thioesterase [Lactobacillus Brevis ATCC 367]", Accession No. ABJ63754.1, Jan. 28, 2014, 2 pages.
Genbank, "Adenosylmethionine-8-Amino-7-Oxononanoate Aminotransferase [Rhodobacter Sphaeroides 2.4.1 ]", Accession No. ABA81135.1, Jul. 20, 2015, 2 pages.
Genbank, "Alcohol Dehydrogenase [Geobacillus Stearothermophilus]", Accession No. CAA81612.1, Apr. 18, 2005, 2 pages.
Genbank, "Aminotransferase Class-III [Pseudomonas Syringae Pv. Syringae B728a]", Accession No. AAY39893.1, Jan. 31, 2014, 2 pages.
Genbank, "Biotin Synthesis Protein BioC, Putative [Bacillus Cereus ATCC 10987]", Accession No. AAS43086.1, Jan. 31, 2014, 1 page.
Genbank, "Fatty-Acid-CoA Ligase FadD9 [*Mycobacterium marinum* M]", Accession No. ACC40567.1, Jan. 31, 2014, 2 pages.
Genbank, "NAO Dependent Epimerase/Dehydratase Family Protein [*Mycobacterium smegmatis* Str. MC2 155]", Accession No. ABK75684.1, Jan. 31, 2014, 2 pages.
Genbank, "ORF_o387 [*Escherichia coli* Str. K-12 Substr. MG1655]", Accession No. AAA69178.1, Jul. 1, 1995, 1 page.
Genbank, "Phosphopantetheinyl Transferase [Nocardia lowensis]", Accession No. ABI83656.1, Jan. 3, 2007, 1 page.
Genbank, "Pimeloyl-ACP Methyl Ester Carboxylesterase [*Escherichia coli* Str. K-12 Substr. MG1655]", Accession No. AAC76437.1, Aug. 1, 2014, 3 pages.
Genbank, "Probable Aminotransferase [Chromobacterium Violaceum ATCC 12472]", Accession No. AAQ59697.1, Jan. 31, 2014, 2 pages.
Genbank, "Probable Class III Aminotransferase [Pseudomonas Aeruginosa PA01 ]", Accession No. AAG08191.1, Jan. 31, 2014, 2 pages.
Genbank, "Putative Fatty-Acid-CoA Ligase FADD9 [*Mycobacterium abscessus* Subsp. *Bolletii* 2B-0307]", Accession No. EIV11143.1, Dec. 19, 2014, 2 pages.
Genbank, "Putative Long-Chain Fatty-Acid-CoA Ligase [*Mycobacterium smegmatis* Str. MC2 155]", Accession No. ABK71854 1, Jan. 31, 2014, 2 pages.
Genbank, "Pyruvate Transaminase [Vibrio Fluvialis]", Accession No. AEA39183.1, Apr. 4, 2011, 1 page.
Genbank, "Thioester Reductase Domain Protein [Segniliparus Rotundus DSM 44985]", Accession No. ADG98140.1, Jan. 28, 2014, 2 pages.
Genbank, "Thioester Reductase Domain-Containing Protein [Segniliparus Rugosus ATCC BAA-974]", Accession No. EFV11917. 1, Sep. 9, 2013, 3 pages.
Genbank, "Thioesterase II [*Escherichia coli*]", Accession No. AAA24665.1, Apr. 26, 1993, 1 page.
Genbank, "Unknown [*Saccharomyces cerevisiae*]", Accession No. CAA90836.1, Jul. 14, 2016, 2 pages.
Gloerich et al., "Peroxisomal Trans-2-Enoyl-CoA Reductase is Involved in Phytol Degradation", FEBS Letters, vol. 580, Mar. 10, 2006, pp. 2092-2096.
Guerrillot et al., "Purification and Characterization of Two Aldehyde Dehydrogenases from Pseudomonas Aeruginosa", European Journal of Biochemistry, vol. 81, Nov. 1977, pp. 185-192.
Harwood et al., "The Beta-Ketoadipate Pathway and the Biology of Self-Identity", Annual Review of Microbiology, vol. 50, Oct. 1996, pp. 553-590.
Haywood et al., "Characterization of Two 3-Ketothiolases Possessing Differing Substrate Specificities in the Polyhydroxyalkanoate Synthesizing Organism Alcaligenes Eutrophus", FEMS Microbiology Letters, vol. 52, Jul. 1988, pp. 91-96.
Hermann, Thomas, "Industrial Production of Amino Acids by Coryneform Bacteria", Journal of Biotechnology, vol. 104,2003, pp. 155-172.
Huhn et al., "Identification of the Membrane Protein SucE and its Role in Succinate Transport in Corynebacterium Glutamicum", Applied Microbiology and Biotechnology, vol. 89, Jan. 2011, pp. 327-335.
Iwaki et al., "Cloning and Characterization of a Gene Cluster Involved in Cyclopentanol Metabolism in *Comamonas* Sp. Strain NCIMB 9872 and Biotransformations Effected by *Escherichia coli*-Expressed Cyclopentanone 1,2-Monooxygenase", Applied and Environmental Microbiology, vol. 68, No. 11, Nov. 2002, pp. 5671-5684.
Iwaki et al., "Identification of a Transcriptional Activator (ChnR) and a 6-Oxohexanoate Dehydrogenase (ChnE) in the Cyclohexanol Catabolic Pathway in *Acinetobacter* Sp. Strain NCIMB 9871 and Localization of the Genes That Encode Them", Applied and Environmental Microbiology, vol. 65, No. 11, Nov. 1999, pp. 5158-5162.
Jarboe, Laura R., "YqhD A Broad-Substrate Range Aldehyde Reductase with Various Applications in Production of Biorenewable Fuels and Chemicals", Appl. Microbiol. Biotechnol., vol. 89, No. 2, 2011, pp. 249-257.
Jaremko et al., "The Initial Metabolic Conversion of Levulinic Acid in Cupriavidus Necator", Journal of Biotechnology, vol. 155, 2011, pp. 293-298.
Jing et al., "Phylogenetic and Experimental Characterization of an Acyl-ACP Thioesterase Family Reveals Significant Diversity in Enzymatic Specificity and Activity", BMC Biochemistry, vol. 12, No. 44, 2011, 16 pages.
Kaulmann et al., "Substrate Spectrum of ω-Transaminase from Chromobacterium Violaceum DSM30191 and its Potential for Biocatalysis", Enzyme and Microbial Technology, vol. 41, Oct. 2007, pp. 628-637.
Kim, Ki-Han, "Purification and Properties of a Mine α-Ketoglutarate Transaminase from *Escherichia coli*", The Journal of Biological Chemistry, vol. 239, No. 3, Mar. 1, 1964, pp. 783-786.

(56) References Cited

OTHER PUBLICATIONS

Kopke et al., "2,3-Butanediol Production by Acetogenic Bacteria, an Alternative Route to Chemical Synthesis, Using Industrial Waste Gas", Applied and Environmental Microbiology, vol. 77, No. 15, Aug. 2011, pp. 5467-5475.
Lan et al., "Oxygen-Tolerant Coenzyme A-Acylating Aldehyde Dehydrogenase Facilitates Efficient Photosynthetic N-Butanol Biosynthesis in Cyanobacteria", Energy & Environmental Science, vol. 6, 2013, pp. 2672-2681.
Larroy et al., "Characterization of the *Saccharomyces cerevisiae* YMR318C (ADH6) Gene Product as a Broad Specificity NADPH-Dependent Alcohol Dehydrogenase: Relevance in Aldehyde Reduction", Biochem Journal, vol. 361, No. 1, Jan. 1, 2002, pp. 163-172.
Lee et al., "Metabolic Engineering of Pentose Phosphate Pathway in Ralstonia Eutropha for Enhanced Biosynthesis of Poly-β-Hydroxybutyrate", Biotechnology Progress, vol. 19, Issue 5, 2003, pp. 1444-1449.
Lee et al., "Synthesis of Pure Meso-2,3-Butanediol from Crude Glycerol Using an Engineered Metabolic Pathway in *Escherichia coli*", Applied Biochemistry and Biotechnology, vol. 166, No. 7, 2012, pp. 1801-1813.
Li et al., "Cupriavidus Necator JMP134 Rapidly Reduces Furfural with a Zn-Dependent Alcohol Dehydrogenase", Biodegradation, vol. 22, No. 6, 2011, pp. 1215-1225.
Lim et al., "Amplification of the NADPH-Related Genes zwf and gnd for the Oddball Biosynthesis of PHB in an *E. coli* Transformant Harboring a Cloned phbCAB Operon", Journal of Bioscience and Bioengineering, vol. 93, No. 6, 2002, pp. 543-549.
Lin, Steven, "Biotin Synthesis in *Escherichia coli*", University of Illinois at Urbana-Champaign, 2012, 140 pages.
Liu et al., "Production and Characterization of Medium-Chain-Length Polyhydroxyalkanoate with High 3-Hydroxytetradecanoate Monomer Content by fadB and fadA Knockout Mutant of Pseudomonas Putida KT2442", Applied Microbiology and Biotechnology, vol. 76, No. 5, Aug. 1, 2007, pp. 1153-1159.
Liu et al., "Two Novel Metal-independent Long-Chain Alkyl Alcohol Dehydrogenases From Geobacilius Thermodenitrificans NG80-2", Microbiology, vol. 155, No. 6, Mar. 3, 2009, pp. 2078-2085.
Lopez-Sanchez et al., "Tetralin-Induced and ThnR-Regulated Aldehyde Dehydrogenase and β-Oxidation Genes in Sphingomonas Macrogolitabida Strain TFA", Applied Environmental Microbiology, vol. 76, No. 1, Jan. 2010, pp. 110-118.
Maeder et al., "The Methanosarcina Barkeri Genome Comparative Analysis with Methanosarcina Acetivorans and Methanosarcina Mazei Reveals Extensive Rearrangement within Methanosarcinal Genomes", Journal of Bacteriology, vol. 188, No. 22, Nov. 2006, pp. 7922-7931.
Martin et al., "High-Titer Production of Monomeric Hydroxyvalerates from Levulinic Acid in Pseudomonas Putida", Journal of Biotechnology, vol. 139, No. 1, 2009, pp. 61-67.
Meijnen et al., "Improved p. Hydroxybenzoate Production by Engineered Pseudomonas Putida S12 by Using a Mixed-substrate Feeding Strategy", Applied Microbiology and Biotechnology, vol. 90, No. 3, 2011, pp. 885-893.
Muller et al., "Methylotrophy in the thermophilic Bacillus methanolicus, basic insights and application for commodity production from methanol", Applied Microbiology and Biotechnology, vol. 99, No. 2, 2015, pp. 535-551.
Myers et al., "Optimal Alignments in Linear Space", Bioinformatics, Computer Applications in the Biosciences, vol. 4, No. 1, 1988, pp. 11-17.
Naggert et al., "Cloning, Sequencing, and Characterization of *Escherichia coli* Thioesterase II", The Journal of Biological Chemistry, vol. 266, No. 17, Jun. 15, 1991, pp. 11044-11050.
Neyfakh, Alexander A, "The Multidrug Efflux Transporter of Bacillus Subtilis is a Structural and Functional Homolog of the *Staphylococcus* NorA Protein", Antimicrobial Agents Chemotherapy, vol. 36, No. 2, Feb. 1992, pp. 484-485.
Ng et al., "Quinolone Resistance Mediated by norA: Physiologic Characterization and Relationship to flqB, a Quinolone Resistance Locus on the *Staphylococcus aureus* Chromosome", Antimicrobial Agents and Chemotherapy, vol. 38, No. 6, Jun. 1994, pp. 1345-1355.
Nishimaki et al., "Studies on the Metabolism of Unsaturated Fatty Acids XIV. Purification and Properties of NADPH-Dependent Trans-2-Enoyl-CoA Reductase of *Escherichia coli* K-12", Journal of Biochemistry, vol. 95, No. 5, 1984, pp. 1315-1321.
Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109", Applied and Environmental Microbiology, vol. 71, No. 8, Aug. 2005, pp. 4297-4306.
Ochsner et al., "Methylobacterium extorquens: methylotrophy and biotechnological applications", Applied Microbiology and Biotechnology, vol. 99, No. 2, 2015, pp. 517-534. {Abstract}.
Ohashi et al., "Continuous Production of Lactic Acid from Molasses by Perfusion Culture of Lactococcus Lactis Using a Stirred Ceramic Membrane Reactor", Journal of Bioscience and Bioengineering, vol. 87, No. 5, 1999, pp. 647-654.
Papanikolaou et al., "Citric Acid Production by Yarrowia Lipolytica Cultivated on Olive-Mill Wastewater-Based Media", Bioresource Technology, vol. 99, No. 7, 2008, pp. 2419-2428.
Paukert et al., "Formyl-Methenyl-Methylenetetrahydrofolate Synthetase (Combined): Correlation of Enzymic Activities with Limited Proteolytic Degradation of the Protein from Yeast", Biochemical and Biophysical Research Communications, vol. 77, Issue 1, Jul. 11, 1977, pp. 147-154.
Paukert et al., "Formyl-Methyl-Methylenetetrahydrofolate Synthetase-(Combined). An Ovine Protein with Multiple Catalytic Activities" The Journal of Biological Chemistry, vol. 251, Aug. 25, 1976, pp. 5104-5111.
PCT International Preliminary Report on Patentability issued in International Patent Application No. PCT/US2017/043712, dated Jan. 29, 2019, 10 pages.
PCT International Search Report issued in International Patent Application No. PCT/US2017/043712, dated Feb. 1, 2018, 5 pages.
PCT Written Opinion of the International Searching Authority issued in International Patent Application No. PCT/US2017/043712, dated Feb. 1, 2018, 9 pages.
Pearson et al., "Improved Tools for Biological Sequence Comparison", Proceedings of the National Academy of Sciences, Biochemistry, vol. 85, Apr. 1988, pp. 2444-2448.
Perez-Pantoja et al., "Metabolic Reconstruction of Aromatic Compounds Degradation from the Genome of the Amazing Pollutant-Degrading Bacterium Cupriavidus Necator JMP134", FEMS Microbiology Reviews, vol. 32, Aug. 7, 2008, pp. 736-794.
Pino et al., "Mitochondrial Translation in Absence of Local tRNA Aminoacylation and Methionyl tRNAMet Formylation in Apicomplexa", Molecular Microbiology, vol. 76, Issue 3, May 2010, pp. 706-718.
Przybylski et al., "Third-Generation Feed Stocks for the Clean and Sustainable Biotechnological Production of Bulk Chemicals: Synthesis of 2-Hydroxyisobutyric Acid", Energy, Sustainability and Society, vol. 2, No. 11, 2012, 9 pages.
Ramsay et al., "Use of a Nylon Manufacturing Waste as an industrial Fermentation Substrate", Applied and Environmental Microbiology, vol. 52, No. 1, Jul. 1986, pp. 152-156.
Refseq, "Multispecies: 4'-Phosphopantetheinyl Transferase [Bacillus]", Accession No. WP_003234549.1, Apr. 23, 2017, 1 page.
Refseq, "Putrescine:2-Oxoglutaric Acid Aminotransferase, PLP-Dependent [*Escherichia coli* Str. K-12 Substr. MG1655]", Accession No. NP_417544.5, Aug. 8, 2016, 3 pages.
Sah et al., "One-Carbon Metabolic Pathway Rewiring in *Escherichia coli* Reveals an Evolutionary Advantage of 10-Formyltetrahydrofolate Synthetase (Fhs) in Survival Under Hypoxia", Journal of Bacteriology, vol. 197, No. 4, Feb. 2015, pp. 717-726.
Samsonova et al., "Molecular Cloning and Characterization of *Escherichia coli* K12 ygjG Gene", BMC Microbiology, vol. 3, No. 2, Jan. 31, 2003, pp. 1-10.
Satoh et al., "Enzyme-Catalyzed Poly(3-Hydroxybutyrate) Synthesis from Acetate with CoA Recycling and NADPH Regeneration in Vitro", Journal of Bioscience and Bioengineering, vol. 95, No. 4, 2003, pp. 335-341.

(56) References Cited

OTHER PUBLICATIONS

Seedorf et al., "The Genome of Clostridium Kluyveri, A Strict Anaerobe with Unique Metabolic Features", PNAS USA, vol. 105, No. 6, Feb. 12, 2008, pp. 2128-2133.

Shen et al., "Driving Forces Enable High-Titer Anaerobic 1-Butanol Synthesis in *Escherichia coli*", Applied and Environmental Microbiology, vol. 77, No. 9, May 2011, pp. 2905-2915.

Shikata et al., "A Novel ADP-Forming Succinyl-CoA Synthetase in Thermococcus Kodakaraensis Structurally Related to the Archaeal Nucleoside Diphosphate-Forming Acetyl-CoA Synthetases", The Journal of Biological Chemistry, vol. 282, No. 37, Sep. 14, 2007, pp. 26963-26970.

Slater et al., "Multiple β-Ketothiolases Mediate Poly(β-Hydroxyalkanoate) Copolymer Synthesis in Ralstonia Eutropha", Journal of Bacteriology, vol. 180, No. 8, Apr. 1998, pp. 1979-1987.

Slesarev et al., "The Complete Genome of Hyperthermophile Methanopyrus Kandleri AV19 and Monophyly of Archaeal Methanogens", Proceeding of the National Academy of Sciences of the United States of America, vol. 99, No. 7, Apr. 2, 2002, pp. 4644-4649.

Stanbury et al., "Principles of Fermentation Technology", 2nd edition, Aeration and Agitation, 1995, 14 pages.

Suzuki et al., "Acetylputrescine Deacetylase from Micrococcus Luteus K-11", Biochimica et Biophysica Acta (BBA)—General Subjects, vol. 882, Issue 1, Jun. 1986, pp. 140-142.

Suzuki et al., "GriC and GriD Constitute a Carboxylic Acid Reductase Involved in Grixazone Biosynthesis in Streptomyces Griseus", Journal of Antibiotics, vol. 60, No. 6, 2007, pp. 380-387.

Uniprotkb, "Alcohol Dehydrogenase YqhD", Accession No. Q46856, Nov. 1, 1996, 5 pages.

Uniprotkb, "Bifunctional Protein FolD", Accession No. B7LJI7, Feb. 10, 2009, 5 pages.

Uniprotkb, "Bifunctional Protein FolD", Accession No. P24186, Jan. 23, 2007, 5 pages.

Uniprotkb, "Bifunctional Protein FolD", Accession No. Q32JK7, Jan. 23, 2007, 4 pages.

Uniprotkb, "Formate Acetyltransferase 1", Accession No. P09373.2, Jan. 23, 2007, 7 pages.

Uniprotkb, "Formate—Tetrahydrofolate Ligase 1", Accession No. Q251P8, Apr. 18, 2006, 4 pages.

Uniprotkb, "Formate—Tetrahydrofolate Ligase", Accession No. A8MIN1, Dec. 4, 2007, 4 pages.

Uniprotkb, "Formate—Tetrahydrofolate Ligase", Accession No. P13419, Jan. 1, 1990, 4 pages.

Uniprotkb, "Formate—Tetrahydrofolate Ligase", Accession No. Q5XZD9, Nov. 23, 2004, 4 pages.

Uniprotkb, "Formate—Tetrahydrofolate Ligase", Accession Nos. Q07064, Oct. 1, 1994, 4 pages.

Uniprotkb, "PFL-Like Enzyme TdcE", Accession No. P42632, Oct. 11, 2004, 7 pages.

Uniprotkb, "S-(Hydroxymethyl)Glutathione Dehydrogenase", Accession No. A0A0M7MPD4, Dec. 9, 2015, 4 pages.

Uniprotkb, "S-(Hydroxymethyl)Glutathione Dehydrogenase", Accession No. P25437, Nov. 1, 1997, 6 pages.

Uniprotkb, "S-(Hydroxymethyl)Glutathione Dehydrogenase", Accession No. Q3Z550, Sep. 27, 2005, 5 pages.

Uniprotkb, "S-(Hydroxymethyl)Glutathione Dehydrogenase", Accession No. W1AV69, Mar. 19, 2014, 4 pages.

Uniprotkb, "S-Formylglutathione Hydrolase FrmB", Accession No. P51025, Nov. 1, 1997, 5 pages.

Uniprotkb, "S-Formylglutathione Hydrolase FrmB", Accession No. Q3Z551, Sep. 27, 2005, 4 pages.

Uniprotkb, "S-Formylglutathione Hydrolase", Accession No. A0A0M9J3Q3, Dec. 9, 2015, 3 pages.

Uniprotkb, "S-Formylglutathione Hydrolase", Accession No. W1ATJ0, Mar. 19, 2014, 3 pages.

Venkitasubramanian et al., "Aldehyde Oxidoreductase as a Biocatalyst: Reductions of Vanillic Acid", Enzyme and Microbial Technology, vol. 42, No. 2, Jan. 2008, pp. 130-137.

Wee et al., "Biotechnological Production of Lactic Acid and Its Recent Applications", Food Technology and Biotechnology, vol. 44, No. 2, 2006, pp. 163-172.

Whitehead et al., "Distribution of 10-Formyltetrahydrofolate Synthetase in Eubacteria", Journal of Bacteriology, vol. 170, No. 2, 1988, pp. 995-997.

Woolridge et al., "Efflux of the Natural Polyamine Spermidine Facilitated by the Bacillus Subtilis Multidrug Transporter Bit", The Journal of Biological Chemistry, vol. 272, No. 14, Apr. 4, 1997, pp. 8864-8866.

Yang et al., "Value-Added Uses for Crude Glycerol-a Byproduct of Biodiesel Production", Biotechnology for Biofuels, vol. 5, No. 13, 2012, pp. 1-10.

Yonaha et al., "4-Aminobutyrate: 2-Oxoglutarate Aminotransferase of Streptomyces Griseus: Purification and Properties", European Journal of Biochemistry, vol. 146, Jan. 1985, pp. 101-106.

Zhuang et al., "Divergence of Function in the Hot Dog Fold Enzyme Superfamily: The Bacterial Thioesterase YciAt", Biochemistry, vol. 47, No. 9, Feb. 2, 2008 pp. 2789-2796.

* cited by examiner

| Strain | Growth condition |
|---|---|
| [1] Pimelate strain | Growth on glycerol |
| [2] ΔfolD/p-fhs strain<br>Enzyme  Gene  Organism  Operon<br>1.5.1.5   folD   E. coli    folD-ybcl | Growth on Glycerol + Glycine + purine<br>No growth on Glycerol |
| [3] ΔfolD::fhs strain<br>Enzyme  Gene  Organism        Operon<br>1.5.1.5   folD   E. coli              folD-ybcl<br>6.3.4.3   fhs    C. cylindrosporum  clofolsyn | Growth on Glycerol + Glycine + purine<br>No growth on Glycerol |
| [4] ΔfolD/ΔpflBtdcE::fhs strain<br>Enzyme  Gene  Organism        Operon<br>1.5.1.5   folD   E. coli              folD-ybcl<br>6.3.4.3   fhs    C. cylindrosporum  clofolsyn<br>2.3.1.54  pflB   E. coli              pflB<br>2.3.1.54  tdcE   E. coli              tdcBCDEFG | No growth on Glycerol<br>Growth on Glycerol + formate |

MATERIALS AND METHODS FOR THE BIOSYNTHESIS OF SEVEN CARBON CHEMICALS IN THE PRESENCE OF METHANOL OXIDATION

CROSS-REFERENCE TO RELATED APPLICATIONS

The present application is a continuation of U.S. application Ser. No. 15/659,521, filed Jul. 25, 2017, which claims the benefit of U.S. Provisional Application No. 62/366,549, filed Jul. 25, 2016, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 25, 2017, is named 12444_0685-00000_SL.txt and is 167,292 bytes in size.

TECHNICAL FIELD

The invention relates to methods for regulating the biosynthesis of one or more seven carbon compounds. This invention relates to materials and methods for biosynthesizing one or more of pimelic acid, 7-aminoheptanoic acid (7-AHA), 7-hydroxyheptanoic acid, heptamethylenediamine, 7-aminoheptanol, and 1,7-heptanediol (hereafter "C7 building blocks") from malonyl-CoA or malonyl-[acp] and optionally acetyl-CoA using polypeptides having the activity of one or more enzymes such as methyltransferases, β-ketoacyl-[acp] synthases, β-ketothiolases, dehydrogenases, reductases, hydratases, thioesterases, esterases, CoA-transferases, reversible CoA-ligases, and transaminases or using recombinant host cells expressing one or more such enzymes in genetically modified hosts. The invention further relates to coupling a modified tetrahydrofolate metabolic cycle (THF-MC) to the biosynthesis of C7 building blocks by forcing the modified THF-MC to utilize formate derived from methanol oxidation, wherein the methanol is a byproduct of the C7 building block biosynthesis pathway.

BACKGROUND

Nylons are synthetic polyamides which are sometimes synthesized by the condensation polymerisation of a diamine with a dicarboxylic acid. Similarly, Nylons may be produced by the condensation polymerisation of lactams. A ubiquitous Nylon is Nylon 6,6, which is produced by reaction of hexamethylenediamine (HMD) and adipic acid. Nylon 6 is produced by a ring opening polymerisation of caprolactam (Anton & Baird, Polyamides Fibers, Encyclopedia of Polymer Science and Technology, 2001).

Nylon 7 and Nylon 7,7 represent novel polyamides with value-added characteristics compared to Nylon 6 and Nylon 6,6. Nylon 7 is produced by polymerisation of 7-aminoheptanoic acid (7-AHA), whereas Nylon 7,7 is produced by condensation polymerisation of pimelic acid and heptamethylenediamine. No economically viable petrochemical routes exist to producing the monomers for Nylon 7 and Nylon 7,7.

Given no economically cost competitive petrochemical monomer feedstocks, biotechnology offers an alternative approach via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

However, no wild-type prokaryote or eukaryote naturally overproduces or excretes C7 building blocks to the extracellular environment. Nevertheless, the metabolism of pimelic acid has been reported.

The dicarboxylic acid, pimelic acid, is converted efficiently as a carbon source by a number of bacteria and yeasts via β-oxidation into central precursors. β-oxidation of coenzyme A (CoA) activated pimelate to CoA-activated 3-oxopimelate facilitates further catabolism via, for example, pathways associated with aromatic substrate degradation. The catabolism of 3-oxopimeloyl-CoA to acetyl-CoA and glutaryl-CoA by several bacteria has been characterized comprehensively (Harwood and Parales, *Annual Review of Microbiology*, 1996, 50, 553-590).

The biosynthesis of C7 building blocks by recombinant host microorganisms has been described in U.S. Patent Publication Nos. 2014/0186904 and 2014/0242655.

The optimality principle states that microorganisms regulate their biochemical networks to support maximum biomass growth. Beyond the need to express heterologous pathways in a host organism, directing carbon flux toward C7 building blocks that serve as carbon sources, rather than to biomass growth constituents, contradicts the optimality principle. For example, transferring the 1-butanol pathway from *Clostridium* species into other production strains has often fallen short by an order of magnitude compared to the production performance of native producers (Shen et al., *Appl. Environ. Microbiol.*, 2011, 77(9), 2905-2915).

The synthesis of the seven carbon aliphatic backbone precursor is a key consideration in synthesizing C7 building blocks prior to forming terminal functional groups, such as carboxyl, amine, or hydroxyl groups, on the C7 aliphatic backbone.

SUMMARY

Accordingly, against this background, it is clear that there is a need for methods for producing pimelic acid, 7-aminoheptanoic acid, heptamethylenediamine, 7-aminoheptanol, 7-hydroxyheptanoic acid, and 1,7-heptanediol (hereafter "C7 building blocks"), wherein the methods are biocatalyst-based. By making the host organism dependent on a byproduct of the biosynthesis of C7 building blocks, the host channels flux through the pathway leading to the C7 building block product, thus increasing yield, titre, and productivity.

This disclosure is based at least in part on the discovery that it is possible to construct biochemical pathways for producing a seven carbon chain aliphatic backbone precursor, in which one or two functional groups, i.e., carboxyl, amine, or hydroxyl, can be formed, leading to the synthesis of one or more of pimelic acid, 7-aminoheptanoate, 7-hydroxyheptanoate, heptamethylenediamine, 7-aminoheptanol, and 1,7-heptanediol (C7 building blocks), or salts or derivatives thereof. Pimelic acid and pimelate, pimelyl and pimeloyl, 7-hydroxyheptanoic acid and 7-hydroxyheptanoate, and 7-aminoheptanoic and 7-aminoheptanoate are used interchangeably herein to refer to the compound in any of its neutral or ionized forms, including any salt forms thereof. It is understood by those skilled in the art that the specific form will depend on pH.

For compounds containing carboxylic acid groups such as organic monoacids, hydroxyacids, aminoacids, and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The salt can be isolated as is from the system as the salt or converted to the free acid by reducing the pH to below the pKa through addition of acid or treatment with an acidic ion exchange resin.

For compounds containing amine groups such as, but not limited to, organic amines, aminoacids, and diamines, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, or muconic acid. Acceptable inorganic bases are known in the art and include aluminum hydroxide, calcium hydroxide, potassium hydroxide, sodium carbonate, sodium hydroxide, and the like. The salt can be isolated as is from the system as a salt or converted to the free amine by raising the pH to above the pKb through addition of base or treatment with a basic ion exchange resin.

For compounds containing both amine groups and carboxylic acid groups such as, but not limited to, aminoacids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid Acceptable inorganic bases include aluminum hydroxide, calcium hydroxide, potassium hydroxide, sodium carbonate, sodium hydroxide, and the like or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, tromethamine, N-methylglucamine, and the like. Acceptable inorganic bases are known in the art and include aluminum hydroxide, calcium hydroxide, potassium hydroxide, sodium carbonate, sodium hydroxide, and the like. The salt can be isolated as is from the system or converted to the free acid by reducing the pH to below the pKa through addition of acid or treatment with an acidic ion exchange resin.

These pathways and metabolic engineering and cultivation strategies described herein rely on fatty acid elongation and synthesis enzymes or homologs accepting methyl-ester shielded dicarboxylic acids as substrates.

This disclosure is further based on increasing flux through the C7 building block biosynthesis pathway by making methanol, a byproduct of the pathway, a requirement for cell growth. This disclosure is also related to using methanol for cell growth.

The present disclosure provides methods for biosynthesizing one or more seven carbon compounds (C7 building blocks) and for regulating the biosynthesis of a C7 building block product using a pathway having a pimeloyl-ACP intermediate. In some embodiments, this method comprises converting methanol to formate, wherein the formate is used in the conversion of tetrahydrofolate to $N^{10}$-formyl-tetrahydrofolate. In some embodiments, methanol is converted to formate via spontaneous enzymatic reactions. In one embodiment, the methanol is produced during BioH enzyme activity, wherein BioH removes the methyl group from pimelyl-ACP methyl ester during conversion of pimeloyl-ACP methyl ester to pimeloyl-ACP.

In some embodiments, the product may be a salt or derivative thereof of a C7 building block.

In some embodiments, the method comprises the step of downregulating activity of bifunctional protein FolD (FolD). In one embodiment, the step of downregulating the activity of FolD comprises a step of deleting folD. In some embodiments, the method comprises the step of cloning in, or knocking in, a formate-tetrahydrofolate ligase. In one embodiment, the formate-tetrahydrofolate ligase has at least 70%, at least 80%, or at least 90% sequence identity or homology to an amino acid chosen from SEQ ID NOs: 18-22.

In some embodiments, the method comprises the step of downregulating the activity of formate acetyltransferase 1 (PflB) and PFL-like enzyme TdcE (TdcE). In one embodiment, the step of downregulating the activity of PflB and TdcE comprises a step of deleting pflB and tdcE.

In some embodiments, the method comprises a step of cloning in, or knocking in, an alcohol dehydrogenase. In some embodiments an alcohol dehydrogenase converts the methanol to formaldehyde. In one embodiment, the alcohol dehydrogenase has at least 70%, at least 80%, or at least 90% sequence identity or homology to the amino acid sequence set forth in SEQ ID NO: 31.

In some embodiments, the method comprises a step of cloning in, or knocking in, a S-(hydroxymethyl) glutathione dehydrogenase (frmA). In some embodiments, a S-(hydroxymethyl) glutathione dehydrogenase converts S-hydroxymethylglutathione to S-formylgluathione. In one embodiment, the S-(hydroxymethyl) glutathione dehydrogenase has at least 70%, at least 80%, or at least 90% sequence identity or homology to an amino acid sequence chosen from SEQ ID NOs: 23-26.

In some embodiments, the method comprises a step of cloning in, or knocking in, a S-formylglutathione hydrolase (frmB). In some embodiments, a S-formylglutathione hydrolase converts S-formylglutathione to formate. In one embodiment, the S-formylglutathione hydrolase has at least 70%, at least 80%, or at least 90% sequence identity or homology to an amino acid sequence chosen from SEQ ID NOs: 27-30.

In some embodiments, the expression of adh, frmA, and frmB gene products allows conversion of the methanol to formate.

In some embodiments, the biosynthesis of the product is increased.

In some embodiments, the method is performed in a recombinant host.

In some embodiments, the host is subjected to a cultivation strategy under aerobic, anaerobic, micro-aerobic or mixed oxygen/denitrification cultivation conditions. In one embodiment, the host is cultured under conditions of nutrient limitation.

In some embodiments, the host is retained using a ceramic hollow fiber membrane to maintain a high cell density during fermentation. In one embodiment, the principal carbon source fed to the fermentation derives from biological or non-biological feedstocks.

In some embodiment, the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste. In some embodiments, the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

In some embodiments, the host is a prokaryote. In one embodiment, the host is from the genus *Escherichia* such as *Escherichia coli*; from the genus *Clostridia* such as *Clostridium ljungdahlii, Clostridium autoethanogenum,* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida,* or *Pseudomonas oleavorans*; from the genus *Delftia* such as *Delftia acidovorans*, from the genus *Bacillus* such as *Bacillus subtillis*; from the genus *Lactobacillus* such as *Lactobacillus delbrueckii*; from the genus *Lactococcus* such as *Lactococcus lactis*; or from the genus *Rhodococcus* such as *Rhodococcus equi*. For example, the host may be *Escherichia coli*.

In some embodiments, the host is a eukaryote. In one embodiment, the host is from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*, from the genus *Issatchenkia* such as *Issathenkia orientalis*, from the genus *Debaryomyces* such as *Debaryomyces hansenii*, from the genus *Arxula* such as *Arxula adenoinivorans*, or from the genus *Kluyveromyces* such as *Kluyveromyces lactis*.

In some embodiments, the host's tolerance to high concentrations of a C7 building block is improved through continuous cultivation in a selective environment.

In some embodiments, the host comprises one or more of the following attenuated enzymes: polyhydroxyalkanoate synthase, an acetyl-CoA thioesterase, an acetyl-CoA specific β-ketothiolase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, a transhydrogenase dissipating the NADH or NADPH imbalance, an glutamate dehydrogenase dissipating the NADH or NADPH imbalance, a NADH/NADPH-utilizing glutamate dehydrogenase, a pimeloyl-CoA dehydrogenase; an acyl-CoA dehydrogenase accepting C7 building blocks and central precursors as substrates, a glutaryl-CoA dehydrogenase, or a pimeloyl-CoA synthetase.

In some embodiments, the host expresses or overexpresses one or more of the following enzymes: an acetyl-CoA synthetase; a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a L-alanine dehydrogenase; a L-glutamate dehydrogenase specific to the NADH or NADPH used to generate a co-factor imbalance; a methanol dehydrogenase; a formaldehyde dehydrogenase; a diamine transporter; a dicarboxylate transporter; an S-adenosylmethionine synthetase; and/or a multidrug transporter.

The present disclosure also provides a recombinant host for producing pimeloyl-ACP, wherein the host comprises at least one exogenous nucleic acid encoding (i) a formate-tetrahydrofolate ligase, (ii) a S-(hydroxymethyl) glutathione dehydrogenase, and an (iii) a S-formylglutathione hydrolase, or the host has (i) a formate-tetrahydrofolate ligase, (ii) a S-(hydroxymethyl) glutathione dehydrogenase, and an (iii) a S-formylglutathione hydrolase knocked in.

In some embodiments, the host comprises deletion of folD. In some embodiments, the host comprises a deletion of pflB and tdcE.

In some embodiments, the host comprises at least one exogenous nucleic acid encoding an alcohol dehydrogenase. In one embodiment, the host has a knock in of alcohol dehydrogenase. In some embodiments, the host comprises at least one exogenous nucleic acid encoding one or more of a thioesterase, an aldehyde dehydrogenase, a 7-oxoheptanoate dehydrogenase, a 6-oxohexanoate dehydrogenase, a glutaconate CoA-transferase, a reversible succinyl-CoA ligase, an acetylating aldehyde dehydrogenase, or a carboxylate reductase, said host producing pimelic acid or pimelate semialdehyde.

In one embodiment, the host comprises at least one exogenous nucleic acid encoding a ω-transaminase, wherein the host produces 7-aminoheptanoate.

In some embodiments, the host further comprises at least one exogenous nucleic acid encoding a ω-transaminase, a deacetylase, an N-acetyltransferase, or an alcohol dehydrogenase, said host producing heptamethylenediamine.

In some embodiments, the host comprises at least one exogenous nucleic acid encoding a (i) carboxylate reductase enhanced by a phosphopantetheinyl transferase or (ii) an alcohol dehydrogenase, said host producing 1,7-heptanediol.

This disclosure also relates to non-naturally occurring organisms comprising at least one exogenous nucleic acid encoding at least one polypeptide having the activity of at least one enzyme depicted in any one of FIGS. 1 to 11.

The present disclosure also provides methods of using methanol for cell growth of a recombinant host.

In some embodiments, the method comprises the step of deleting folD.

In some embodiments, the method comprises the step of cloning in, or knocking in, aformate-tetrahydrofolate ligase (fhs).

In some embodiments, the method comprises the step of deleting pflB and tdcE.

In some embodiments, the method comprises the step of cloning in an alcohol dehydrogenase (adh), a S-(hydroxymethyl) glutathione dehydrogenase (frmA), and a S-formylglutathione hydrolase.

In some embodiments, the recombinant host converts methanol to formate. In some embodiments, formate is required for the synthesis of purines and initiator tRNA.

This disclosure also relates to nucleic acid constructs or expression vectors comprising a polynucleotide encoding a polypeptide, wherein the polynucleotide is operably linked to one or more heterologous control sequences that direct production of the polypeptide.

In some embodiments, the polypeptide has formate-tetrahydrofolate ligase activity, wherein the polynucleotide is operably linked to one or more heterologous control sequences that direct production of the polypeptide and wherein the polypeptide having formate-tetrahydrofolate ligase activity is selected from a polypeptide having at least 70% sequence identity or homology to the polypeptide of any one of SEQ ID NOs: 18-22.

In some embodiments, the polypeptide has alcohol dehydrogenase activity, wherein the polynucleotide is operably linked to one or more heterologous control sequences that direct production of the polypeptide and wherein the polypeptide having alcohol dehydrogenase activity has at least 70% sequence identity or homology to the polypeptide of SEQ ID NO: 31.

In some embodiments, the polypeptide has S-(hydroxymethyl) glutathione dehydrogenase activity, wherein the polynucleotide is operably linked to one or more heterologous control sequences that direct production of the polypeptide and wherein the polypeptide having S-(hydroxymethyl) glutathione dehydrogenase activity has at least 70% sequence identity or homology to the polypeptide of any one of SEQ ID NOs: 23-26.

In some embodiments the polypeptide has S-formylglutathione hydrolase activity, wherein the polynucleotide is operably linked to one or more heterologous control sequences that direct production of the polypeptide and wherein the polypeptide having S-formylglutathione hydrolase activity has at least 70% sequence identity or homology to the polypeptide of any one of SEQ ID NOs: 27-30.

The present disclosure relates to the following additional embodiments:

1. A method for regulating biosynthesis of a product chosen from pimelic acid, 7-aminoheptanoate, 7-hydroxyheptanoate, heptamethylenediamine, 7-aminoheptanol, and 1,7-heptanediol, or salts and derivatives thereof, using a pathway having a pimeloyl-ACP intermediate, the method comprising converting methanol to formate via at least one spontaneous enzymatic reaction, wherein the formate is used in the conversion of tetrahydrofolate to $N^{10}$-formyl-tetrahydrofolate.

2. The method of embodiment 1, wherein the methanol is produced via BioH enzyme activity.

3. The method of embodiment 2, wherein BioH removes the methyl group from pimeloyl-ACP methyl ester during conversion of pimeloyl-ACP methyl ester to pimeloyl-ACP.

4. The method of any one of embodiments 1 to 3, wherein the method comprises the step of downregulating the activity of FolD.

5. The method of embodiment 4, wherein the step of downregulating the activity of FolD comprises a step of attenuating folD.

6. The method of embodiment 4, wherein the method comprises the step of cloning in a formate-tetrahydrofolate ligase (fhs).

7. The method of embodiment 6, wherein the formate-tetrahydrofolate ligase has at least 70%, at least 80%, or at least 90% sequence identity or homology to an amino acid sequence chosen from SEQ ID NOs: 18-22.

8. The method of any one of embodiments 4 to 7, wherein the method comprises the step of downregulating the activity of PflB and TdcE.

9. The method of embodiment 8, wherein the step of downregulating the activity of PflB and TdcE comprises a step of deleting pflB and tdcE.

10. The method of any one of embodiments 1 to 9, wherein the method comprises a step of cloning in an alcohol dehydrogenase (adh).

11. The method of embodiment 10, wherein the alcohol dehydrogenase converts the methanol to formaldehyde.

12. The method of embodiment 11, wherein the alcohol dehydrogenase has at least 70%, at least 80%, or at least 90% sequence identity or homology to the amino acid sequence set forth in SEQ ID NO: 31.

13. The method of any one of embodiments 1 to 12, wherein the method comprises a step of cloning in a S-(hydroxymethyl) glutathione dehydrogenase (frmA).

14. The method of embodiment 13, wherein the S-(hydroxymethyl) glutathione dehydrogenase converts S-hydroxymethylglutathione to S-formylgluathione.

15. The method of embodiment 14, wherein the S-(hydroxymethyl) glutathione dehydrogenase has at least 70%, at least 80%, or at least 90% sequence identity or homology to an amino acid sequence chosen from SEQ ID NOs: 23-26.

16. The method of any one of embodiments 1 to 15, wherein the method comprises a step of cloning in a S-formylglutathione hydrolase (frmB).

17. The method of embodiment 16, wherein the S-formylglutathione hydrolase converts S-formylglutathione to formate.

18. The method of embodiment 17, wherein the S-formylglutathione hydrolase has at least 70%, at least 80%, or at least 90% sequence identity or homology to an amino acid sequence chosen from SEQ ID NOs: 27-30.

19. The method of any one of embodiments 16 to 18, wherein the expression of adh, frmA, and frmB allows conversion of methanol to formate.

20. The method of any of the preceding embodiments, wherein the biosynthesis of the product is increased.

21. The method of any of the preceding embodiments, wherein the product is chosen from salts and derivatives thereof of pimelic acid, 7-aminoheptanoate, 7-hydroxyheptanoate, heptamethylenediamine, 7-aminoheptanol, and 1,7-heptanediol.

22. The method of any of the preceding embodiments, wherein the method is performed in a recombinant host.

23. The method of embodiment 22, wherein the host is subjected to a cultivation strategy under aerobic, anaerobic, micro-aerobic, or mixed oxygen/denitrification cultivation conditions.

24. The method of embodiment 22 or 23, wherein the host is cultured under conditions of nutrient limitation.

25. The method according to any one of embodiments 22 to 24, wherein the host is retained using a ceramic hollow fiber membrane to maintain a high cell density during fermentation.

26. The method of any one of embodiments 22 to 25, wherein the principal carbon source fed to the fermentation derives from biological or non-biological feedstocks.

27. The method of embodiment 26, wherein the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste.

28. The method of embodiment 26, wherein the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

29. The method of any one of embodiments 22 to 28, wherein the host is a prokaryote.

30. The method of embodiment 29, wherein the prokaryote is from the genus *Escherichia* such as *Escherichia coli*; from the genus *Clostridia* such as *Clostridium ljungdahlii*, *Clostridium autoethanogenum*, or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida*, or *Pseudomonas oleavorans*; from the genus *Delftia* such as *Delftia acidovorans*, from the genus *Bacillus* such as *Bacillus subtillis*; from the genus *Lactobacillus* such as *Lactobacillus delbrueckii*; from the genus *Lactococcus* such as *Lactococcus lactis*; or from the genus *Rhodococcus* such as *Rhodococcus equi*.

31. The method of embodiment 30, wherein the host is *Escherichia coli*.

32. The method of any one of embodiments 22 to 28, wherein the host is a eukaryote.

33. The method of embodiment 32, wherein the eukaryote is from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

34. The method of embodiment 22, wherein the host's tolerance to high concentrations of a C7 building block is improved through continuous cultivation in a selective environment.

35. The method of any one of embodiments 22 to 34, wherein the host comprises one or more of the following attenuated enzymes: polyhydroxyalkanoate synthase; an acetyl-CoA thioesterase; an acetyl-CoA specific β-ketothiolase; a phosphotransacetylase forming acetate; an acetate kinase; a lactate dehydrogenase; a menaquinol-fumarate oxidoreductase; a 2-oxoacid decarboxylase producing isobutanol; an alcohol dehydrogenase forming ethanol; a triose phosphate isomerase; a pyruvate decarboxylase; a glucose-6-phosphate isomerase; a transhydrogenase dissipating the NADH or NADPH imbalance; an glutamate dehydrogenase dissipating the NADH or NADPH imbalance; a NADH/NADPH-utilizing glutamate dehydrogenase; a pimeloyl-CoA dehydrogenase; an acyl-CoA dehydrogenase accepting C7 building blocks and central precursors as substrates; a glutaryl-CoA dehydrogenase; or a pimeloyl-CoA synthetase.

36. The method of any one of embodiments 22 to 34, wherein the host overexpresses one or more genes encoding: an acetyl-CoA synthetase; a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a L-alanine dehydrogenase; a L-glutamate dehydrogenase specific to the NADH or NADPH used to generate a co-factor imbalance; a methanol dehydrogenase; a formaldehyde dehydrogenase; a diamine transporter; a dicarboxylate transporter; an S-adenosylmethionine synthetase; and/or a multidrug transporter.

37. A recombinant host for producing pimeloyl-ACP, wherein the host comprises at least one exogenous nucleic acid encoding (i) a formate-tetrahydrofolate ligase, (ii) a S-(hydroxymethyl) glutathione dehydrogenase, and an (iii) a S-formylglutathione hydrolase.

38. The recombinant host of embodiment 37, wherein the host comprises a deletion of folD.

39. The recombinant host of embodiment 37 or 38, wherein the host comprises a deletion of pflB and tdcE.

40. The recombination host of any one of embodiments 37 to 39, wherein the host further comprises at least one exogenous nucleic acid encoding an alcohol dehydrogenase.

41. The recombinant host of any one of embodiments 37 to 40, said host comprising at least one exogenous nucleic acid encoding one or more of a thioesterase, an aldehyde dehydrogenase, a 7-oxoheptanoate dehydrogenase, a 6-oxohexanoate dehydrogenase, a glutaconate CoA-transferase, a reversible succinyl-CoA ligase, an acetylating aldehyde dehydrogenase, or a carboxylate reductase, said host producing pimelic acid or pimelate semialdehyde.

42. The recombinant host of any one of embodiments 37 to 41, said host comprising at least one exogenous nucleic acid encoding a ω-transaminase, wherein the host produces 7-aminoheptanoate.

43. The recombinant host of any one of embodiments 37 to 42, said host further comprising one or more of a 4-hydroxybutyrate dehydrogenase, a 5-hydroxypentanoate dehydrogenase, or a 6-hydroxyhexanoate dehydrogenase, said host producing 7-hydroxyheptanoic acid.

44. The recombinant host of any one of embodiments 37 to 43, wherein the host further comprises at least one exogenous nucleic acid encoding a ω-transaminase, a deacetylase, an N-acetyltransferase, or an alcohol dehydrogenase, said host producing heptamethylenediamine.

45. The recombinant host of any one of embodiments 37 to 44, wherein the host further comprises at least one exogenous nucleic acid encoding a (i) carboxylate reductase enhanced by a phosphopantetheinyl transferase or (ii) an alcohol dehydrogenase, said host producing 1,7-heptanediol.

46. A method for using methanol as a requirement for growth of a recombinant host.

47. The method of embodiment 46, wherein the method comprises the step of deleting folD.

48. The method of embodiment 46 or 47, wherein the method comprises the step of cloning in aformate-tetrahydrofolate ligase (fhs).

49. The method of any one of embodiments 46 to 48, wherein the method comprises the step of deleting pflB and tdcE.

50. The method of any one of embodiments 46 to 49, wherein the method comprises the step of cloning in an alcohol dehydrogenase (adh), a S-(hydroxymethyl) glutathione dehydrogenase (frmA), and a S-formylglutathione hydrolase.

51. The method of any one of embodiments 46 to 50, wherein the recombinant host converts methanol to formate.

52. The method of any one of embodiments 46 to 51, wherein formate is required for the synthesis of purines and initiator tRNA.

53. A non-naturally occurring organism comprising at least one exogenous nucleic acid encoding at least one polypeptide having the activity of at least one enzyme depicted in any one of FIGS. 1 to 11.

54. A nucleic acid construct or expression vector comprising a polynucleotide encoding a polypeptide having formate-tetrahydrofolate ligase activity, wherein the polynucleotide is operably linked to one or more heterologous control sequences that direct production of the polypeptide and wherein the polypeptide having formate-tetrahydrofolate ligase activity is selected from: (a) a polypeptide having at least 70% sequence identity or homology to the polypeptide of SEQ ID NO: 18; (b) a polypeptide having at least 70% sequence identity or homology to the polypeptide of SEQ ID NO: 19; (c) a polypeptide having at least 70% sequence identity or homology to the polypeptide of SEQ ID NO: 20; (d) a polypeptide having at least 70% sequence identity or homology to the polypeptide of SEQ ID NO: 21; and (e) a polypeptide having at least 70% sequence identity or homology to the polypeptide of SEQ ID NO: 22.

55. A nucleic acid construct or expression vector comprising a polynucleotide encoding a polypeptide having alcohol dehydrogenase activity, wherein the polynucleotide is operably linked to one or more heterologous control sequences that direct production of the polypeptide and wherein the polypeptide having alcohol dehydrogenase is a polypeptide having at least 70% sequence identity or homology to the polypeptide of SEQ ID NO: 31.

56. A nucleic acid construct or expression vector comprising a polynucleotide encoding a polypeptide having S-(hydroxymethyl) glutathione dehydrogenase activity, wherein the polynucleotide is operably linked to one or more heterologous control sequences that direct production of the polypeptide and wherein the polypeptide having S-(hydroxymethyl) glutathione dehydrogenase activity is selected from: (a) a polypeptide having at least 70% sequence identity or homology to the polypeptide of SEQ ID NO: 23; (b) a polypeptide having at least 70% sequence identity or homology to the polypeptide of SEQ ID NO: 24; (c) a polypeptide having at least 70% sequence identity or homology to the polypeptide of SEQ ID NO: 25; and (d) a polypeptide having at least 70% sequence identity or homology to the polypeptide of SEQ ID NO: 26.

57. A nucleic acid construct or expression vector comprising a polynucleotide encoding a polypeptide having S-formylglutathione hydrolase activity, wherein the polynucleotide is operably linked to one or more heterologous control sequences that direct production of the polypeptide and wherein the polypeptide having S-formylglutathione hydrolase activity is selected from: (a) a polypeptide having at least 70% sequence identity or homology to the polypeptide of SEQ ID NO: 27; (b) a polypeptide having at least 70% sequence identity or homology to the polypeptide of SEQ ID NO: 28; (c) a polypeptide having at least 70% sequence identity or homology to the polypeptide of SEQ ID NO: 29; and (d) a polypeptide having at least 70% sequence identity or homology to the polypeptide of SEQ ID NO: 30.

58. A composition comprising the nucleic acid construct or expression vector of any one of embodiments 54 to 57.

59. A bio-derived, bio-based, or fermentation-derived product, wherein said product comprises:
(i) a composition comprising at least one bio-derived, bio-based, or fermentation-derived compound produced or biosynthesized according to the methods of any one of embodiments 1 to 36 or any one of FIGS. 1-7, or any combination thereof,
(ii) a bio-derived, bio-based, or fermentation-derived polymer comprising the bio-derived, bio-based, or fermentation-derived composition or compound of (i), or any combination thereof,
(iii) a bio-derived, bio-based, or fermentation-derived resin comprising the bio-derived, bio-based, or fermentation-derived compound or bio-derived, bio-based, or fermentation-derived composition of (i) or any combination thereof or the bio-derived, bio-based, or fermentation-derived polymer of (ii) or any combination thereof,
(iv) a molded substance obtained by molding the bio-derived, bio-based, or fermentation-derived polymer of (ii) or the bio-derived, bio-based, or fermentation-derived resin of (iii), or any combination thereof,
(v) a bio-derived, bio-based, or fermentation-derived formulation comprising the bio-derived, bio-based, or fermentation-derived composition of (i), bio-derived, bio-based, or fermentation-derived compound of (i), bio-derived, bio-based, or fermentation-derived polymer of (ii), bio-derived, bio-based, or fermentation-derived resin of (iii), or bio-derived, bio-based, or fermentation-derived molded substance of (iv), or any combination thereof, or
(vi) a bio-derived, bio-based, or fermentation-derived semi-solid or a non-semi-solid stream, comprising the bio-derived, bio-based, or fermentation-derived composition of (i), bio-derived, bio-based, or fermentation-derived compound of (i), bio-derived, bio-based, or fermentation-derived polymer of (ii), bio-derived, bio-based, or fermentation-derived resin of (iii), bio-derived, bio-based, or fermentation-derived formulation of (v), or bio-derived, bio-based, or fermentation-derived molded substance of (iv), or any combination thereof.

The details of one or more embodiments of the invention are set forth in the accompanying drawings and the description below. Other features, objects, and advantages of the invention will be apparent from the description and the drawings, and from the claims. It is to be understood that the foregoing general description and the following detailed description are exemplary and explanatory only, and are intended to provide further, non-limiting explanation of the disclosure.

BRIEF DESCRIPTION OF THE DRAWINGS

FIG. 8A shows a schematic of an example cloning strategy for producing a recombinant host strain that can assimilate methanol produced during BioH enzyme activity into essential purines and initiator tRNAs. The left column provides the strains including the appropriate modifications (e.g., knockout genes and exogenous nucleic acids) for each strain. The right column provides the growth conditions for each strain. The remainder of the cloning strategy is represented in FIG. 8B.

DETAILED DESCRIPTION

Figure 1A:
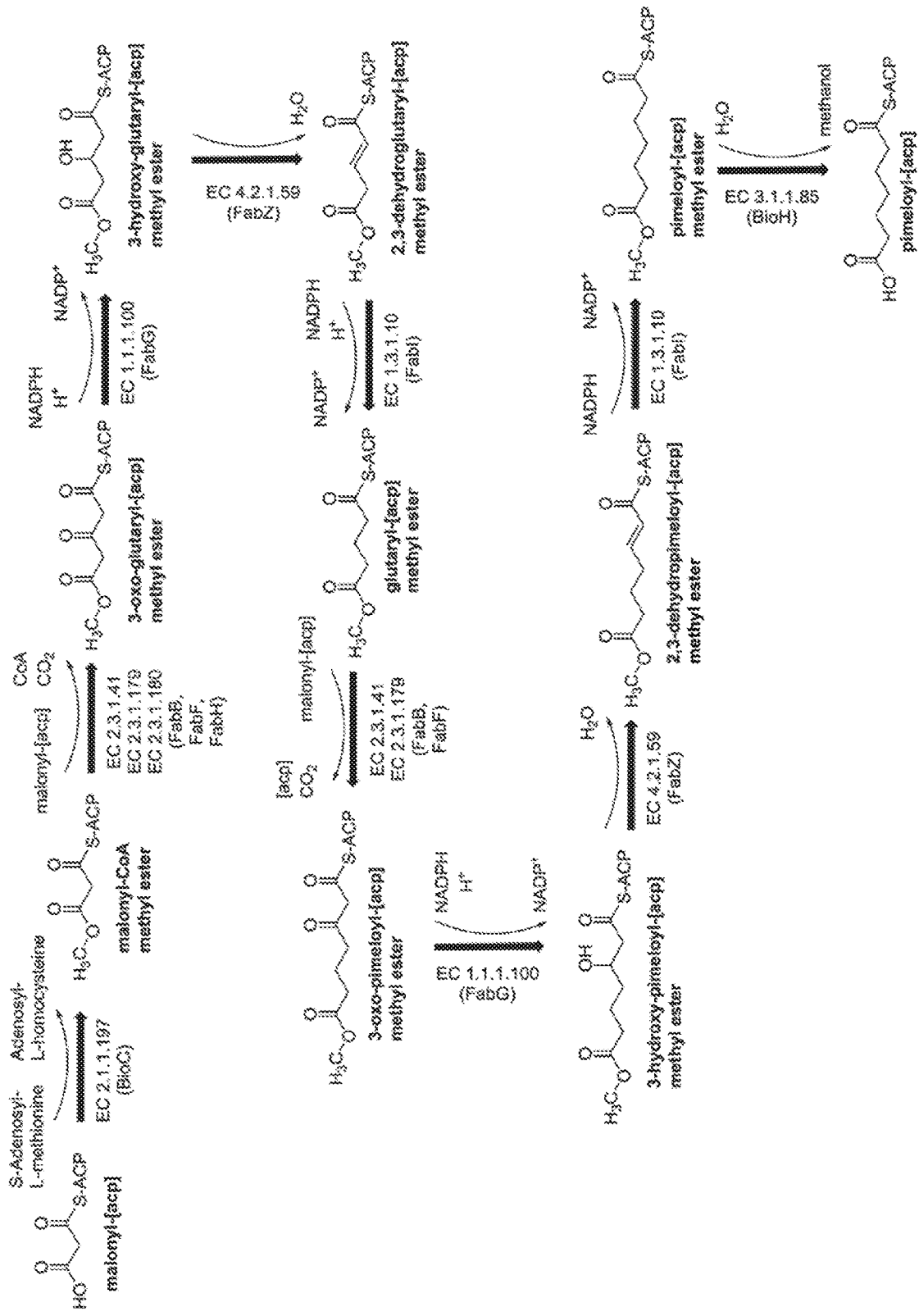
FIG. 1A is a schematic of an exemplary biochemical pathway leading to pimeloyl-ACP using NADPH-dependent enzymes and malonyl-ACP as a central precursor.

The following detailed description and examples illustrate certain embodiments of the present disclosure. Those of skill in the art will recognize that there are numerous variations and modifications of this disclosure that are encompassed by its scope. Accordingly, the description of certain embodiments should not be deemed as limiting.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

This disclosure provides enzymes, non-natural pathways, cultivation strategies, feedstocks, host microorganisms and attenuations to the host's biochemical network, which generates a seven carbon chain aliphatic backbone from central precursors in which two terminal functional groups may be formed leading to the synthesis of pimelic acid, 7-aminoheptanoic acid (7-AHA), heptamethylenediamine or 1,7-heptanediol (referred to as "C7 building blocks" herein). As used herein, the term "central precursor" is used to denote any precursor or metabolite leading to the synthesis of a final product, such as, for example, a c C7 building block. The term "central metabolite" is used herein to denote a metabolite that is produced in all microorganisms to support growth.

The reactions of the pathways described herein can be performed in one or more cell (e.g., host cell) strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from any of the above types of host cells and used in a purified or semi-purified form. Extracted enzymes can optionally be immobilized to a solid substrate such as the floors and/or walls of appropriate reaction vessels. Moreover, such extracts include lysates (e.g., cell lysates) that can be used as sources of relevant enzymes. In the methods provided by the disclosure, all the steps can be performed in cells (e.g., host cells), all the steps can be performed using extracted enzymes, or some of the steps can be performed in cells and others can be performed using extracted enzymes.

Host microorganisms described herein can include endogenous pathways that can be manipulated such that one or more C7 building blocks can be produced. Host microorganisms can also include endogenous pathways that can be manipulated to regulate the biosynthesis of one or more C7 building blocks. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

As used herein, a "bio-based product" is a product in which both the feedstock (e.g., sugars from sugar cane, corn, wood; biomass; waste streams from agricultural processes) and the conversion process to the product are biologically based (e.g., fermentation/enzymatic transformation involving a biological host/organism/enzyme). As used herein, a "bio-derived product" is a product in which one of the feedstocks (e.g., sugars from sugar cane, corn, wood; biomass; waste streams from agricultural processes) or the conversion process to the product is biologically based (e.g., fermentation/enzymatic transformation involving a biological host/organism/enzyme).

As used herein, a "fermentation-derived product" is a product produced by fermentation involving a biological host or organism.

The term "C7 building block" is used to denote a seven (7) carbon chain aliphatic backbone.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) or a protein and a host refers to a nucleic acid or protein that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host in addition to a malonyl-ACP O-methyltransferase and a pimeloyl-ACP methyl ester methylesterase: a β-ketoacyl-ACP synthase; a β-ketothiolase; a 3-oxoacyl-ACP reductase; acetoacetyl-CoA reductase; a 3-hydroxyacyl-CoA dehydrogenase; a 3-hydroxybutyryl-CoA dehydrogenase; an enoyl-CoA hydratase; 3-hydroxyacyl-ACP dehydratase; an enoyl-ACP reductase; a trans-2-enoyl-CoA reductase; a thioesterase; a reversible CoA ligase; a CoA-transferase; an acetylating aldehyde dehydrogenase; a 6-oxohexanoate dehydrogenase; a 7-oxoheptanoate dehydrogenase; an aldehyde dehydrogenase; a carboxylate reductase; a ω-transaminase; a N-acetyltransferase; an alcohol dehydrogenase; a deacetylase; a 6-hydroxyhexanoate dehydrogenase; a 5-hydroxypentanoate dehydrogenase; a 4-hydroxybutyrate dehydrogenase; a formate-tetrahydrofolate ligase; a S-(hydroxymethyl) glutathione dehydrogenase; or a 5-formylglutathione hydrolase. In recombinant hosts expressing a carboxylate reductase, a phosphopantetheinyl transferase also can be expressed as it enhances activity of the carboxylate reductase.

For example, a recombinant host can include at least one exogenous nucleic acid encoding at least one polypeptide having the activity of: (i) a malonyl-ACP O-methyltransferase, (ii) a β-ketoacyl-ACP synthase or a β-ketothiolase, (iii) a 3-oxoacyl-ACP reductase, acetoacetyl-CoA reductase, a 3-hydroxyacyl-CoA dehydrogenase, or a 3-hydroxybutyryl-CoA dehydrogenase, (iv) an enoyl-CoA hydratase or 3-hydroxyacyl-ACP dehydratase, (v) an enoyl-ACP reductase or a trans-2-enoyl-CoA reductase and produce pimeloyl-ACP or pimeloyl-CoA.

For example, a recombinant host, or non-naturally occurring organism, can include at least one exogenous nucleic acid encoding at least one polypeptide having the activity of at least one enzyme depicted in any of FIGS. 1 to 11. For example, the organism can include at least one exogenous nucleic acid encoding at least one polypeptide having the activity of an alcohol dehydrogenase, a formate-tetrahydrofolate ligase, a S-(hydroxymethyl) glutathione dehydrogenase, or a S-formylglutathione hydrolase. See, e.g., FIGS. 8-11.

Such recombinant hosts producing pimeloyl-ACP or pimeloyl-CoA further can include at least one exogenous nucleic acid encoding at least one polypeptide having the activity of a thioesterase, an aldehyde dehydrogenase, a 7-oxoheptanoate dehydrogenase, a 6-oxohexanoate dehydrogenase, a glutaconate CoA-transferase, a reversible succinyl-CoA ligase, an acetylating aldehyde dehydrogenase, or a carboxylate reductase and produce pimelic acid or pimelate semialdehyde. For example, a recombinant host producing pimeloyl-ACP or pimeloyl-CoA further can include a thioesterase, a reversible Co-ligase (e.g., a reversible succinyl-CoA ligase), or a CoA transferase (e.g., a glutaconate CoA-transferase) and produce pimelic acid. For example, a recombinant host producing pimeloyl-CoA further can include an acetylating aldehyde dehydrogenase and produce pimelate semialdehyde. For example, a recombinant host producing pimelate further can include a carboxylate reductase and produce pimelate semialdehyde.

A recombinant host producing pimelate semialdehyde further can include at least one exogenous nucleic acid encoding at least one polypeptide having the activity of a ω-transaminase and produce 7-aminoheptanoate. In some embodiments, a recombinant host producing pimeloyl-CoA includes a carboxylate reductase and a ω-transaminase to produce 7-aminoheptanoate.

A recombinant host producing pimelate or pimelate semialdehyde further can include at least one exogenous nucleic acid encoding at least one polypeptide having the activity of a 6-hydroxyhexanoate dehydrogenase, a 5-hydroxypentanoate dehydrogenase, or a 4-hydroxybutyrate dehydrogenase, and produce 7-hydroxyheptanoic acid. In some embodiments, a recombinant host producing pimeloyl-CoA includes an acetylating aldehyde dehydrogenase and a 6-hydroxyhexanoate dehydrogenase, a 5-hydroxypentanoate dehydrogenase, or a 4-hydroxybutyrate dehydrogenase to produce 7-hydroxyheptanoate. In some embodiments, a recombinant host producing pimelate includes a carboxylate reductase and a 6-hydroxyhexanoate dehydrogenase, a 5-hydroxypentanoate dehydrogenase, or a 4-hydroxybutyrate dehydrogenase to produce 7-hydroxyheptanoate.

A recombinant host producing 7-aminoheptanoate, 7-hydroxyheptanoate, or pimelate semialdehyde further can include at least one exogenous nucleic acid encoding at least one polypeptide having the activity of a ω-transaminase, a deacetylase, a N-acetyltransferase, or an alcohol dehydrogenase, and produce heptamethylenediamine. For example, a recombinant host producing 7-hydroxyheptanoate can include a carboxylate reductase with an optional phosphopantetheine transferase enhancer, a ω-transaminase, and an alcohol dehydrogenase.

Within an engineered pathway, the enzymes can be from a single source, i.e., from one species, or can be from multiple sources, i.e., different species. Nucleic acids encoding the enzymes described herein have been identified from various organisms and are readily available in publicly available databases such as GenBank or EMBL.

In some embodiments, the host microorganism's endogenous biochemical network is attenuated or augmented to (1) ensure the intracellular availability of acetyl-CoA and malonyl-CoA, (2) create an NAD+ imbalance that may only be balanced via the formation of a C7 building block, (3) prevent degradation of central metabolites and/or central precursors leading to and including C7 building blocks, (4) ensure efficient efflux from the cell, and/or (5) channel increased flux through the pathway leading to the C7 building block product(s).

Channeling Increased Flux Through C7 Building Block Biosynthesis Pathways

Figure 7:
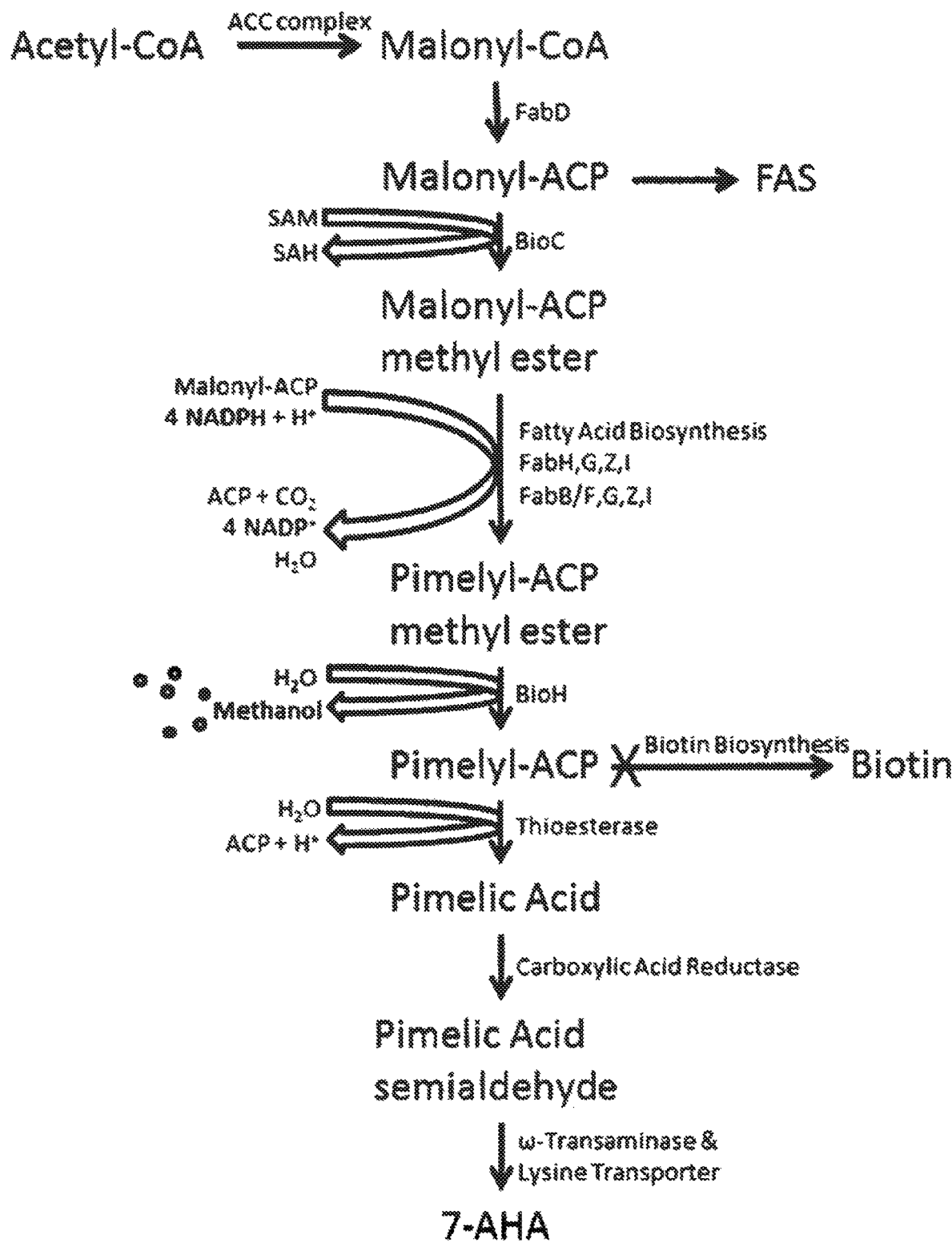
FIG. 7 shows a simplified schematic of an exemplary biochemical pathway for producing 7-AHA (7-AHA pathway) from the central carbon intermediate acetyl-CoA via the biotin metabolism pathway branching out from classic fatty acid metabolism.

An exemplary pathway (7-AHA pathway) for producing 7-AHA, a C7 building block, is depicted in FIG. 7. The 7-AHA pathway produces 7-AHA from the central carbon metabolism intermediate acetyl-CoA via the biotin synthesis pathway. The 7-AHA pathway branches out from the biotin pathway at the common intermediate pimelyl-ACP. BioH removes the methyl group of pimelyl-ACP methyl ester, producing pimelyl-ACP. The byproduct of this reaction is methanol, which is excreted by the host microorganism.

Metabolism can often be seen to be resistant to stimulating biosynthesis by expressing or over-expressing pathway enzymes. Control of the flux soon passes elsewhere, and metabolite concentrations rise. A classic metabolic engineering strategy to mitigate this risk is to exploit the natural homeostatic mechanisms of the cell: pull the products out, rather than push precursors toward them. The metabolic network will tend to replace the material that is removed. Feedback loops in the metabolism transfer control from the 'supply' steps near the beginning to the 'demand' reactions after the feedback loop.

Figure 10A:
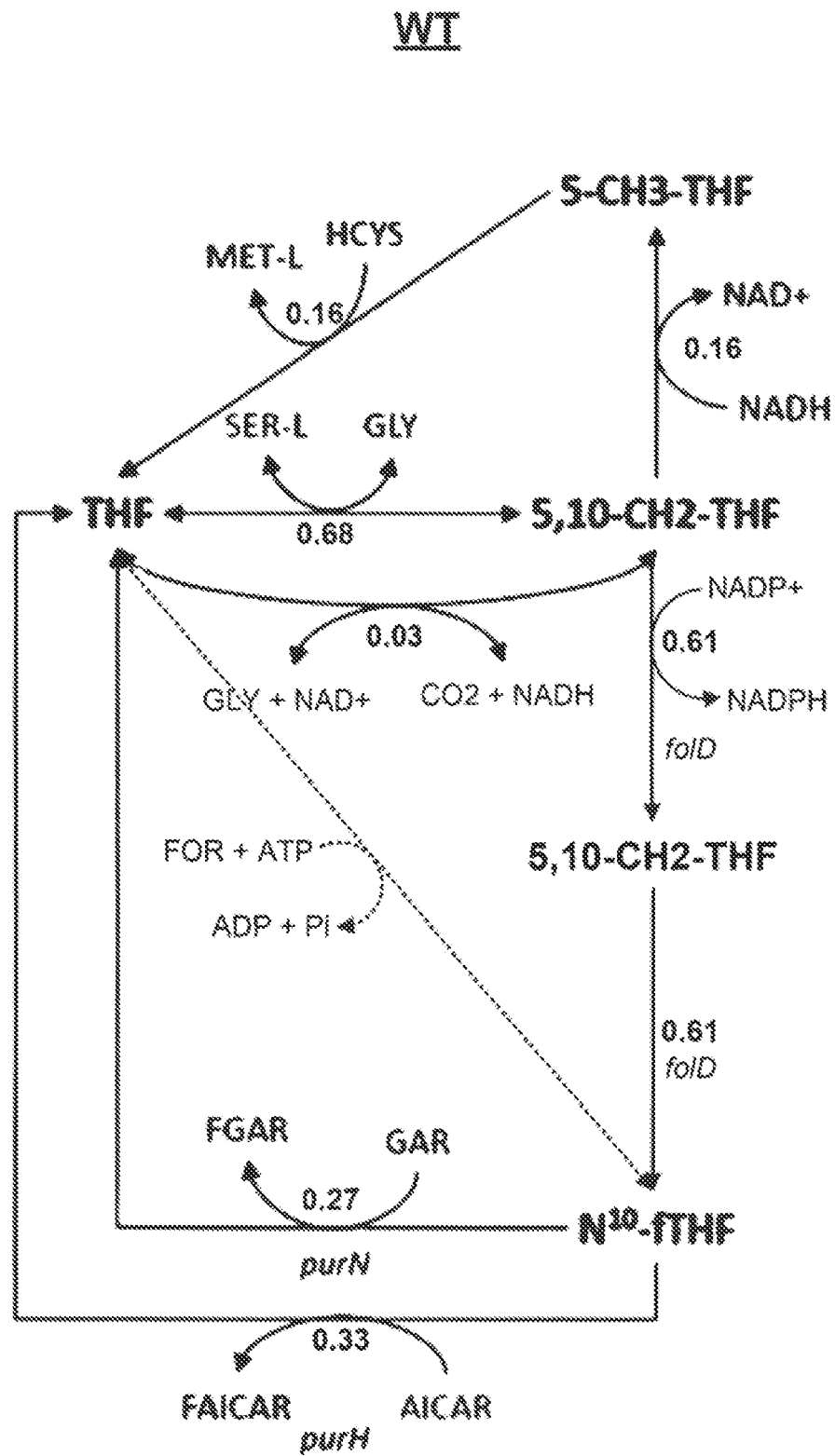
FIG. 10A shows a schematic of the wild type (WT) tetrahydrofolate metabolic cycle (THF-MC). FolD converts 5,10-methylenetetrahydrofolate (5,10-CH2-THF) to $N^{10}$-formyl tetrahydrofolate ($N^{10}$-fTHF). $N^{10}$-fTHF is a precursor in the pathway of purine nucleotide biosynthesis and formylation of the initiator tRNA.

A promising strategy to achieve this 'flux pulling' mechanism is to couple the growth of the cell to the formation of a growth critical intermediate produced as part of the biosynthetic pathway. In most cases, this ties growth to yield, titre, and productivity, thus regulating the biosynthesis of the product. This can be achieved by linking the byproduct of methanol, through formate, to the protein synthesis machinery through the tetrahydrofolate metabolic cycle (THF-MC), or a modified THF-MC, and hence growth of the microorganism host. A schematic of the wild-type THF-MC is shown in FIG. 10A.

Work by Sah et al. (Sah et al., *J. Bacteriol.*, 2015, 197(4), 717-726) investigated the physiological and functional importance of FolD and formyltetrahydrofolate synthetase (Fhs) in the THF-MC. As noted by Sah et al., the enzymes that catalyse interconversions of the above pathway intermediates are highly conserved across the three domains of life (Smith et al., *J. Bacteriol.*, 200, 50, 43-53; Bult et al., *Science*, 1996, 273, 1058-1073; Slesarev et al., *Proc. Natl. Acad. Sci. USA*, 2002, 99, 4644-4649; Buchenau et al., *Arch. Microbiol.*, 2004, 182, 313-325; Maeder et al., *J. Bacteriol.*, 2006, 188, 7922-7931). While serine hydroxymethyltransferase (GlyA) catalyses the reversible reaction of conversion of serine and THF to glycine and 5,10-methylene-tetrahydrofolate (5,10-CH2-THF), FolD carries out the conversion of 5,10-methenyltetrahydrofolate (5,10-CH1-THF) to $N^{10}$-formyltetrahydrofolate ($N^{10}$-fTHF) (see FIG. 10A). $N^{10}$-fTHF is important for the de novo pathway of purine nucleotide biosynthesis and formylation of the initiator tRNA (tRNAfMet) to initiate protein synthesis in eubacteria and eukaryotic organelles (Pino et al., *Mol. Microbiol.*, 2010, 76, 706-718). Another enzyme, Fhs, can also synthesize $N^{10}$-fTHF by utilizing THF, formate, and ATP. The dual scheme of $N^{10}$-fTHF synthesis is conserved in eukaryotes and some archaea (Maeder et al., *J. Bacteriol.*, 2006, 188, 7922-7931).

Many eukaryotic organisms possess FolD (Pino et al., *Mol. Microbiol.*, 2010, 76, 706-718; Paukert et al., *J. Biol. Chem.*, 1976, 251, 5104-5111). Amongst eubacteria, all organisms possess FolD, but some possess both FolD and Fhs (Paukert et al., *Biochem. Biophys. Res. Commun.*, 1977, 77, 147-154). The advantage of possessing Fhs in addition to FolD was demonstrated by Sah et al. (Sah et al., *J. Bacteriol.*, 2015, 197(4), 717-726). In the presence of formate and in anaerobic conditions of growth, predominant synthesis of $N^{10}$-fTHF may occur via Fhs. In an fhs-supported *E. coli* folD deletion (ΔfolD+fhs) model, the enzyme 2-ketobutyrate formate-lyase/pyruvate formate-lyase (pflBtdcE) can produce $N^{10}$-fTHF in the presence of formate (see FIG. 10B). $N^{10}$-fTHF may then be converted to the other one-carbon metabolism intermediates (Whitehead et al., *J. Bacteriol.*, 1988, 170, 9995-997).

Figure 10B:
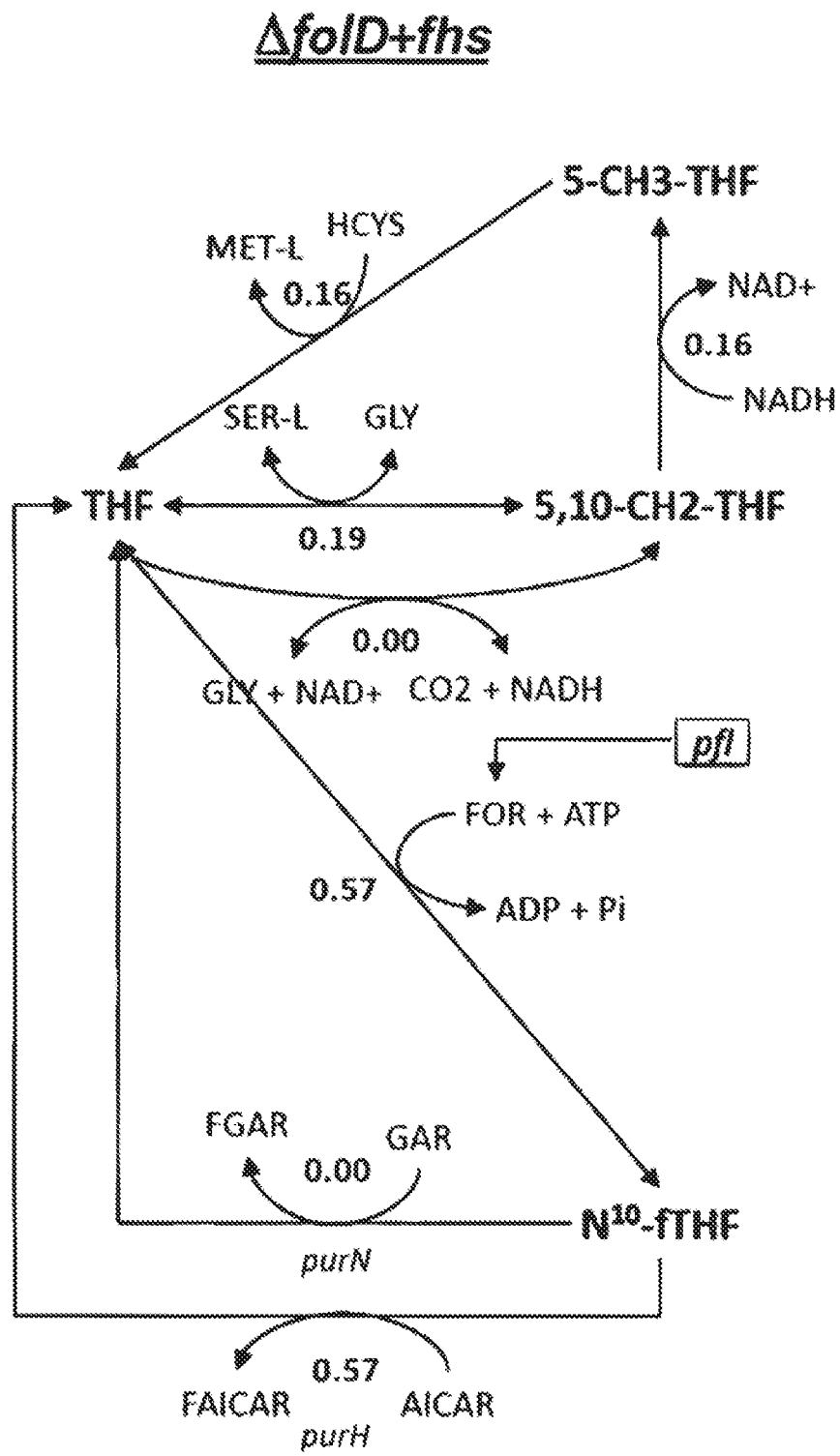
FIG. 10B shows a schematic of a modified THF-MC where folD is eliminated and a formate-tetrahydrofolate ligase (fhs) is inserted. In this modified cycle folD function is replaced by fhs.
Figure 11:
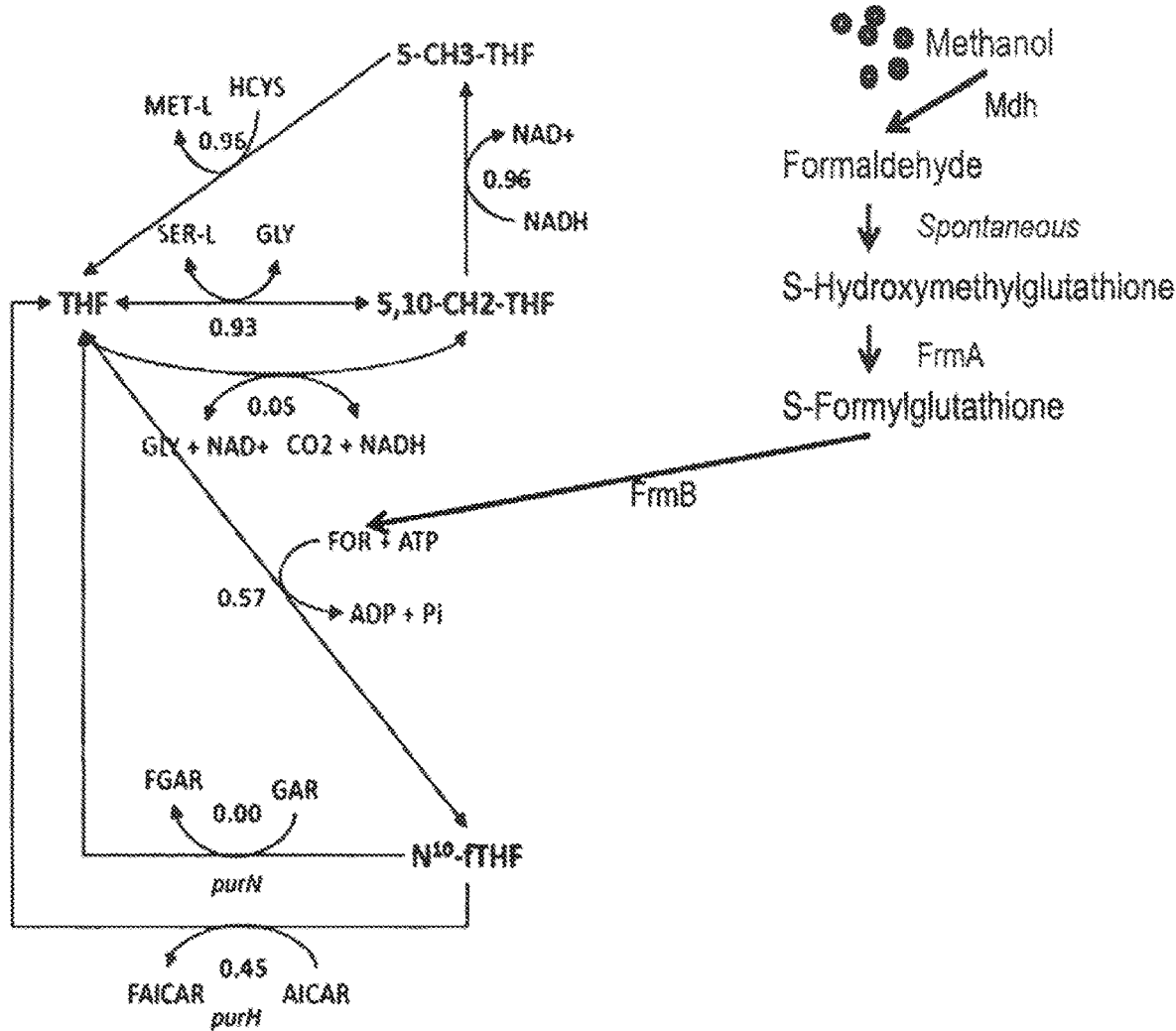
FIG. 11 shows a schematic of a modified THF-MC where folD function is replaced by a formate-tetrahydrofolate ligase (fhs) and formate acetyltransferase (pflB) and PFL-like enzyme TdcE (tdcE) are deleted, eliminating the source of formate. Introduction of a S-(hydroxymethyl) glutathione dehydrogenase (frmA) and a S-formylglutathione hydrolase (frmB) enables conversion of formaldehyde into formate.

According to this disclosure, when folD is knocked out and fhs is knocked in or expressed from an exogenously-derived nucleic acid, the microorganism strain should be able to grow after the redirection of the methanol oxidation into the modified THF-MC pathway as the former will act as a source of formate (FIG. 10B). Methanol will therefore become a growth critical intermediate by making it necessary for the synthesis of purine nucleotides, thymidylate, and initiator tRNAs. Accordingly, the cells reliant on methanol will revert to the production of more methanol, thereby pulling flux down the 7-AHA pathway and leading to high 7-AHA yield, titre, and productivity.

The described system may lead to increased yield, titre, and productivity through multiple modes. The described system mitigates the risk of carbon wastage in the system, which results in lower yield. By utilizing the carbon from the methanol byproduct of the BioH enzyme in the 7-AHA pathway, the described system reduces carbon wastage from typical methanol efflux. The described system may also mitigate risk of potential methanol toxicity. Therefore, since the host is dependent on methanol for growth, the accumulation of methanol, which is potentially deleterious to host viability, is decreased. Thus, decreasing methanol accumulation may also mitigate the risk of low 7-AHA yield. Furthermore, the described system may reduce production costs by mitigating the need for methanol removal during downstream processing of the product. As such, the described system has a potential improvement of about 15 to about 22% of the maximum theoretical yield in 7-AHA production, for example.

Thus, by increasing flux through the C7 building block biosynthesis pathway (e.g., the 7-AHA pathway) by requiring methanol for host growth, the biosynthesis of C7 building blocks is regulated.

The attenuation of certain enzymes may contribute to the regulation of biosynthesis of C7 building blocks. For example, a host may have attenuation of a biofunctional protein, classified, for example, under EC 1.5.1.5 and/or under EC 3.5.4.9. For example, and as described above, a host microorganism may have deletion, or knock out, of a bifunctional protein FolD (folD) (see UniProt Accession No. P24186, SEQ ID NO: 32; UniProt Accession No. B7LJI7, SEQ ID NO: 33; UniProt Accession No. Q32JK7, SEQ ID NO: 34).

A host microorganism may also have attenuation of a formate acetyltransferase and/or a pyruvate formate-lyase (PFL)-like enzyme, both of which may be classified under, for example, EC 2.3.1.54. For example, the host may have a deletion, or knock out, of formate acetyltransferase 1 (pflB) (see UniProt Accession No. P09373, SEQ ID NO: 35) and PFL-like enzyme TdcE (tdcE) (see UniProt Accession No. P42632, SEQ ID NO: 36). Formate acetyltransferase 1 synthesizes formate from pyruvate, and PFL-like enzyme TdcE catalyzes the cleavage of 2-ketobutyrate to propionyl-CoA and formate. By removing these two genes, the source of formate is removed. See FIGS. 10B and 11.

The host organism may also express one or more genes encoded in one or more exogenous nucleic acids, or genes may be knocked in to the host organism. For example, as described above, a host organism may express a formyltetrahydrofolate synthetase (Fhs), which is interchangeably referred to as a formate-tetrahydrofolate ligase (Fths), and is classified under, for example, EC 6.3.4.3. For example, the host may express one or more Fhs proteins set forth in SEQ ID NOs: 18-22 (see UniProt Accession Nos. Q07064, A8MIN1, P131419, Q5XZD9, and Q251P8, respectively). A formylletrahydrofolate synthetase may be knocked in or expressed from an exogenously-derived nucleic acid.

The host organism may also express an alcohol dehydrogenase (Adh), classified under, for example, EC 1.1.1.-, from one or more exogenous nucleic acids, or the alcohol dehydrogenase may be knocked in to the host organism. For example, the alcohol dehydrogenase may be a methanol dehydrogenase (Mdh), classified under, for example, EC 1.1.1.37. For example, the host may express an alcohol dehydrogenase as set forth in SEQ ID NO: 31 (see UniProt Accession No. Q46856). An alcohol dehydrogenase may then catalyze the conversion of methanol to formaldehyde. Formaldehyde can then be oxidized into formate. See FIG. 11.

To aid in oxidation of formaldehyde to formate, the host cell may express a S-(hydroxymethyl) glutathione dehydrogenase (e.g., FrmA), classified under, for example, EC 1.1.1.284, and/or a S-formylglutathione hydrolase (e.g., FrmB), classified under, for example, EC 3.1.2.12, from one or more exogenous nucleic acids, or may be knocked in to the host organism. For example, a host may express a FrmA protein as set forth in SEQ ID NOs: 23-26 (see UniProt Accession Nos. P25437, Q3Z550, A0A0M7MPD4, and W1AV69, respectively) and/or a FrmB protein as set forth in SEQ ID NOs: 27-30 (see UniProt Accession Nos. P51025, Q3Z551, A0A0M9J3Q3, and W1ATJ0, respectively). After formaldehyde spontaneously converts to H-hydroxymethyl-glutathione, S-(hydroxymethyl) glutathione dehydrogenase converts H-hydroxymethylglutathione to S-formylglutathione. S-formylglutathione hydrolase then converts S-formylglutathione to formate. See FIG. 11.

The described system may also lead to using methanol for cell growth. As described above, the modified THF-MC pathway requires methanol as described above, the engineered pathway requires methanol for the synthesis of purine nucleotides, thymidylate, and initiator tRNAs. As such, in this system, methanol is required for cell growth. As such, in the described system, cell growth is reliant on methanol.

Enzymes

Any of the enzymes described herein that can be used for production of one or more C7 building blocks, or in the regulation of the biosynthesis of C7 building blocks, can have at least 50%, at least 60%, or at least 70% sequence identity or homology (e.g., at least 75%, at least 80%, at least 85%, at least 90%, at least 95%, at least 97%, at least 98%, at least 99%, or 100%) to the amino acid sequence of the corresponding wild-type enzyme. It will be appreciated that the sequence identity can be determined on the basis of the mature enzyme (e.g., with any signal sequence removed).

A polypeptide having a certain percent (e.g., at least 75%, at least 80%, at least 85%, at least 90%, at least 95%, at least 97%, at least 98%, at least 99%, or 100%) of sequence identity with another sequence means that, when aligned, that percentage of bases or amino acid residues are the same in comparing the two sequences.

The percent identity and homology between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from the U.S. government's National Center for Biotechnology Information web site (ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows:—i is set to a file containing the first amino acid sequence to be compared (e.g., C:\seq1.txt); —j is set to a file containing the second amino acid sequence to be compared (e.g., C:\seq2.txt); —p is set to blastp; —o is set to any desired file name (e.g., C:\output.txt); and all other options are left at their default setting. For example, the following command can be used to generate an output file containing a comparison between two amino acid sequences: C: \Bl2seq—i c:\seq1.txt—j c:\seq2.txt—p blastp—o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity is determined by dividing the number of matches by the length of the full-length polypeptide amino acid sequence followed by multiplying the resulting value by 100. It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution and this process results in "sequence homology" of, e.g., at least 75%, at least 80%, at least 85%, at least 90%, at least 91%, at least 92%, at least 93%, at least 94%, at least 95%, at least 96%, at least 97%, at least 98%, or at least 99%. Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer. Applic. Biol. Sci.,* 1988, 4, 11-17, e.g., as implemented in the program PC/GENE (Intelligenetics, Mountain View, Calif., USA). This alignment and the percent homology or identity can be determined using any suitable software program known in the art, for example those described in CURRENT PROTOCOLS IN MOLECULAR BIOLOGY (F. M. Ausubel et al. (eds.) 1987, Supplement 30, section 7.7.18). Such programs may include the GCG Pileup program, FASTA (Pearson et al., *Proc. Natl. Acad. Sci. USA,* 1988, 85, 2444-2448), and BLAST (BLAST Manual, Altschul et al., Nat'l Cent. Biotechnol. Inf., Nat'l Lib. Med. (NCIB NLM NIH), Bethesda, Md., and Altschul et al., *NAR,* 1997, 25, 3389-3402). Another alignment program is ALIGN Plus (Scientific and Educational Software, Pa.), using default parameters. Another sequence software program that finds use is the TFASTA Data Searching Program available in the Sequence Software Package Version 6.0 (Genetics Computer Group, University of Wisconsin, Madison, Wis.).

A conservative substitution is a substitution of one amino acid for another with similar characteristics. Conservative substitutions include substitutions within the following groups: valine, alanine, and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Any substitution of one member of the above-mentioned polar, basic, or acidic groups by another member of the same group can be deemed a conservative substitution. By contrast, a non-conservative substitution is a substitution of one amino acid for another with dissimilar characteristics.

For example, a thioesterase described herein can have at least 70% sequence identity or homology (e.g., at least 75%, at least 80%, at least 85%, at least 90%, at least 95%, at least 97%, at least 98%, at least 99%, or 100%) to the amino acid sequence of an *Escherichia coli* thioesterase encoded by tesB (see GenBank Accession No. AAA24665.1, SEQ ID NO: 1).

For example, a carboxylate reductase described herein can have at least 70% sequence identity or homology (e.g., at least 75%, at least 80%, at least 85%, at least 90%, at least 95%, at least 97%, at least 98%, at least 99%, or 100%) to the amino acid sequence of a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium smegmatis* (see Genbank Accession No. ABK75684.1, SEQ ID NO: 5), a *Mycobacterium massiliense* (see Genbank Accession No. EIV11143.1, SEQ ID NO: 6), or a *Segniliparus rotundus* (see Genbank Accession No. ADG98140.1, SEQ ID NO: 7) carboxylate reductase.

For example, a ω-transaminase described herein can have at least 70% sequence identity or homology (e.g., at least 75%, at least 80%, at least 85%, at least 90%, at least 95%, at least 97%, at least 98%, at least 99%, or 100%) to the amino acid sequence of a *Chromobacterium violaceum* (see Genbank Accession No. AAQ59697.1, SEQ ID NO: 8), a *Pseudomonas aeruginosa* (see Genbank Accession No. AAG08191.1, SEQ ID NO: 9), a *Pseudomonas syringae* (see Genbank Accession No. AAY39893.1, SEQ ID NO: 10), a *Rhodobacter sphaeroides* (see Genbank Accession No. ABA81135.1, SEQ ID NO: 11), an *Escherichia coli* (see RefSeq Accession No. NP_417544.5, SEQ ID NO: 12), or a *Vibrio fluvialis* (see Genbank Accession No. AEA39183.1, SEQ ID NO: 13) ω-transaminase. Some of these ω-transaminases are diamine ω-transaminases.

For example, a phosphopantetheinyl transferase described herein can have at least 70% sequence identity or homology (e.g., at least 75%, 80%, 85%, 90%, 95%, 97%, 98%, 99%, or 100%) to the amino acid sequence of a *Bacillus subtilis* phosphopantetheinyl transferase (see RefSeq Accession No. WP_003234549.1, SEQ ID NO: 14) or a *Nocardia* sp. NRRL 5646 phosphopantetheinyl transferase (see Genbank Accession No. ABI83656.1, SEQ ID NO: 15).

For example, a malonyl-CoA methyltransferase described herein can have at least 70% sequence identity or homology (e.g., at least 75%, 80%, 85%, 90%, 95%, 97%, 98%, 99%, or 100%) to the amino acid sequence of a *Bacillus cereus* malonyl-CoA methyltransferase (see GenBank Accession No. AAS43086.1, SEQ ID NO: 16).

For example, a pimeloyl-ACP methyl ester esterase described herein can have at least 70% sequence identity or homology (e.g., at least 75%, 80%, 85%, 90%, 95%, 97%, 98%, 99%, or 100%) to the amino acid sequence of an *Escherichia coli* pimeloyl-ACP methyl ester esterase (see GenBank Accession No. AAC76437.1, SEQ ID NO: 17).

For example, a formate-tetrahydrofolate ligase described herein can have at least 70% sequence identity or homology (e.g., at least 75%, at least 80%, at least 85%, at least 90%, at least 95%, at least 97%, at least 98%, at least 99%, or 100%) to the amino acid sequence of a *Clostridium cylindrosporum* (see UniProt Accession No. Q07064, SEQ ID NO: 18), an *Alkaliphilus oremlandii* (see UniProt Accession No. A8MIN1, SEQ ID NO: 19), a *Clostridium acidurici* (see UniProt Accession No. P13419, SEQ ID NO: 20), a *Eubacterium acidaminophilum* (see UniProt Accession No. Q5XZD9, SEQ ID NO: 21), or a *Desulfitobacterium hafniense* (see UniProt Accession No. Q251P8, SEQ ID NO: 22) formate-tetrahydrofolate ligase.

For example, a S-(hydroxymethyl) glutathione dehydrogenase described herein can have at least 70% sequence identity or homology (e.g., at least 75%, at least 80%, at least 85%, at least 90%, at least 95%, at least 97%, at least 98%, at least 99%, or 100%) to the amino acid sequence of a *Escherichia coli* (see UniProt Accession No. P25437, SEQ ID NO: 23), a *Shigella sonnei* (see UniProt Accession No. Q3Z550, SEQ ID NO: 24), an *Achromaobacter* sp. (see UniProt Accession No. A0A0M7MPD4, SEQ ID NO: 25), or a *Klebsiella pneumoniae* (see UniProt Accession No. W1AV69, SEQ ID NO: 26) S-(hydroxymethyl) glutathione dehydrogenase.

For example, a S-formylglutathione hydrolase described herein can have at least 70% sequence identity or homology (e.g., at least 75%, at least 80%, at least 85%, at least 90%, at least 95%, at least 97%, at least 98%, at least 99%, or 100%) to the amino acid sequence of an *Escherichia coli* (see UniProt Accession No. P51025, SEQ ID NO: 27), a *Shigella sonnei* (see UniProt Accession No. Q3Z551, SEQ ID NO: 28), an *Achromobacter* sp. (see UniProt Accession No. A0A0M9J3Q3, SEQ ID NO: 29), or a *Klebsiella pneumoniae* (see UniProt Accession No. W1ATJO, SEQ ID NO: 30) S-formylglutathione hydrolase.

For example, an alcohol dehydrogenase described herein can have at least 70% sequence identity or homology (e.g., at least 75%, at least 80%, at least 85%, at least 90%, at least 95%, at least 97%, at least 98%, at least 99%, or 100%) to the amino acid sequence of an *Escherichia coli* (see UniProt Accession No. Q46856, SEQ ID NO: 31) alcohol dehydrogenase.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacterium or fungus) is obtained, using appropriate codon bias tables for that species.

Functional fragments of any of the enzymes described herein can also be used in the methods of the disclosure. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This disclosure also provides (i) functional variants of the enzymes used in the methods of the disclosure and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine (SEQ ID NO: 37)), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a formate-tetrahydrofolate ligase, a S-(hydroxymethyl) glutathione dehydrogenase, a S-formylglutathione hydrolase, a methyltransferase, a synthase, β-ketothiolase, a dehydratase, a hydratase, a dehydrogenase, a methylesterase, a thioesterase, a reversible CoA-ligase, a CoA-transferase, a reductase, deacetylase, N-acetyltransferase or a ω-transaminase as described in more detail below.

For example, the polynucleotides encoding the described polypeptides, and variants thereof, with the respective enzymatic activity, can be incorporated in a nucleic acid construct or vector. In some embodiments, the polynucleotide is operably linked to one or more heterologous control sequences that direct production of the polypeptide.

In addition, the production of one or more C7 building blocks can be performed in vitro using the isolated enzymes described herein, using a lysate (e.g., a cell lysate) from a host microorganism as a source of the enzymes, or using a plurality of lysates from different host microorganisms as the source of the enzymes.

Figure 1B:
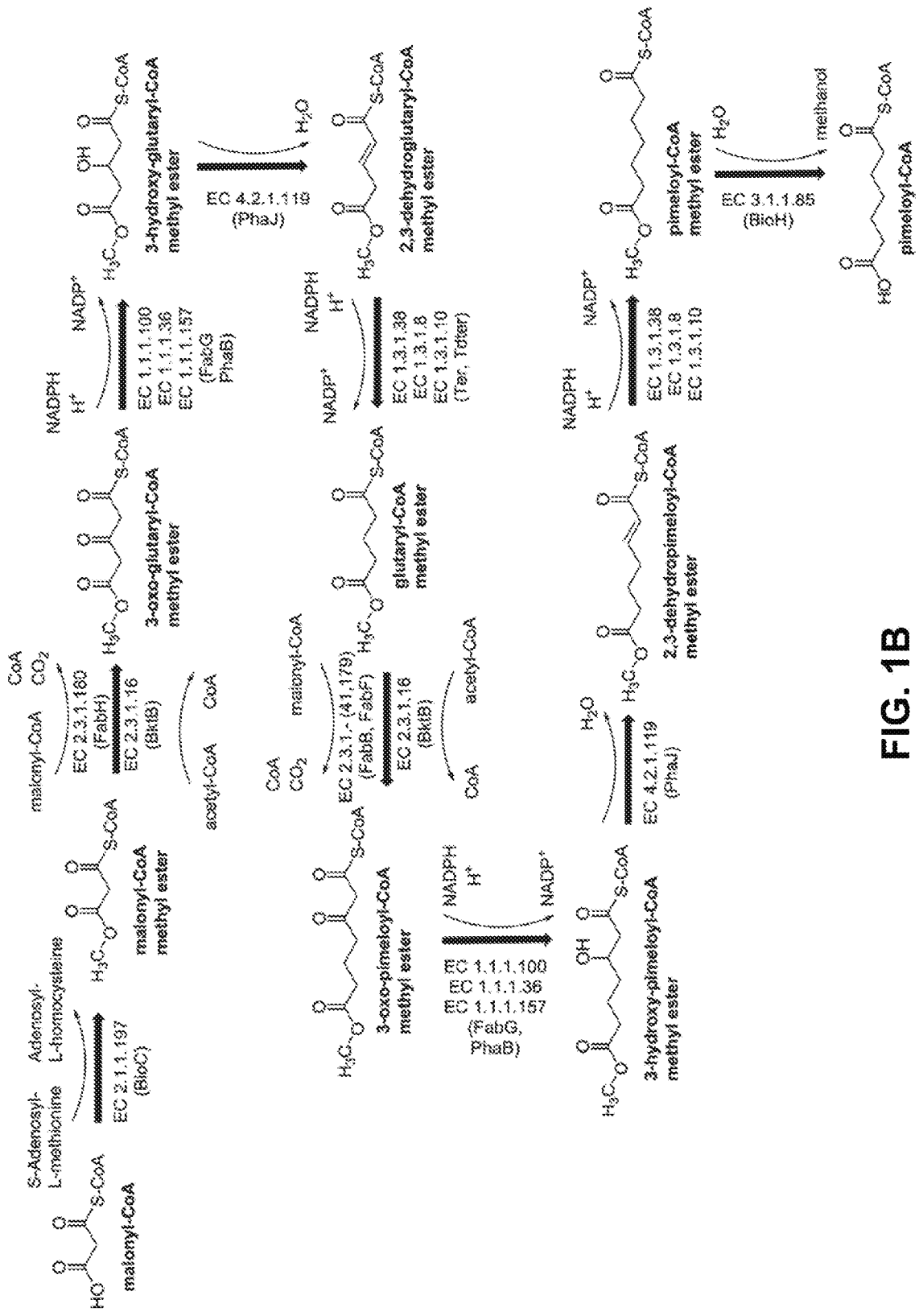
FIG. 1B is a schematic of an exemplary biochemical pathway leading to pimeloyl-CoA using NADPH-dependent enzymes and acetyl-CoA and malonyl-CoA as central precursors.
Figure 1C:
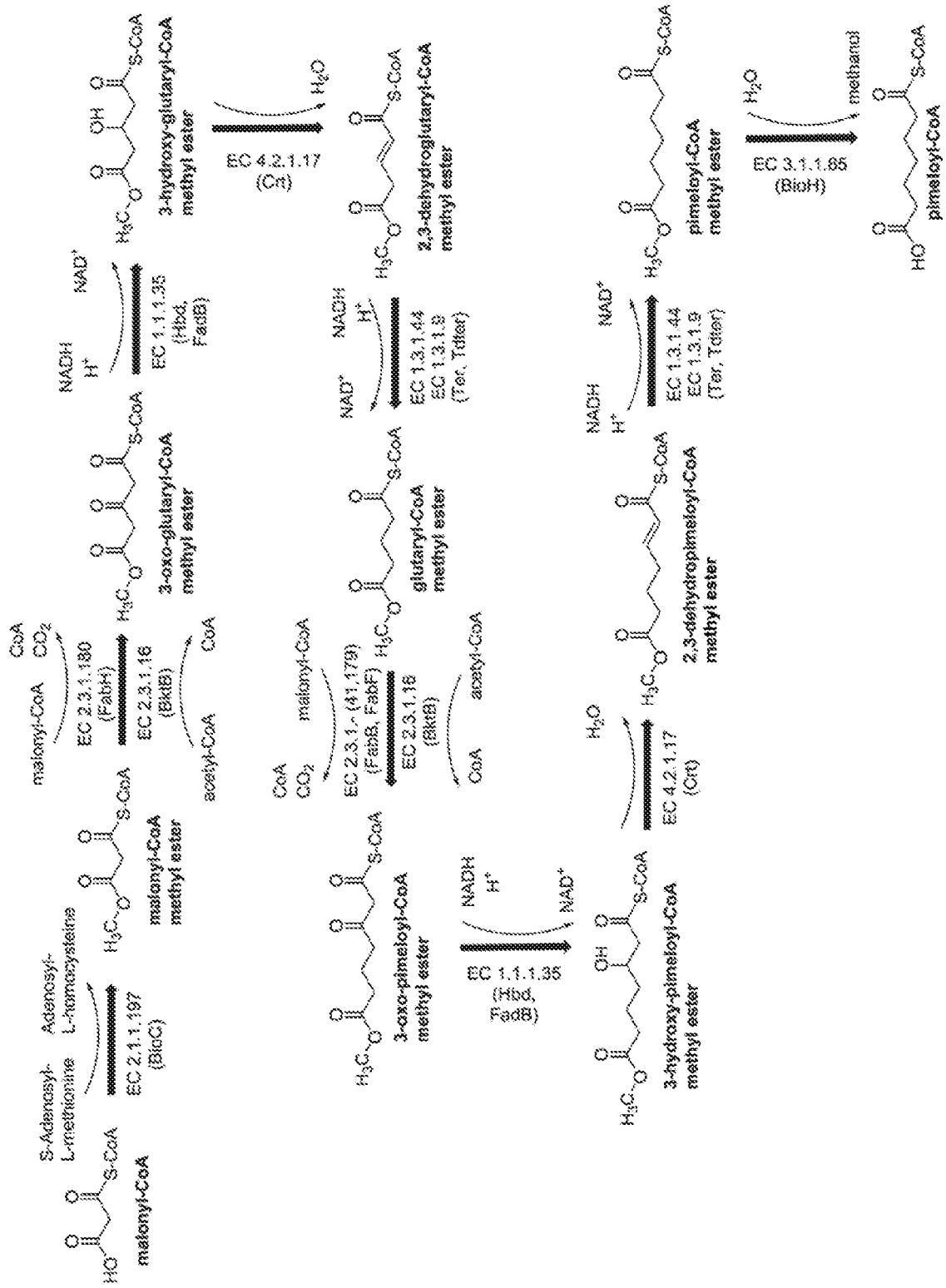
FIG. 1C is a schematic of an exemplary biochemical pathway leading to pimeloyl-CoA using NADH-dependent enzymes and acetyl-CoA and malonyl-CoA as central precursors.

Enzymes Generating the C7 Aliphatic Backbone for Conversion to C7 Building Blocks As depicted in FIG. 1A, FIG. 1B, and FIG. 1C, a C7 aliphatic backbone for conversion to one or more C7 building blocks can be formed from malonyl-ACP, or acetyl-CoA and malonyl-CoA, via two cycles of methyl-ester shielded carbon chain elongation associated with biotin synthesis using either NADH or NADPH dependent enzymes.

In some embodiments, a methyl ester shielded carbon chain elongation associated with biotin biosynthesis route comprises using a malonyl-ACP O-methyltransferase to form a malonyl-ACP methyl ester, and then performing two cycles of carbon chain elongation using a β-ketoacyl-ACP synthase, a 3-oxoacyl-ACP reductase, a 3-hydroxyacyl-ACP dehydratase, and an enoyl-ACP reductase. A pimeloyl-ACP methyl ester esterase can be used to cleave the resulting pimeloyl-ACP methyl ester.

In some embodiments, a methyl ester shielded carbon chain elongation route comprises using a malonyl-ACP O-methyltransferase to form a malonyl-CoA methyl ester, and then performing two cycles of carbon chain elongation using (i) a β-ketothiolase or a β-ketoacyl-ACP synthase, (ii) an acetoacetyl-CoA reductase, a 3-oxoacyl-ACP reductase, or a 3-hydroxybutyryl-CoA dehydrogenase, (iii) an enoyl-CoA hydratase, and (iv) a trans-2-enoyl-CoA reductase. A pimeloyl-ACP methyl ester esterase can be used to cleave the resulting pimeloyl-CoA methyl ester.

In some embodiments, a methyltransferase can be a malonyl-ACP O-methyltransferase classified, for example, under EC 2.1.1.197, such as, for example, the gene product of bioC from *Bacillus cereus* (see Genbank Accession No. AAS43086.1, SEQ ID NO: 16) (see, e.g., Lin, 2012, *Biotin Synthesis in Escherichia coli*, Ph.D. Dissertation, University of Illinois at Urbana-Champaign).

In some embodiments, a β-ketothiolase may be classified, for example, under EC 2.3.1.16, such as, for example, the gene product of bktB. The β-ketothiolase encoded by bktB from *Cupriavidus necator* accepts propanoyl-CoA and pentanoyl-CoA as substrates, forming the CoA-activated C7 aliphatic backbone (see, e.g., Haywood et al., *FEMS Microbiology Letters*, 1988, 52:91-96; Slater et al., *J. Bacteriol.*, 1998, 180(8):1979-1987).

In some embodiments, a β-ketoacyl-ACP synthase may be classified, for example, under EC 2.3.1.- (e.g., EC 2.3.1.41, EC 2.3.1.179, or EC 2.3.1.180), such as, for example, the gene product of fabB, fabF, or fabH.

In some embodiments, a 3-hydroxyacyl-CoA dehydrogenase may be classified, for example, under EC 1.1.1.35, such as, for example, the gene product of fadB, or classified under EC 1.1.1.157, such as, for example, the gene product of hbd (can be referred to as a 3-hydroxybutyryl-CoA dehydrogenase), or classified under EC 1.1.1.36, such as, for example, the gene product of phaB (see, e.g., Liu & Chen, *Appl. Microbiol. Biotechnol.*, 2007, 76(5), 1153-1159; Shen et al., *Appl. Environ. Microbiol.*, 2011, 77(9), 2905-2915; or Budde et al., *J. Bacteriol.*, 2010, 192(20), 5319-5328).

In some embodiments, a 3-oxoacyl-CoA reductase may be, for example, classified under EC 1.1.1.100, such as, for example, the gene product of fabG (Budde et al., 2010, supra; Nomura et al., *Appl. Environ. Microbiol.*, 2005, 71(8), 4297-4306).

In some embodiments, an enoyl-CoA hydratase may be classified, for example, under EC 4.2.1.17, such as the gene product of crt, or classified under EC 4.2.1.119, such as, for example, the gene product of phaJ (Shen et al., 2011, supra; or Fukui et al., *J. Bacteriol.*, 1998, 180(3), 667-673).

In some embodiments, an enoyl-ACP dehydratase such as a 3-hydroxyacyl-ACP dehydratase may be classified, for example, under EC 4.2.1.59, such as, for example, the gene product of fabZ.

In some embodiments, a trans-2-enoyl-CoA reductase may be classified, for example, under EC 1.3.1.- (e.g., EC 1.3.1.38, EC 1.3.1.8, EC 1.3.1.44), such as, for example, the gene product of ter (Nishimaki et al., *J. Biochem.*, 1984, 95, 1315-1321; Shen et al., 2011, supra) or tdter (Bond-Watts et al., *Biochemistry*, 2012, 51, 6827-6837).

In some embodiments, an enoyl-ACP reductase may be classified, for example, under EC 1.3.1.10, such as, for example, the gene product of fabL, or EC 1.3.1.9, such as, for example, the gene product of fabI.

In some embodiments, a pimeloyl-ACP methyl ester esterase may be classified, for example, under EC 3.1.1.85, such as, for example, the gene product of bioH from *E. coli*. See Genbank Accession No. AAC76437.1 (SEQ ID NO: 17).

Figure 2:
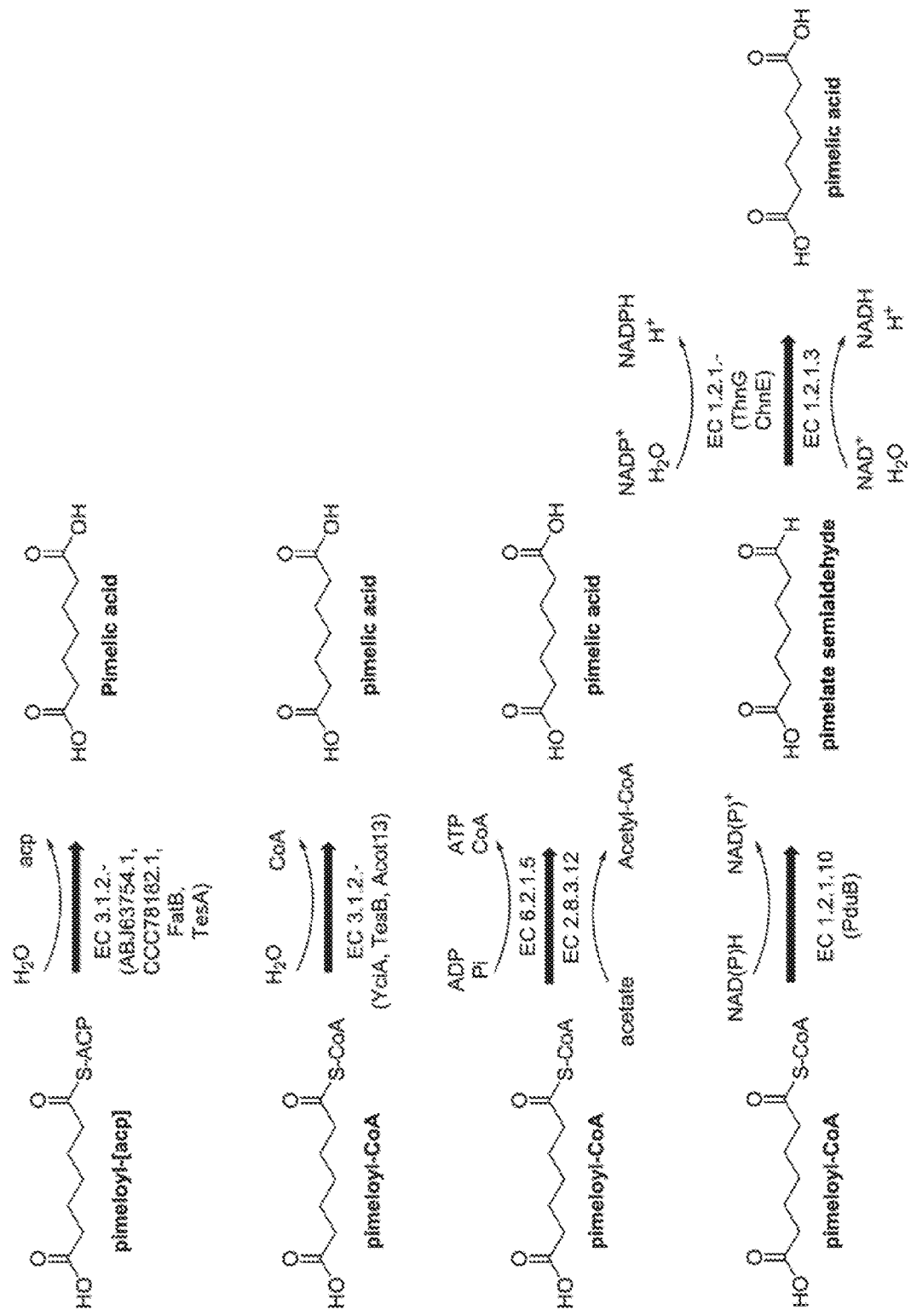
FIG. 2 is a schematic of exemplary biochemical pathways leading to pimelate using pimeloyl-ACP, pimeloyl-CoA, or pimelate semialdehyde as central precursors.

Enzymes Generating the Terminal Carboxyl Groups in the Biosynthesis of C7 Building Blocks As depicted in FIG. 2, a terminal carboxyl group can be enzymatically formed using a thioesterase, an aldehyde dehydrogenase, a 7-oxoheptanoate dehydrogenase, a 6-oxohexanoate dehydrogenase, a CoA-transferase, or a reversible CoA-ligase.

In some embodiments, the second terminal carboxyl group leading to the synthesis of a C7 building block is enzymatically formed by a thioesterase classified, for example, under EC 3.1.2.-, such as, for example, the gene product of yciA, tesB (Genbank Accession No. AAA24665.1, SEQ ID NO: 1) or acot13 (see, e.g., Cantu et al., *Protein Science*, 2010, 19, 1281-1295; Zhuang et al., *Biochemistry*, 2008, 47(9), 2789-2796; or Naggert et al., *J. Biol. Chem.*, 1991, 266(17), 11044-11050).

In some embodiments, the second terminal carboxyl group leading to the synthesis of a C7 building block is enzymatically formed by an acyl-ACP thioesterase classified, for example, under EC 3.1.2.-, such as, for example, the gene product of fatB or tesA. The acyl-ACP thioesterases encoded by Genbank Accession Nos. ABJ63754.1 and CCC78182.1 have C6-C8 chain length specificity (Jing et al., 2011, *BMC Biochemistry*, 12(44)).

In some embodiments, the second terminal carboxyl group leading to the synthesis of pimelic acid is enzymatically formed by an aldehyde dehydrogenase classified, for example, under EC 1.2.1.3 (see, for example, Guerrillot & Vandecasteele, *Eur. J. Biochem.*, 1977, 81, 185-192).

In some embodiments, the second terminal carboxyl group leading to the synthesis of pimelic acid is enzymatically formed by a dehydrogenase classified, for example, under EC 1.2.1.-, such as, for example, a 6-oxohexanoate dehydrogenase (e.g., the gene product of chnE from *Acinetobacter* sp.) or a 7-oxoheptanoate dehydrogenase (e.g., such as the gene product of thnG from *Sphingomonas macrogolitabida*). See, for example, Iwaki et al., *Appl. Environ. Microbiol.*, 1999, 65(11), 5158-5162; or Lopez-Sanchez et al., *Appl. Environ. Microbiol.*, 2010, 76(1), 110-118. For example, a 6-oxohexanoate dehydrogenase can be classified, for example, under EC 1.2.1.63. For example, a 7-oxoheptanoate dehydrogenase can be classified, for example, under EC 1.2.1.-.

In some embodiments, the second terminal carboxyl group leading to the synthesis of pimelic acid is enzymatically formed by a CoA-transferase (e.g., a glutaconate CoA-transferase) classified, for example, under EC 2.8.3.12, such as, for example, a CoA-transferase from Acidaminococcus fermentans. See, for example, Buckel et al., 1981, *Eur. J. Biochem.*, 118:315-321.

In some embodiments, the second terminal carboxyl group leading to the synthesis of pimelic acid is enzymatically formed by a reversible CoA-ligase (e.g., a succinate-CoA ligase) classified, for example, under EC 6.2.1.5, such as, for example, a reversible CoA-ligase from *Thermococcus kodakaraensis*. See, for example, Shikata et al., 2007, *J. Biol. Chem.*, 282(37):26963-26970.

Figure 3:
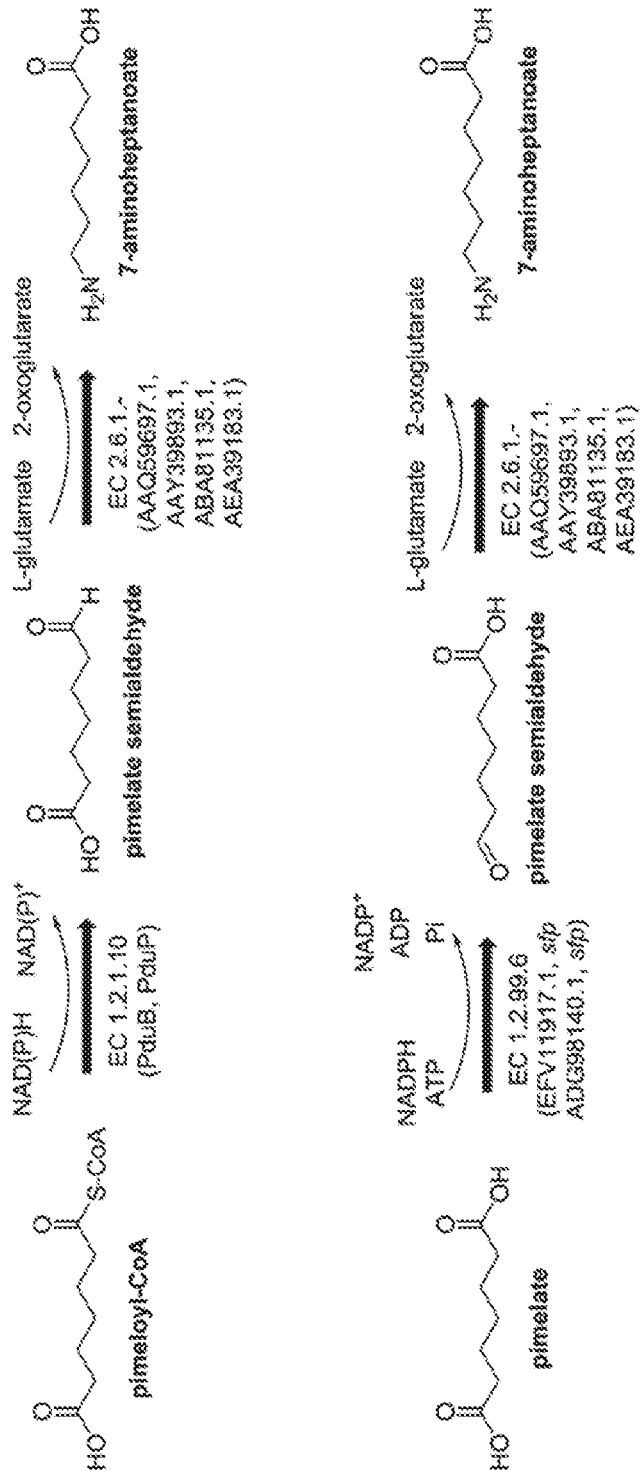
FIG. 3 is a schematic of exemplary biochemical pathways leading to 7-aminoheptanoate using pimeloyl-CoA, pimelate, or pimelate semialdehyde as central precursors.
Figure 4:
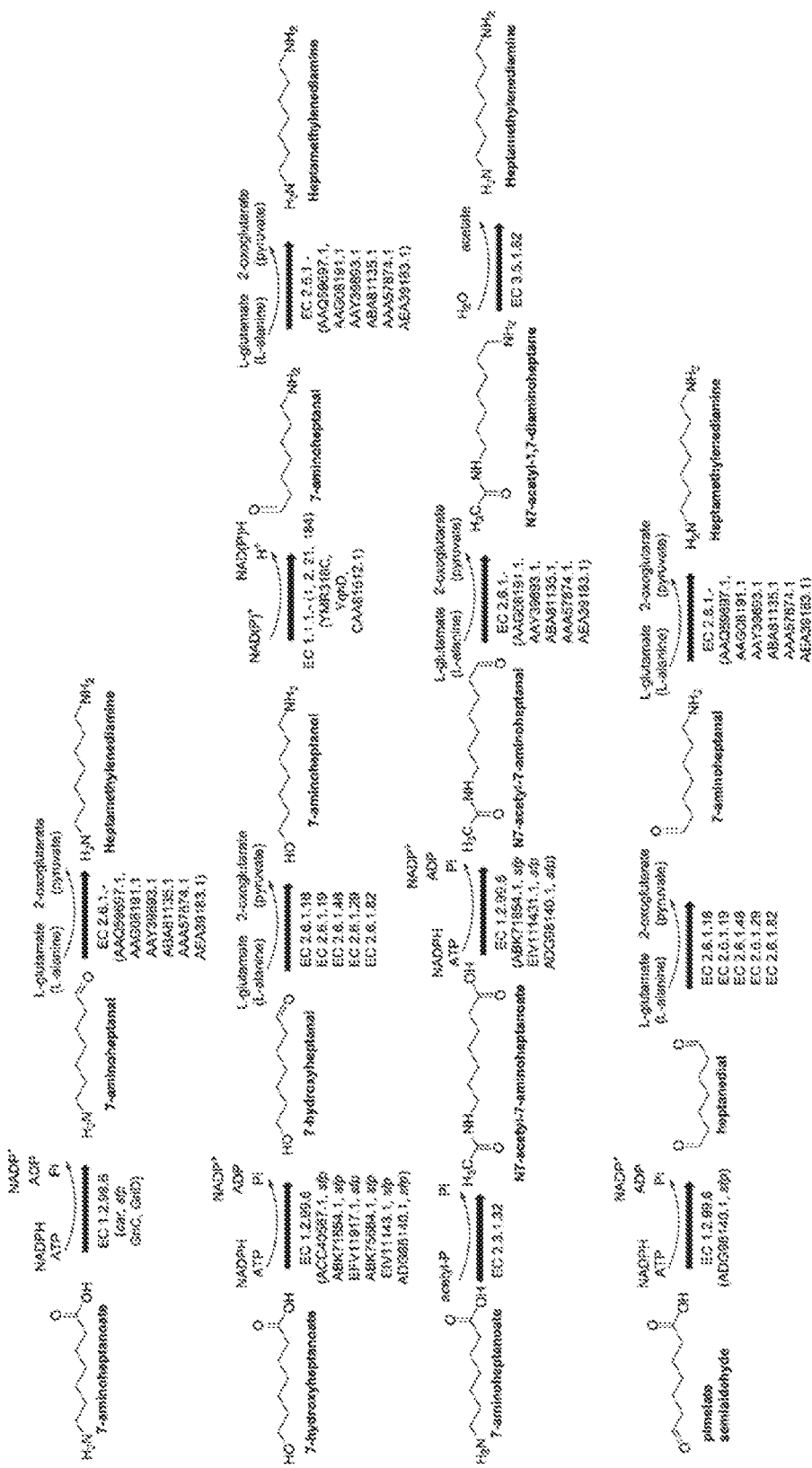
FIG. 4 is a schematic of exemplary biochemical pathways leading to heptamethylenediamine using 7-aminoheptanoate, 7-hydroxyheptanoate, or pimelate semialdehyde as central precursors.

Enzymes Generating the Terminal Amine Groups in the Biosynthesis of C7 Building Blocks As depicted in FIG. 3 and FIG. 4, terminal amine groups can be enzymatically formed using a ω-transaminase or a deacetylase.

In some embodiments, the first or second terminal amine group leading to the synthesis of 7-aminoheptanoic acid is enzymatically formed by a ω-transaminase classified, for example, under EC 2.6.1.18, EC 2.6.1.19, EC 2.6.1.29, EC 2.6.1.48, or EC 2.6.1.82, such as, for example, that obtained from *Chromobacterium violaceum* (Genbank Accession No. AAQ59697.1, SEQ ID NO: 8), *Pseudomonas aeruginosa*

(Genbank Accession No. AAG08191.1, SEQ ID NO: 9), *Pseudomonas syringae* (Genbank Accession No. AAY39893.1, SEQ ID NO: 10), *Rhodobacter sphaeroides* (Genbank Accession No. ABA81135.1, SEQ ID NO: 11), *Escherichia coli* (RefSeq Accession No. NP_417544.5, SEQ ID NO: 12), *Vibrio Fluvialis* (Genbank Accession No. AEA39183.1, SEQ ID NO: 13), *Streptomyces griseus*, or *Clostridium viride*. Some of these ω-transaminases are diamine ω-transaminases (e.g., SEQ ID NO: 12). For example, the ω-transaminases classified, for example, under EC 2.6.1.29 or EC 2.6.1.82 may be diamine ω-transaminases.

The reversible ω-transaminase from *Chromobacterium violaceum* (Genbank Accession No. AAQ59697.1, SEQ ID NO: 8) has demonstrated analogous activity accepting 6-aminohexanoic acid as amino donor, thus forming the first terminal amine group in adipate semialdehyde (Kaulmann et al., *Enzyme and Microbial Technology*, 2007, 41, 628-637).

The reversible 4-aminobubyrate:2-oxoglutarate transaminase from *Streptomyces griseus* has demonstrated analogous activity for the conversion of 6-aminohexanoate to adipate semialdehyde (Yonaha et al., *Eur. J. Biochem.*, 1985, 146: 101-106).

The reversible 5-aminovalerate transaminase from *Clostridium viride* has demonstrated analogous activity for the conversion of 6-aminohexanoate to adipate semialdehyde (Barker et al., *J. Biol. Chem.*, 1987, 262(19), 8994-9003).

In some embodiments, a terminal amine group leading to the synthesis of 7-aminoheptanoate or heptamethylenediamine is enzymatically formed by a diamine ω-transaminase. For example, the second terminal amino group can be enzymatically formed by a diamine ω-transaminase classified, for example, under EC 2.6.1.29 or classified, for example, under EC 2.6.1.82, such as, for example, the gene product of ygjG from *E. coli* (RefSeq Accession No. NP_417544.5, SEQ ID NO: 12).

The gene product of ygjG accepts a broad range of diamine carbon chain length substrates, such as putrescine, cadaverine and spermidine (see, for example, Samsonova et al., *BMC Microbiology*, 2003, 3:2).

The diamine ω-transaminase from *E. coli* strain B has demonstrated activity for 1,7 diaminoheptane (Kim, *The Journal of Chemistry*, 1964, 239(3), 783-786).

In some embodiments, the second terminal amine group leading to the synthesis of heptamethylenediamine is enzymatically formed by a deacetylase such as acetylputrescine deacetylase classified, for example, under EC 3.5.1.62. The acetylputrescine deacetylase from *Micrococcus luteus* K-11 accepts a broad range of carbon chain length substrates, such as acetylputrescine, acetylcadaverine and N⁸-acetylspermidine (see, for example, Suzuki et al., 1986, *BBA—General Subjects*, 882(1):140-142).

Figure 5:
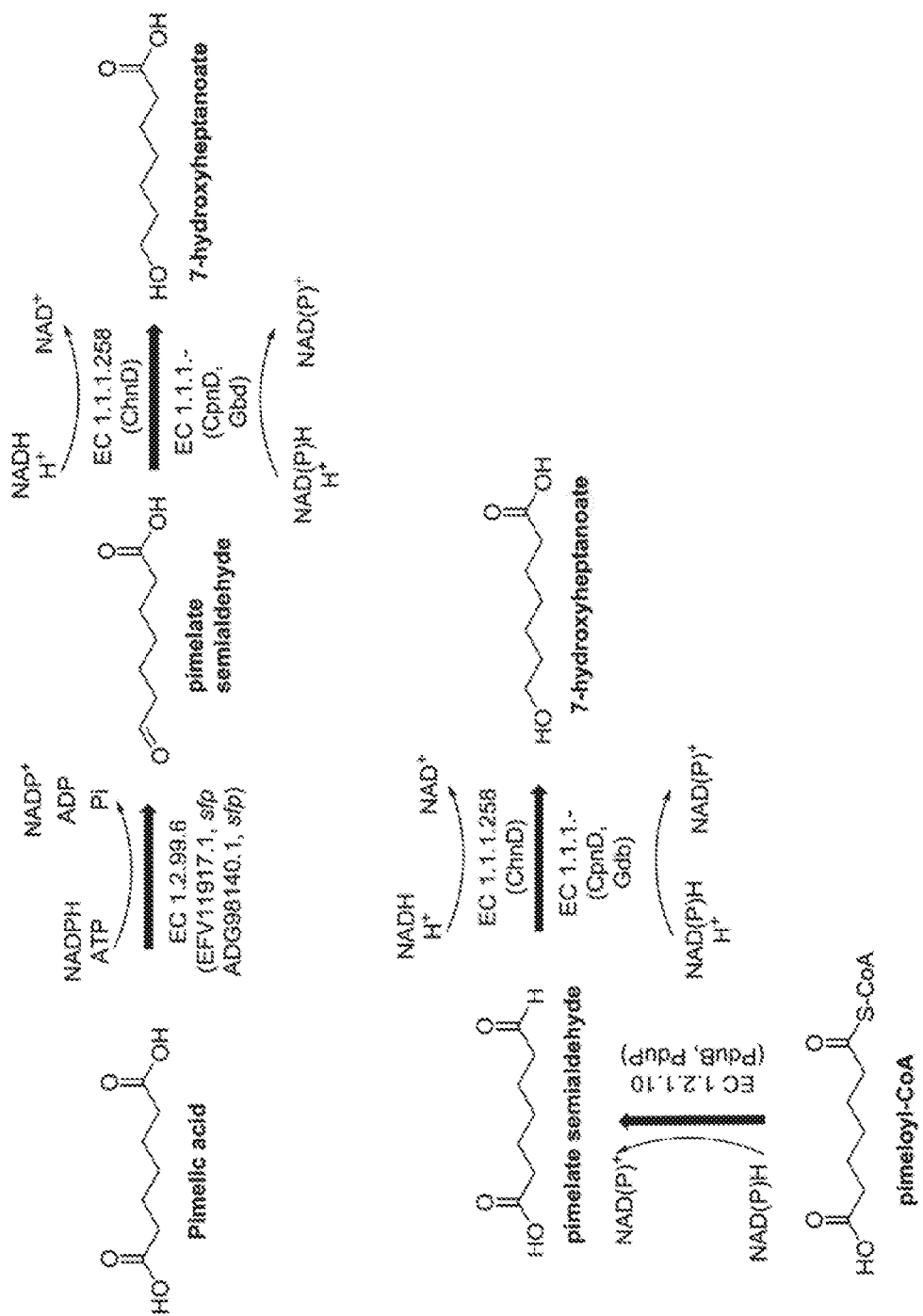
FIG. 5 is a schematic of exemplary biochemical pathways leading to 7-hydroxyheptanoate using pimelate, pimeloyl-CoA, or pimelate semialdehyde as central precursors.
Figure 6:
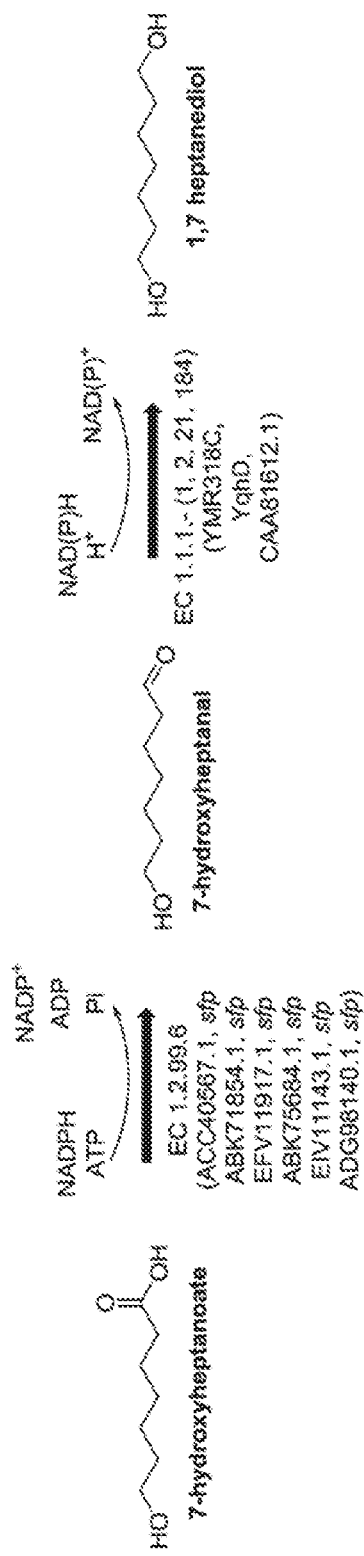
FIG. 6 is a schematic of an exemplary biochemical pathway leading to 1,7-heptanediol using 7-hydroxyheptanoate as a central precursor.

Enzymes Generating the Terminal Hydroxyl Groups in the Biosynthesis of C7 Building Blocks As depicted in FIG. 5 and FIG. 6, a terminal hydroxyl group can be enzymatically formed using an alcohol dehydrogenase.

In some embodiments, a terminal hydroxyl group leading to the synthesis of 1,7 heptanediol is enzymatically formed by an alcohol dehydrogenase classified, for example, under EC 1.1.1.- (e.g., 1, 2, 21, or 184), such as, for example, the gene product of YMR318C (classified, for example, under EC 1.1.1.2, see Genbank Accession No. CAA90836.1) (Larroy et al., 2002, *Biochem J.*, 361(Pt 1), 163-172), the gene product of yghD, the gene product of cpnD (Iwaki et al., 2002, *Appl. Environ. Microbiol.*, 68(11):5671-5684), the gene product of gbd, or a 6-hydroxyhexanoate dehydrogenase classified, for example, under EC 1.1.1.258, such as, for example, the gene product of chnD (Iwaki et al., *Appl. Environ. Microbiol.*, 1999, supra)

Biochemical Pathways

Pathways Using NADPH-Specific Enzymes to Pimeloyl-ACP as Central Precursor Leading to C7 Building Blocks In some embodiments, pimeloyl-ACP is synthesized from the central precursor malonyl-ACP, by conversion of malonyl-ACP to malonyl-ACP methyl ester by a malonyl-CoA O-methyltransferase classified, for example, under EC 2.1.1.197, such as, for example, the gene product of bioC; followed by conversion with malonyl-ACP to 3-oxo-glutyryl-ACP methyl ester by a β-ketoacyl-ACP synthase classified, for example, under EC 2.3.1.- (e.g., EC 2.3.1.41, EC 2.3.1.179 or EC 2.3.1.180), such as, for example, the gene product of fabB, fabF, or fabH; followed by conversion to 3-hydroxy-glutaryl-ACP methyl ester by a 3-oxoacyl-ACP reductase classified, for example, under EC 1.1.1.100, such as, for example, the gene product of fabG; followed by conversion to 2,3-dehydroglutaryl-ACP methyl ester by a 3-hydroxyacyl-ACP dehydratase classified, for example, under EC 4.2.1.59, such as, for example, the gene product of fabZ; followed by conversion to glutaryl-ACP methyl ester by an enoyl-ACP reductase classified, for example, under EC 1.3.1.10, such as, for example, the gene product of fabL; followed by conversion to 3-oxo-pimeloyl-ACP methyl ester by a β-ketoacyl-ACP synthase classified, for example, under EC 2.3.1.- (e.g., EC 2.3.1.41 or EC 2.3.1.179), such as, for example, the gene product of fabB or fabF; followed by conversion to 3-hydroxy-pimeloyl-ACP methyl ester by a 3-oxoacyl-ACP reductase classified, for example, under EC 1.1.1.100, such as, for example, the gene product of fabG; followed by conversion to 2,3-dehydropimeloyl-ACP methyl ester by a 3-hydroxyacyl-ACP dehydratase classified, for example, under EC 4.2.1.59, such as, for example, the gene product of fabZ; followed by conversion to pimeloyl-ACP methyl ester by an enoyl-ACP reductase classified, for example, under EC 1.3.1.10, such as, for example, the gene product of fabL; followed by conversion to pimeloyl-ACP by a pimeloyl-ACP methyl ester esterase classified, for example, under EC 3.1.1.85, such as, for example, the gene product of bioH. See FIG. 1A.

Pathways Using NADPH-Specific Enzymes to Pimeloyl-CoA as Central Precursor Leading to C7 Building Blocks In some embodiments, pimeloyl-CoA is synthesized from the central precursor malonyl-CoA, by conversion of malonyl-CoA to malonyl-CoA methyl ester by a malonyl-CoA O-methyltransferase classified, for example, under EC 2.1.1.197, such as, for example, the gene product of bioC; followed by conversion with acetyl-CoA to 3-oxo-glutaryl-CoA methyl ester by a β-ketothiolase classified, for example, under EC 2.3.1.16, such as, for example, the gene product of bktB, or by conversion with malonoyl-CoA by a β-ketoacyl-ACP synthase classified, for example, under EC 2.3.1.180, such as, for example, the gene product of fabH; followed by conversion to 3-hydroxy-glutaryl-CoA methyl ester by a 3-oxoacyl-ACP reductase classified, for example, under EC 1.1.1.100, such as, for example, the gene product of fabG, a 3-hydroxyacyl-CoA dehydrogenase classified, for example, under EC 1.1.1.157, such as, for example, the gene product of hbd, or an acetoacetyl-CoA reductase classified, for example, under EC 1.1.1.36 such as the gene product of phaB; followed by conversion to 2,3-dehydroglutaryl-CoA methyl ester by an enoyl-CoA hydratase classified, for example, under EC 4.2.1.119, such as, for example, the gene product of phaf; followed by conversion to glutaryl-CoA methyl ester by a reductase classified, for example, under EC 1.3.1.-, such as, for example, an enoyl-ACP reductase classified under EC 1.3.1.10, such as, for example, the gene product of fabL or a trans-2-enoyl-CoA reductase classified, for example, under EC 1.3.1.38 or EC 1.3.1.8, such as, for example, the gene product of ter or tdter; followed by conversion to 3-oxo-pimeloyl-CoA methyl ester by a β-ketoacyl-ACP synthase classified, for example, under EC 2.3.1.- (e.g., EC 2.3.1.41 or EC 2.3.1.179), such as, for example, the gene product of fabB or fabF, or a β-ketothiolase classified, for example, under EC 2.3.1.16, such as, for example, the gene product of bktB; followed by conversion to 3-hydroxy-pimeloyl-CoA methyl ester by a 3-oxoacyl-ACP reductase classified, for example, under EC 1.1.1.100, such as, for example, the gene product of fabG, a 3-hydroxyacyl-CoA dehydrogenase classified, for example, under EC 1.1.1.157, such as, for example, the gene product of hbd, or an acetoacetyl-CoA reductase classified, for example, under EC 1.1.1.36, such as, for example, the gene product of phaB; followed by conversion to 2,3-dehydropimeloyl-CoA methyl ester by an enoyl-CoA hydratase classified, for example, under EC 4.2.1.119, such as, for example, the gene product of phaJ; followed by conversion to pimeloyl-CoA methyl ester by a reductase classified, for example, under EC 1.3.1.-, such as, for example, an enoyl-ACP reductase classified, for example, under EC 1.3.1.10, such as the gene product of fabL, or a trans-2-enoyl-CoA reductase classified under, for example, EC 1.3.1.38 or EC 1.3.1.8, such as, for example, the gene product of ter or tdter; followed by conversion to pimeloyl-CoA by a pimeloyl-ACP methyl ester esterase classified, for example, under EC 3.1.1.85, such as, for example, the gene product of bioH. See FIG. 1B.

Pathways Using NADH-Specific Enzymes to Pimeloyl-CoA as Central Precursor Leading to C7 Building Blocks In some embodiments, pimeloyl-CoA is synthesized from the central precursor, malonyl-CoA, by conversion of malonyl-CoA to malonyl-CoA methyl ester by a malonyl-CoA O-methyltransferase classified, for example, under EC 2.1.1.197, such as, for example, the gene product of bioC; followed by conversion with acetyl-CoA to 3-oxo-glutaryl-CoA methyl ester by a β-ketothiolase classified, for example, under EC 2.3.1.16, such as, for example, the gene product of bktB or by conversion with malonyl-CoA by a β-ketoacyl-ACP synthase classified, for example, under EC 2.3.1.180, such as, for example, the gene product of fabH; followed by conversion to 3-hydroxy-glutaryl-CoA methyl ester by a 3-hydroxyacyl-CoA dehydrogenase classified, for example, under EC 1.1.1.- (e.g., EC 1.1.1.35), such as, for example, the gene product of fadB; followed by conversion to 2,3-dehydroglutaryl-CoA methyl ester by an enoyl-CoA hydratase classified, for example, under EC 4.2.1.17, such as, for example, the gene product of crt; followed by conversion to glutaryl-CoA methyl ester by a trans-2-enoyl-CoA reductase classified, for example, under EC 1.3.1.44, such as, for example, the gene product of ter or tdter or an enoyl-ACP reductase classified, for example, under EC 1.3.1.9, such as, for example, the gene product of fabI; followed by conversion to 3-oxopimeloyl-CoA methyl ester by a β-ketoacyl-ACP synthase classified, for example, under EC 2.3.1.- (e.g., EC 2.3.1.41 or EC 2.3.1.179), such as, for example, the gene product of fabB or fabF or a β-ketothiolase classified, for example, under EC 2.3.1.16, such as, for example, the gene product of bktB; followed by conversion to 3-hydroxy-pimeloyl-CoA methyl ester by a 3-hydroxyacyl-CoA dehydrogenase classified, for example, under EC 1.1.1.35, such as, for example, the gene product of fadB; followed by conversion to 2,3-dehydropimeloyl-CoA methyl ester by an enoyl-CoA hydratase classified, for example, under EC 4.2.1.17, such as, for example, the gene product of crt; followed by conversion to pimeloyl-CoA methyl ester by a trans-2-enoyl-CoA reductase classified, for example, under EC 1.3.1.44, such as, for example, the gene product of ter or tdter, or an enoyl-ACP reductase classified, for example, under EC 1.3.1.9, such as, for example, the gene product of fabI; followed by conversion to pimeloyl-CoA by a pimeloyl-ACP methyl ester esterase classified, for example, under EC 3.1.1.85, such as, for example, the gene product of bioH. See FIG. 1C.

Pathways Using Pimeloyl-CoA or Pimeloyl-ACP as Central Precursors to Pimelate

In some embodiments, pimelic acid is synthesized from the central precursor, pimeloyl-CoA, by conversion of pimeloyl-CoA to pimelate semialdehyde by an acetylating aldehyde dehydrogenase classified, for example, under EC 1.2.1.10, such as, for example, the gene product of pduB or pduP (see, for example, Lan et al., 2013, *Energy Environ. Sci.*, 6:2672-2681); followed by conversion to pimelic acid by a 7-oxoheptanoate dehydrogenase classified, for example, under EC 1.2.1.-, such as, for example, the gene product of thnG, a 6-oxohexanoate dehydrogenase classified, for example, under EC 1.2.1.-, such as, for example, the gene product of chnE, or an aldehyde dehydrogenase classified, for example, under EC 1.2.1.3. See FIG. 2.

In some embodiments, pimelic acid is synthesized from the central precursor, pimeloyl-CoA, by conversion of pimeloyl-CoA to pimelate by a thioesterase classified, for example, under EC 3.1.2.-, such as, for example, the gene products of yciA, tesB (Genbank Accession No. AAA24665.1, SEQ ID NO: 1), or acot13. See FIG. 2.

In some embodiments, pimelic acid is synthesized from the central precursor, pimeloyl-ACP, by conversion of pimeloyl-ACP to pimelate by a thioesterase classified, for example, under EC 3.1.2.- such as the gene products encoded by Genbank Accession No. ABJ63754.1, Genbank Accession No. CCC78182.1, tesA or fatB. See FIG. 2.

In some embodiments, pimelate is synthesized from the central precursor, pimeloyl-CoA, by conversion of pimeloyl-CoA to pimelate by a CoA-transferase such as a glutaconate CoA-transferase classified, for example, under EC 2.8.3.12. See FIG. 2.

In some embodiments, pimelate is synthesized from the central precursor, pimeloyl-CoA, by conversion of pimeloyl-CoA to pimelate by a reversible CoA-ligase such as a reversible succinate-CoA ligase classified, for example, under EC 6.2.1.5. See FIG. 2.

In some embodiments, pimelate is synthesized from the central precursor, pimelate semialdehyde, by conversion of pimelate semialdehyde to pimelate by a 6-oxohexanoate dehydrogenase or a 7-oxoheptanoate dehydrogenase (classified, for example, under EC 1.2.1.-), such as the gene product of thnG or chnE, or an aldehyde dehydrogenase classified, for example, under EC 1.2.1.3. See FIG. 2.

Pathways Using Pimeloyl-CoA or Pimelate Semialdehyde as Central Precursor to 7-Aminoheptanoate In some embodiments, 7-aminoheptanoate is synthesized from the central precursor, pimeloyl-CoA, by conversion of pimeloyl-CoA to pimelate semialdehyde by an acetylating aldehyde dehydrogenase classified, for example, EC 1.2.1.10, such as, for example, the gene product of pduB or pduP; followed by conversion of pimelate semialdehyde to 7-aminoheptanoate by a ω-transaminase classified, for example, under EC 2.6.1.18, EC 2.6.1.19, EC 2.6.1.29, EC 2.6.1.48, or EC 2.6.1.82. See FIG. 3.

In some embodiments, 7-aminoheptanoate is synthesized from the central precursor, pimelate semialdehyde, by conversion of pimelate semialdehyde to 7-aminoheptanoate by a ω-transaminase (e.g., EC 2.6.1.18, EC 2.6.1.19, or EC 2.6.1.48). See FIG. 3.

In some embodiments, 7-aminoheptanoate is synthesized from the central precursor, pimelate, by conversion of pimelate to pimelate semialdehyde by a carboxylate reductase classified, for example, under EC 1.2.99.6, such as, for example, the gene product of car optionally in combination with a phosphopantetheine transferase enhancer (e.g., encoded by a sfp (RefSeq Accession No. WP_003234549.1, SEQ ID NO: 14) gene from Bacillus subtilis or npt (Genbank Accession No. ABI83656.1, SEQ ID NO: 15) gene from Nocardia) or the gene products of griC and griD from Streptomyces griseus (Suzuki et al., J. Antibiot., 2007, 60(6), 380-387); followed by conversion of pimelate semialdehyde to 7-aminoheptanoate by a ω-transaminase (e.g., EC 2.6.1.18, EC 2.6.1.19, EC 2.6.1.48, EC 2.6.1.29, or EC 2.6.1.82, such as SEQ ID NOs: 8-13). The carboxylate reductase can be obtained, for example, from Mycobacterium marinum (Genbank Accession No. ACC40567.1, SEQ ID NO: 2), Mycobacterium smegmatis (Genbank Accession No. ABK71854.1, SEQ ID NO: 3), Segniliparus rugosus (Genbank Accession No. EFV11917.1, SEQ ID NO: 4), Mycobacterium smegmatis (Genbank Accession No. ABK75684.1, SEQ ID NO: 5), Mycobacterium massiliense (Genbank Accession No. EIV11143.1, SEQ ID NO: 6), or Segniliparus rotundus (Genbank Accession No. ADG98140.1, SEQ ID NO: 7). See FIG. 3.

Pathway Using 7-Aminoheptanoate, 7-Hydroxyheptanoate, or Pimelate Semialdehyde as Central Precursor to Heptamethylenediamine In some embodiments, heptamethylenediamine is synthesized from the central precursor, 7-aminoheptanoate, by conversion of 7-aminoheptanoate to 7-aminoheptanal by a carboxylate reductase classified, for example, under EC 1.2.99.6, such as, for example, the gene product of car (see above) optionally in combination with a phosphopantetheine transferase enhancer (e.g., encoded by a sfp (RefSeq Accession No. WP_003234549.1, SEQ ID NO: 14) gene from Bacillus subtilis or npt (Genbank Accession No. ABI83656.1, SEQ ID NO: 15) gene from Nocardia) or the gene product of griC and griD; followed by conversion of 7-aminoheptanal to heptamethylenediamine by a ω-transaminase classified, for example, under EC 2.6.1.18, EC 2.6.1.19, EC 2.6.1.29, EC 2.6.1.48, or EC 2.6.1.82, such as SEQ ID NOs: 8-13 (see above). See FIG. 4.

The carboxylate reductase encoded by the gene product of car and the phosphopantetheine transferase enhancer npt or sfp has broad substrate specificity, including terminal difunctional C4 and C5 carboxylic acids (Venkitasubramanian et al., Enzyme and Microbial Technology, 2008, 42, 130-137).

In some embodiments, heptamethylenediamine is synthesized from the central precursor, 7-hydroxyheptanoate (which can be produced as described in FIG. 5), by conversion of 7-hydroxyheptanoate to 7-hydroxyheptanal by a carboxylate reductase classified, for example, under EC 1.2.99.6, such as, for example, the gene product of car (see above) optionally in combination with a phosphopantetheine transferase enhancer (e.g., encoded by a sfp gene from Bacillus subtilis or npt gene from Nocardia) or the gene product of griC and griD (Suzuki et al., J. Antibiot., 2007, 60(6), 380-387); followed by conversion of 7-aminoheptanal to 7-aminoheptanol by a ω-transaminase classified, for example, under EC 2.6.1.18, EC 2.6.1.19, EC 2.6.1.29, EC 2.6.1.48, or EC 2.6.1.82, such as, for example, SEQ ID NOs: 8-13 (see above); followed by conversion to 7-aminoheptanal by an alcohol dehydrogenase classified, for example, under EC 1.1.1.- (e.g., EC 1.1.1.1, EC 1.1.1.2, EC 1.1.1.21, or EC 1.1.1.184), such as, for example, the gene product of YMR318C (classified, for example, under EC 1.1.1.2, see Genbank Accession No. CAA90836.1) or yqhD (from E. coli, GenBank Accession No. AAA69178.1) (Liu et al., Microbiology, 2009, 155, 2078-2085; Larroy et al., 2002, Biochem J., 361(Pt 1), 163-172; Jarboe, 2011, Appl. Microbiol. Biotechnol., 89(2), 249-257) or the protein having GenBank Accession No. CAA81612.1 (from Geobacillus stearothermophilus); followed by conversion to heptamethylenediamine by a ω-transaminase classified, for example, under EC 2.6.1.18, EC 2.6.1.19, EC 2.6.1.29, EC 2.6.1.48, or EC 2.6.1.82, such as, for example, SEQ ID NOs: 8-13 (see above). See FIG. 4.

In some embodiments, heptamethylenediamine is synthesized from the central precursor, 7-aminoheptanoate, by conversion of 7-aminoheptanoate to N7-acetyl-7-aminoheptanoate by a N-acetyltransferase such as a lysine N-acetyltransferase classified, for example, under EC 2.3.1.32; followed by conversion to N7-acetyl-7-aminoheptanal by a carboxylate reductase classified, for example, under EC 1.2.99.6, such as, for example, the gene product of car (see above) optionally in combination with a phosphopantetheine transferase enhancer (e.g., encoded by a sfp gene from Bacillus subtilis or npt gene from Nocardia) or the gene product of griC and griD; followed by conversion to N7-acetyl-1,7-diaminoheptane by a ω-transaminase classified, for example, under EC 2.6.1.18, EC 2.6.1.19, EC 2.6.1.29, EC 2.6.1.48, EC 2.6.1.46, or EC 2.6.1.82, such as, for example, SEQ ID NOs: 8-13 (see above); followed by conversion to heptamethylenediamine by an acetylputrescine deacylase classified, for example, under EC 3.5.1.62. See, FIG. 4.

In some embodiments, heptamethylenediamine is synthesized from the central precursor, pimelate semialdehyde, by conversion of pimelate semialdehyde to heptanedial by a carboxylate reductase classified, for example, under EC 1.2.99.6, such as, for example, the gene product of car (see above) optionally in combination with a phosphopantetheine transferase enhancer (e.g., encoded by a sfp gene from Bacillus subtilis or npt gene from Nocardia) or the gene product of griC and griD; followed by conversion to 7-aminoheptanal by a ω-transaminase classified, for example, under EC 2.6.1.18, EC 2.6.1.19, or EC 2.6.1.48; followed by conversion to heptamethylenediamine by a ω-transaminase classified, for example, under EC 2.6.1.18, EC 2.6.1.19, EC 2.6.1.29, EC 2.6.1.48, EC 2.6.1.46, or EC 2.6.1.82, such as, for example, SEQ ID NOs: 8-13, see above. See FIG. 4.

Pathways Using Pimelate or Pimelate Semialdehyde as Central Precursor to 1,7-Heptanediol In some embodiments, 7-hydroxyheptanoate is synthesized from the central precursor pimelate by conversion of pimelate to pimelate semialdehyde by a carboxylate reductase classified, for example, under EC 1.2.99.6, such as, for example, the gene product of car (see above) optionally in combination with a phosphopantetheine transferase enhancer (e.g., encoded by a sfp gene from Bacillus subtilis or npt gene from Nocardia) or the gene product of griC and griD; followed by conversion to 7-hydroxyheptanoate by a dehydrogenase classified, for example, under EC 1.1.1.-, such as, for example, a 6-hydroxyhexanoate dehydrogenase classified, for example, under EC 1.1.1.258, such as, for example, the gene from of chnD or a 5-hydroxypentanoate dehydrogenase classified, for example, under EC 1.1.1.-, such as, for example, the gene product of cpnD (see, for example, Iwaki et al., 2002, *Appl. Environ. Microbiol.*, 68(11):5671-5684) or a 4-hydroxybutyrate dehydrogenase, such as the gene product of gbd. See FIG. 5. Pimelate semialdehyde also can be produced from pimeloyl-CoA using an acetylating aldehyde dehydrogenase as described above. See FIG. 5.

In some embodiments, 1,7 heptanediol is synthesized from the central precursor 7-hydroxyheptanoate by conversion of 7-hydroxyheptanoate to 7-hydroxyheptanal by a carboxylate reductase classified, for example, under EC 1.2.99.6, such as, for example, the gene product of car (see above) optionally in combination with a phosphopantetheine transferase enhancer (e.g., encoded by a sfp gene from *Bacillus subtilis* or npt gene from *Nocardia*) or the gene product of griC and griD; followed by conversion of 7-hydroxyheptanal to 1,7 heptanediol by an alcohol dehydrogenase classified, for example, under EC 1.1.1.-, such as, for example, EC 1.1.1.1, EC 1.1.1.2, EC 1.1.1.21, or EC 1.1.1.184, such as, for example, the gene product of YMR318C or yqhD (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257) or the protein having GenBank Accession No. CAA81612.1 (from *Geobacillus stearothermophilus*). See, FIG. 6.

Cultivation Strategy

In some embodiments, the cultivation strategy entails achieving an aerobic, anaerobic, or micro-aerobic cultivation condition.

In some embodiments, the cultivation strategy entails nutrient limitation such as nitrogen, phosphate, or oxygen limitation.

In some embodiments, the cultivation strategy for certain recombinant microorganism strains includes addition of specific nutrients or substrates. In some embodiments, the cultivation strategy for a recombinant microorganism strain may include addition of glycine and purine. In some embodiments, the cultivation strategy for a recombinant microorganism strain may include addition of formate. In some embodiments, the cultivation strategy for a recombinant microorganism strain may include addition of formaldehyde. In some embodiments, the cultivation strategy for a recombinant microorganism strain may include addition of methanol.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more C7 building blocks can derive from biological or non-biological feedstocks.

In some embodiments, the biological feedstock can be, can include, or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida*, and *Yarrowia hpolytica* (Lee et al., *Appl. Biochem. Biotechnol.*, 2012, 166, 1801-1813; Yang et al., *Biotechnology for Biofuels*, 2012, 5:13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such as benzoate analogues has been demonstrated in several microorganisms such as *Pseudomonas putida* and *Cupriavidus necator* (Bugg et al., *Current Opinion in Biotechnology*, 2011, 22, 394-400; Perez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al., *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock can be or can derive from natural gas, syngas, $CO_2/H_2$, methanol, ethanol, benzoic acid, non-volatile residue (NVR), a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1), 152-156).

In some embodiments, the host microorganism is a prokaryote. For example, the prokaryote can be a bacterium from the genus *Escherichia* such as *Escherichia coli*; from the genus *Clostridia* such as *Clostridium ljungdahlii, Clostridium autoethanogenum*, or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida*, or *Pseudomonas oleavorans*; from the genus

*Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C7 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C7 building blocks.

Metabolic Engineering

The present disclosure provides methods involving less than all the steps described for all the above pathways. Such methods can involve, for example, one, two, three, four, five, six, seven, eight, nine, ten, eleven, or twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, or ten or more of such steps, can be performed within a recombinant host. This disclosure provides host cells of any of the genera and species listed and genetically engineered to express one or more (e.g., two, three, four, five, six, seven, eight, nine, 10, 11, or 12 or more) recombinant forms of any of the enzymes recited in the disclosure. Thus, for example, the host cells can contain exogenous nucleic acids encoding enzymes catalyzing one or more of the steps of any of the pathways described herein.

In addition, this disclosure recognizes that where enzymes have been described as accepting CoA-activated substrates, analogous enzyme activities associated with ACP-bound substrates exist that are not necessarily in the same enzyme class.

Also, this disclosure recognizes that where enzymes have been described accepting (R)-enantiomers of substrate, analogous enzyme activities associated with (S)-enantiomer substrates exist that are not necessarily in the same enzyme class.

This disclosure also recognizes that where an enzyme is shown to accept a particular co-factor, such as NADPH, or a co-substrate, such as acetyl-CoA, many enzymes are promiscuous in terms of accepting a number of different co-factors or co-substrates in catalyzing a particular enzyme activity. Also, this disclosure recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined herein can be gene dosed (i.e., overexpressed by having a plurality of copies of the gene in the host organism), into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C7 building block. Knock in and cloning strategies can likewise be devised to direct carbon flux to a C7 building block, as can combinations of attenuation, knock out, knock in, and cloning strategies.

Attenuation of the activity of a particular enzyme can occur through the inhibition of enzymatic activity itself and/or through a decrease in gene expression, including gene deletion/inactivation. Attenuation (decrease in gene expression) and knockout strategies include, but are not limited to: the use of transposons, homologous recombination (double cross-over approach), mutagenesis, non-homologous end joining (NHEJ), Zinc Fingers (ZFs), Transcription-Activator-Like Effectors (TALEs), and the Clustered Regulatory Interspaced Short Palindromic Repeats (CRISPR) sequences with CRISPR-Associated Protein 9 (Cas9) RNA interference (RNAi), double stranded RNA, and enzyme inhibitors. Cloning in strategies include, but are not limited to, inserting a nucleic acid of interest in a vector (e.g., a plasmid, bacteriophage, cosmid, or bacterial artificial chromosome) and inserting the vector into the host cell so that the host cell expresses the nucleic acid of interest. The terms "knocking in" and "cloning in" may both refer to introducing an exogenous nucleic acid into the host cells such that the host cell then expresses the exogenous nucleic acid.

In some embodiments, fluxomic, metabolomics, and transcriptomal data can be utilized to inform or support genome-scale system biology techniques, thereby devising genome scale attenuation or knockout strategies in directing carbon flux to a C7 building block.

In some embodiments, the host microorganism's tolerance to high concentrations of a C7 building block can be improved through continuous cultivation in a selective environment.

In some embodiments, the host microorganism's endogenous biochemical network can be attenuated or augmented to (1) ensure the intracellular availability of acetyl-CoA and malonyl-CoA, (2) create an NADH or NADPH imbalance that may only be balanced via the formation of one or more C7 building blocks, (3) prevent degradation of central metabolites and/or central precursors leading to and including one or more C7 building blocks, (4) ensure efficient efflux from the cell and/or (5) channel increased flux through the pathway leading to the C7 building block product(s).

In some embodiments requiring intracellular availability of acetyl-CoA for C7 building block synthesis, endogenous enzymes catalyzing the hydrolysis acetyl-CoA such as short-chain length thioesterases can be attenuated in the host organism.

In some embodiments requiring condensation of acetyl-CoA and propanoyl-CoA for C7 building block synthesis, one or more endogenous β-ketothiolases catalyzing the condensation of only acetyl-CoA to acetoacetyl-CoA such as the endogenous gene products of AtoB or phaA can be attenuated.

In some embodiments requiring the intracellular availability of acetyl-CoA for C7 building block synthesis, an endogenous phosphotransacetylase generating acetate such as pta can be attenuated (Shen et al., *Appl. Environ. Microbiol.*, 2011, 77(9):2905-2915).

In some embodiments requiring the intracellular availability of acetyl-CoA for C7 building block synthesis, an endogenous gene in an acetate synthesis pathway encoding an acetate kinase, such as ack, can be attenuated.

In some embodiments requiring the intracellular availability of acetyl-CoA and NADH for C7 building block synthesis, an endogenous gene encoding an enzyme that catalyzes the degradation of pyruvate to lactate such as a lactate dehydrogenase encoded by ldhA can be attenuated (Shen et al., 2011, supra).

In some embodiments requiring the intracellular availability of acetyl-CoA and NADH for C7 building block synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for C7 building block synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments, where pathways require excess NADH co-factor for C7 building block synthesis, a recombinant formate dehydrogenase gene can be overexpressed in the host organism (Shen et al., 2011, supra).

In some embodiments, where pathways require excess NADH or NADPH co-factor for C7 building block synthesis, an endogenous transhydrogenase dissipating the co-factor imbalance can be attenuated.

In some embodiments, an endogenous gene encoding an enzyme that catalyzes the degradation of pyruvate to ethanol such as pyruvate decarboxylase can be attenuated.

In some embodiments, an endogenous gene encoding an enzyme that catalyzes the generation of isobutanol such as a 2-oxoacid decarboxylase can be attenuated.

In some embodiments requiring the intracellular availability of acetyl-CoA for C7 building block synthesis, a recombinant acetyl-CoA synthetase such as the gene product of acs can be overexpressed in the microorganism (Satoh et al., *J. Bioscience and Bioengineering*, 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of a C7 building block, a gene such as udhA encoding a puridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of a C7 Building Block, a recombinant glyceraldehyde-3-phosphate-dehydrogenase gene such as gapN can be overexpressed in the host organisms (Brigham et al., 2012, supra).

In some embodiments, where pathways require excess NADPH co-factor in the synthesis of a C7 building block, a recombinant malic enzyme gene such as maeA or maeB can be overexpressed in the host organisms (Brigham et al., 2012, supra).

In some embodiments, where pathways require excess NADPH co-factor in the synthesis of a C7 building block, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of a C7 building block, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of a C7 building block, endogenous triose phosphate isomerase (EC 5.3.1.1) can be attenuated.

In some embodiments, where pathways require excess NADPH co-factor in the synthesis of a C7 building block, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific). For example, avoiding dissipation of an NADH imbalance towards C7 building blocks, a NADPH-specific glutamate dehydrogenase can be attenuated.

In some embodiments, an endogenous glutamate dehydrogenase (EC 1.4.1.3) that utilizes both NADH and NADPH as co-factors can be attenuated.

In some embodiments, a membrane-bound enoyl-CoA reductases can be solubilized via expression as a fusion protein to a small soluble protein such as a maltose binding protein (Gloerich et al., *FEBS Letters*, 2006, 580, 2092-2096).

In some embodiments using hosts that naturally accumulate polyhydroxyalkanoates, the endogenous polymer synthase enzymes can be attenuated in the host strain.

In some embodiments, a L-alanine dehydrogenase can be overexpressed in the host to regenerate L-alanine from pyruvate as an amino donor for ω-transaminase reactions.

In some embodiments, a L-glutamate dehydrogenase specific for the co-factor used to achieve co-factor imbalance can be overexpressed in the host to regenerate L-glutamate from 2-oxoglutarate as an amino donor for ω-transaminase reactions. For example, promoting dissipation of the NADH imbalance towards C7 building blocks, a NADH-specific glutamate dehydrogenase can be overexpressed.

In some embodiments, enzymes such as pimeloyl-CoA dehydrogenase classified under, EC 1.3.1.62; an acyl-CoA dehydrogenase classified, for example, under EC 1.3.8.7 or EC 1.3.8.1; and/or a glutaryl-CoA dehydrogenase classified, for example, under EC 1.3.8.6 that degrade central metabolites and/or central precursors leading to and including C7 building blocks can be attenuated.

In some embodiments, endogenous enzymes activating C7 building blocks via Coenzyme A esterification such as CoA-ligases (e.g., a pimeloyl-CoA synthetase) classified under, for example, EC 6.2.1.14 can be attenuated.

In some embodiments, a S-adenosylmethionine synthetase can be overexpressed in the host to generate S-Adenosyl-L-methionine as a co-factor for malonyl-ACP O-methyltransferase.

In some embodiments, an alcohol dehydrogenase, for example a methanol dehydrogenase, and a formaldehyde dehydrogenase can be overexpressed in the host to allow methanol catabolism via formate.

In some embodiments, where the production of formate requires methanol, formate acetyltransferase (e.g., formate acetyltransferase) classified under, for example, EC 2.3.1.54, and/or a pyruvate formate-lyase (PFL)-like enzyme (e.g., pyruvate formate-lyase (PFL)-like enzyme TdcE) classified under, for example, EC 2.3.1.54, can be attenuated.

In some embodiments, where the production of formate requires methanol, an exogenous S-(hydroxymethyl) glutathione dehydrogenase, classified under, for example, EC 1.1.1.284, and/or an exogenous S-formylglutathione hydrolase FrmB classified under, for example, EC 3.1.2.12, can be expressed in the host cell.

In some embodiments, where a modified tetrahydrofolate metabolic cycle requires formate, bifunctional protein FolD (folD) can be attenuated and an exogenous formate-tetrahydrofolate ligase (fhs), classified under, for example, EC 6.3.4.3, can be expressed in the host cell (Sah et al., *J. Bacteriology*, 2015, 197(4), 717-726).

In some embodiments, the efflux of a C7 building block across the cell membrane to the extracellular media can be enhanced or amplified by genetically engineering structural modifications to the cell membrane or increasing any associated transporter activity for a C7 building block.

The efflux of heptamethylenediamine can be enhanced or amplified by overexpressing broad substrate range multidrug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499), NorA from *Staphylococcus aereus* (Ng et al., 1994, *Antimicrob Agents Chemother*, 38(6), 1345-1355), or Bmr from *Bacillus subtilis* (Neyfakh, 1992, *Antimicrob Agents Chemother*, 36(2), 484-485).

The efflux of 7-aminoheptanoate and heptamethylenediamine can be enhanced or amplified by overexpressing the solute transporters such as the lysE transporter from *Corynebacterium glutamicum* (Bellmann et al., 2001, *Microbiology*, 147, 1765-1774).

The efflux of pimelic acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C7 Building Blocks Using a Recombinant Host

Typically, one or more C7 building blocks can be produced by providing a host microorganism and culturing the provided microorganism with a culture medium containing a suitable carbon source as described above. In general, the culture media and/or culture conditions can be such that the microorganisms grow to an adequate density and produce a C7 building block efficiently. For large-scale production processes, any method can be used such as those described elsewhere (Manual of Industrial Microbiology and Biotechnology, 2$^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, or 500 gallon or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C7 building block. Once produced, any method can be used to isolate C7 building blocks. For example, C7 building blocks can be recovered selectively from the fermentation broth via adsorption processes. In the case of pimelic acid and 7-aminoheptanoic acid, the resulting eluate can be further concentrated via evaporation, crystallized via evaporative and/or cooling crystallization, and the crystals recovered via centrifugation. In the case of heptamethylenediamine and 1,7-heptanediol, distillation may be employed to achieve the desired product purity.

The invention is further described in the following non-limiting example.

EXAMPLES

Figure 8B:
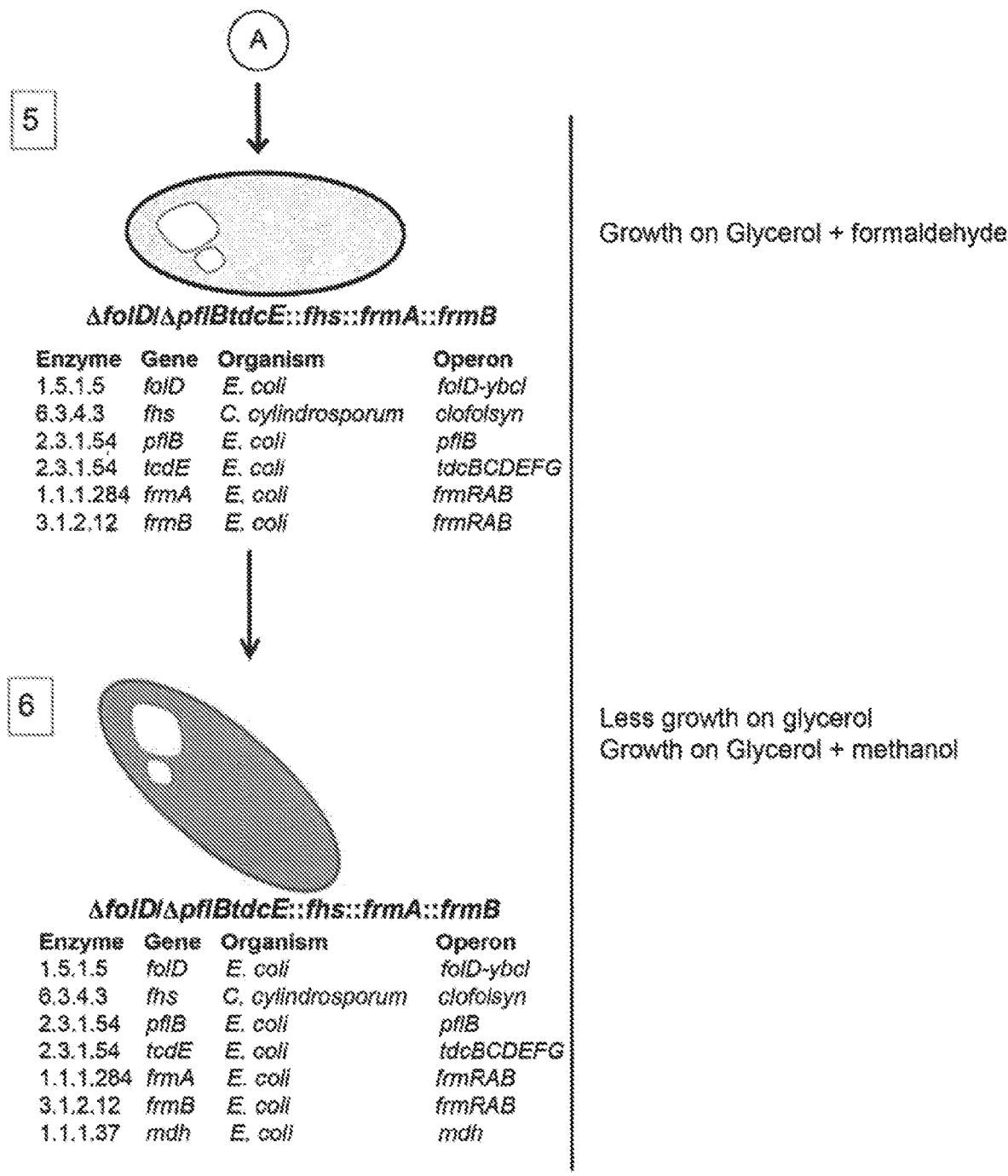
FIG. 8B shows the continuation of the cloning strategy represented in FIG. 8A.
Figure 9:
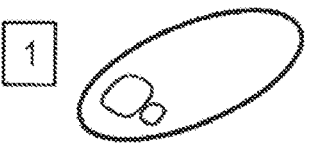
FIG. 9 shows a schematic of an additional cloning strategy for producing a recombinant host strain that can assimilate methanol produced during BioH enzyme activity into essential purines and initiator tRNAs.

Generating a strain that can utilize the methanol byproduct from the 7-AHA pathway as source of formate so that the methanol is an essential intermediate for purines and initiator tRNAs may be accomplished through the proposed cloning strategies discussed below and diagrammed in FIGS. 8A, 8B, and 9. FIGS. 8A, 8B, and 9 show the expected strains following appropriate knock out or knock in (left side) as well as the growth conditions for screening and the expected outcomes (right side). According to this disclosure, the ideal screen will be based on the viability of the host strain as well as pimelate production.

Example 1

Cloning Strategy 1

The cloning strategy involves starting with a "pimelate strain" (see FIG. 8A), where a pimelate host strain is a strain that has a pathway for producing pimelate or C7 building blocks (e.g., the 7-AHA pathway, see FIG. 7). The biosynthesis of C7 building blocks, such as 7-AHA, by recombinant host microorganisms has been described in U.S. Patent Publication Nos. 2014/0186904 and 2014/0242655. The host organism in the cloning strategy described in this example is *E. coli*.

The cloning strategy involves the knocking out folD to produce an fhs-supported *E. coli* folD deletion (ΔfolD+fhs) model. See FIG. 8A, strains 2 and 3. The ΔfolD/p-fhs strain and the ΔfolD:fhs strain, in which the strain is supported by a single copy of fhs, are described by Sah et al. (Sah et al., *J. Bacteriol.*, 2015, 197(4), 717-726). The deletion of FolD in *E. coli* results in autotrophy for purines and glycine. To enable sufficient growth the media will be supplemented with purines and glycine, which PflB and TdcE convert to formate. The availability of formate then enables Fhs to convert THF to $N^{10}$-formyltetrahydrofolate ($N^{10}$-fTHF). $N^{10}$-fTHF is important for the de novo pathway of purine nucleotide biosynthesis and formylation of the initiator tRNA (tRNAfMet) (FIGS. 10A and 10B).

The next strain, strain 4 (FIG. 8A, strain 4), to be engineered consists of deleting the pflB and tdcE genes from strain 3 which eliminates the source of formate. Knocking in the frmA and frmB genes into strain 4, would produce strain 5 (FIG. 8B, strain 5). The latter can then grow in media containing formaldehyde as FrmA and FrmB enable the spontaneous oxidation of formaldehyde into formate, through the organism's formaldehyde detoxification pathway linked to glutathione (GSH).

Strain 6 (FIG. 8B, strain 6), which is the final strain will be established by knocking in an alcohol dehydrogenase gene (adh). Methanol will accumulate after engineering a 7-AHA pathway producing 7-AHA from the central carbon metabolism into this strain. To enable the strain to utilize methanol effectively, the C1 substrate must be converted by unique enzymes and subsequently connected via intermediates to the central metabolism and thus converted into formate indispensable for the growth of the strain. Knocking in a heterologous aerobic adh gene enables the conversion of methanol to formaldehyde catalysed by Adh as well as subsequent oxidation of formaldehyde into formate. This strain can then grow, requiring methanol as a growth critical intermediate which is necessary for the synthesis of purine nucleotides, thymidylate, and tRNAfMet. This will ensure that as the strain grows, increased flux is channelled through the 7-AHA pathway to produce more 7-AHA.

Example 2

Cloning Strategy 2

The second cloning strategy also starts with a pimelate strain, as was discussed in Example 1. The host organism in the cloning strategy described in this example is *E. coli*.

The cloning strategy involves the knocking out folD to produce an fhs-supported *E. coli* folD deletion (ΔfolD+fhs) model, as described above. See FIG. 9, strain 2. As described above, to enable sufficient growth of this strain the media must be supplemented with purines and glycine.

The next strain (FIG. 9, strain 3) to be engineered consists of knocking in the frmA and frmB genes from strain 2. Strain 3 can then grow in media containing formaldehyde as the frmA and frmB gene products enable the spontaneous oxidation of formaldehyde into formate, through the organism's formaldehyde detoxification pathway linked to glutathione (GSH).

The final strain, strain 4 (FIG. 9), is established by knocking in an alcohol dehydrogenase gene (adh). Knocking in a heterologous aerobic adh gene enables the conversion of methanol to formaldehyde catalysed by Adh as well as subsequent oxidation of formaldehyde into formate.

The proposed cloning strategy is further highlighted in Table 1.

TABLE 1

Proposed strains and projected outcomes

| Proposed strain | Growth conditions | Remarks |
| --- | --- | --- |
| *E. coli* pimelate strain (FIG. 9, strain 1) | Growth on glycerol | |
| fhs-supported *E. coli* folD deletion (ΔfolD::fhs strain) (FIG. 9, strain 2) | Growth on glycerol + formate + glycine (+purine) No growth on glycerol | A model discussed in Sah et al. (Sah et al., 2015). Generation of *E. coli* ΔfolD strain having a single copy of fhs (ΔfolD::fhs) by subjecting the ΔfolD/p-fhs strain to curring of p-fhs. The deletion of folD in *E. coli* results in autotrophy for purines and glycine. To enable sufficient growth, media may be supplemented with purines and glycine |
| ΔfolD::fhs::frmA::frmB (FIG. 9, strain 3) | Growth on glycerol + formaldehyde + glycine (+purine) No growth on glycerol | Introduction of frmA and frmB enables oxidation of formaldehyde to formate |
| ΔfolD::fhs::mdh::frmA::frmB (FIG. 9, strain 4) | Growth on glycerol + methanol + glycine (+purine) No growth on glycerol | Introduction of adh converts methanol to formaldehyde which is then oxidised to formate |

The systems described in the predictive examples have a potential improvement of about 15 to about 22% of the maximum theoretical yield in 7-AHA production.

We claim:

1. A method for regulating biosynthesis of a product in a host cell, wherein the product comprises pimelic acid, 7-aminoheptanoate, 7-hydroxyheptanoate, heptamethylenediamine, 7-aminoheptanol, or 1,7-heptanediol, or salts thereof, using a pathway having a pimeloyl-acyl carrier protein (pimeloyl-ACP) intermediate, the method comprising converting methanol to formate via enzymatic reaction, wherein the formate is used in the conversion of tetrahydrofolate to N1°-formyl-tetrahydrofolate, wherein: the methanol is produced during pimeloyl-ACP methyl ester esterase (BioH) enzyme activity in which BioH removes a methyl group from pimeloyl-ACP methyl ester during conversion of pimeloyl-ACP methyl ester to pimeloyl ACP, wherein the BioH activity is increased compared to an unmodified host cell: and the method comprises downregulating (a) bifunctional protein (FolD) activity by attenuating folD and/or (b) formate acetyltransferase 1 (PflB) activity and formate acetyltransferase-like enzyme (TdcE) activity: and the method comprises inserting into the host cell (i) a gene encoding an S-formylglutathione hydrolase (frmB), (ii) a gene encoding a formate-tetrahydrofolate ligase (fhs), (iii) a gene encoding an alcohol dehydrogenase (adh), and (iv) a gene encoding an S-(hydroxymethyl) glutathione dehydrogenase (frmA), wherein the S-formylglutathione hydrolase has at least 90% sequence identity to an amino acid sequence selected from the group consisting of SEQ ID NOs: 27-30, the formate-tetrahydrofolate ligase has at least 90% sequence identity to an amino acid sequence selected from the group consisting of SEQ ID NOs: 18-22, the alcohol dehydrogenase has at least 90% sequence identity to the amino acid sequence set forth in SEQ ID NO: 31, and the S-(hydroxymethyl) glutathione dehydrogenase has at least 90% sequence identity to an amino acid sequence selected from the group consisting of SEQ ID NOs: 23-26.

2. The method of claim 1, wherein:
downregulating the activity of PflB and TdcE comprises a step of deleting pflB and tdcE.

3. The method of claim 1, wherein:
the expression of adh, frmA, and frmB allows conversion of the methanol to formate; and
the biosynthesis of the product is increased compared to a control cell transformed with a vector without said genes.

4. The method of claim 1, wherein the product comprises a salt of pimelic acid, 7-aminoheptanoate, 7-hydroxyheptanoate, heptamethylenediamine, 7-aminoheptanol, or 1,7-heptanediol.

5. The method of claim 1, wherein the method is performed in a recombinant host.

6. The method of claim 5, wherein a principal carbon source fed to the host derives from biological or non-biological feedstocks.

7. The method of claim 6, wherein:
the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste: or
the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

8. The method of claim 5, wherein the host is a prokaryote selected from the group consisting of the following genera: *Escherichia; Clostridia; Corynebacteria; Cupriavidus; Pseudomonas; Delftia; Bacillus; Lactobacillus; Lactococcus*; and *Rhodococcus*; or the host is a eukaryote selected from the group consisting of the following genera: *Aspergillus; Saccharomyces; Pichia; Yarrowia; Issatchenkia; Debaryomyces; Arxula*; and *Kluyveromyces*.

9. The method of claim 8, wherein the host is *Escherichia coli*.

10. The method of claim 8, wherein: the prokaryote is *Escherichia coli, Clostridium lungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Pseudomonas oleavorans, Delftia acidovorans, Bacillus subtillis, Lactobacillus delbrueckii, Lactococcus lactis*, or *Rhodococcus equi*; or the eukaryote is *Aspergillus niger, Saccharomyces cerevisiae, Pichia pastoris, Yarrowia lipolytica, Jssathenkia orientalis, Debaryomyces hansenii, Arxula adenoinivorans*, or *Kluyveromyces lactis*.

11. The method of claim 5 wherein:
the host comprises one or more of the following attenuated enzymes:
polyhydroxyalkanoate synthase; an acetyl-CoA thioesterase; an acetyl-CoA specific β-ketothiolase; a phosphotransacetylase forming acetate; an acetate kinase; a lactate dehydrogenase; a menaquinol-fumarate oxidoreductase; a 2-oxoacid decarboxylase producing isobutanol; an alcohol dehydrogenase forming ethanol; a triose phosphate isomerase; a pyruvate decarboxylase; a glucose-6-phosphate isomerase; a transhydrogenase dissipating the NADH or NADPH imbalance; a glutamate dehydrogenase dissipating the NADH or NADPH imbalance; a NADH/NADPH-utilizing glutamate dehydrogenase; a pimeloyl-CoA dehydrogenase; an acyl-CoA dehydrogenase accepting C7 building blocks and central precursors as substrates; a glutaryl-CoA dehydrogenase; or a pimeloyl-CoA synthetase; and/or the host overexpresses an acetyl-CoA synthetase; a 6-phosphogluconate dehydrogenase; a transketolase; a puridine nucleotide transhydrogenase; a formate dehydrogenase; a glyceraldehyde-3P-dehydrogenase; a malic enzyme; a glucose-6-phosphate dehydrogenase; a fructose 1,6 diphosphatase; a L-alanine dehydrogenase; a L-glutamate dehydrogenase specific to the NADH or NADPH used to generate a co-factor imbalance; a methanol dehydrogenase; a formaldehyde dehydrogenase; a diamine transporter; a dicarboxylate transporter; an S-adenosylmethionine synthetase; and/or a multidrug transporter.

* * * * *

```
                            SEQUENCE LISTING

<160> NUMBER OF SEQ ID NOS: 37

<210> SEQ ID NO 1
<211> LENGTH: 286
<212> TYPE: PRT
<213> ORGANISM: Escherichia coli

<400> SEQUENCE: 1

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285

<210> SEQ ID NO 2
<211> LENGTH: 1174
<212> TYPE: PRT
<213> ORGANISM: Mycobacterium marinum

<400> SEQUENCE: 2

Met Ser Pro Ile Thr Arg Glu Glu Arg Leu Glu Arg Arg Ile Gln Asp
1               5                   10                  15
```

```
Leu Tyr Ala Asn Asp Pro Gln Phe Ala Ala Lys Pro Ala Thr Ala
             20                  25                  30
Ile Thr Ala Ala Ile Glu Arg Pro Gly Leu Pro Leu Pro Gln Ile Ile
         35                  40                  45
Glu Thr Val Met Thr Gly Tyr Ala Asp Arg Pro Ala Leu Ala Gln Arg
 50                  55                  60
Ser Val Glu Phe Val Thr Asp Ala Gly Thr Gly His Thr Thr Leu Arg
 65                  70                  75                  80
Leu Leu Pro His Phe Glu Thr Ile Ser Tyr Gly Glu Leu Trp Asp Arg
                 85                  90                  95
Ile Ser Ala Leu Ala Asp Val Leu Ser Thr Gln Thr Val Lys Pro
                100                 105                 110
Gly Asp Arg Val Cys Leu Leu Gly Phe Asn Ser Val Asp Tyr Ala Thr
             115                 120                 125
Ile Asp Met Thr Leu Ala Arg Leu Gly Ala Val Ala Val Pro Leu Gln
130                 135                 140
Thr Ser Ala Ala Ile Thr Gln Leu Gln Pro Ile Val Ala Glu Thr Gln
145                 150                 155                 160
Pro Thr Met Ile Ala Ala Ser Val Asp Ala Leu Ala Asp Ala Thr Glu
                165                 170                 175
Leu Ala Leu Ser Gly Gln Thr Ala Thr Arg Val Leu Val Phe Asp His
                180                 185                 190
His Arg Gln Val Asp Ala His Arg Ala Ala Val Glu Ser Ala Arg Glu
            195                 200                 205
Arg Leu Ala Gly Ser Ala Val Val Glu Thr Leu Ala Glu Ala Ile Ala
        210                 215                 220
Arg Gly Asp Val Pro Arg Gly Ala Ser Ala Gly Ser Ala Pro Gly Thr
225                 230                 235                 240
Asp Val Ser Asp Asp Ser Leu Ala Leu Leu Ile Tyr Thr Ser Gly Ser
                245                 250                 255
Thr Gly Ala Pro Lys Gly Ala Met Tyr Pro Arg Arg Asn Val Ala Thr
                260                 265                 270
Phe Trp Arg Lys Arg Thr Trp Phe Glu Gly Gly Tyr Glu Pro Ser Ile
            275                 280                 285
Thr Leu Asn Phe Met Pro Met Ser His Val Met Gly Arg Gln Ile Leu
        290                 295                 300
Tyr Gly Thr Leu Cys Asn Gly Gly Thr Ala Tyr Phe Val Ala Lys Ser
305                 310                 315                 320
Asp Leu Ser Thr Leu Phe Glu Asp Leu Ala Leu Val Arg Pro Thr Glu
                325                 330                 335
Leu Thr Phe Val Pro Arg Val Trp Asp Met Val Phe Asp Glu Phe Gln
                340                 345                 350
Ser Glu Val Asp Arg Arg Leu Val Asp Gly Ala Asp Arg Val Ala Leu
            355                 360                 365
Glu Ala Gln Val Lys Ala Glu Ile Arg Asn Asp Val Leu Gly Gly Arg
        370                 375                 380
Tyr Thr Ser Ala Leu Thr Gly Ser Ala Pro Ile Ser Asp Glu Met Lys
385                 390                 395                 400
Ala Trp Val Glu Glu Leu Leu Asp Met His Leu Val Glu Gly Tyr Gly
                405                 410                 415
Ser Thr Glu Ala Gly Met Ile Leu Ile Asp Gly Ala Ile Arg Arg Pro
                420                 425                 430
```

```
Ala Val Leu Asp Tyr Lys Leu Val Asp Val Pro Asp Leu Gly Tyr Phe
            435                 440                 445

Leu Thr Asp Arg Pro His Pro Arg Gly Glu Leu Leu Val Lys Thr Asp
450                     455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
                500                 505                 510

Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
                565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
            595                 600                 605

Gly Ile Arg Lys Leu Ala Arg Pro Gln Leu Lys Lys His Tyr Gly Glu
        610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Ala Leu Leu Gly Gly Ser Ala Ser Asp Val
            660                 665                 670

Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
        690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
            755                 760                 765

Pro Arg Leu Pro Ala Ala Asn Thr Gln Val Arg Thr Val Leu Leu Thr
770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
            835                 840                 845

Glu Val Leu Ala Gly Asp Lys Gly Glu Ala Asp Leu Gly Leu Asp Arg
```

```
                850                 855                 860
Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
        915                 920                 925

Pro Pro Ser Ala Phe Thr Glu Asp Ala Asp Ile Arg Val Ile Ser Ala
    930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp  Met Phe Thr Arg Met  Ile Leu Ser
        995                 1000                 1005

Leu Ala  Ala Thr Gly Ile Ala  Pro Gly Ser Phe Tyr  Glu Leu Ala
    1010                 1015                 1020

Ala Asp  Gly Ala Arg Gln Arg  Ala His Tyr Asp Gly  Leu Pro Val
    1025                 1030                 1035

Glu Phe  Ile Ala Glu Ala Ile  Ser Thr Leu Gly Ala  Gln Ser Gln
    1040                 1045                 1050

Asp Gly  Phe His Thr Tyr His  Val Met Asn Pro Tyr  Asp Asp Gly
    1055                 1060                 1065

Ile Gly  Leu Asp Glu Phe Val  Asp Trp Leu Asn Glu  Ser Gly Cys
    1070                 1075                 1080

Pro Ile  Gln Arg Ile Ala Asp  Tyr Gly Asp Trp Leu  Gln Arg Phe
    1085                 1090                 1095

Glu Thr  Ala Leu Arg Ala Leu  Pro Asp Arg Gln Arg  His Ser Ser
    1100                 1105                 1110

Leu Leu  Pro Leu Leu His Asn  Tyr Arg Gln Pro Glu  Arg Pro Val
    1115                 1120                 1125

Arg Gly  Ser Ile Ala Pro Thr  Asp Arg Phe Arg Ala  Ala Val Gln
    1130                 1135                 1140

Glu Ala  Lys Ile Gly Pro Asp  Lys Asp Ile Pro His  Val Gly Ala
    1145                 1150                 1155

Pro Ile  Ile Val Lys Tyr Val  Ser Asp Leu Arg Leu  Leu Gly Leu
    1160                 1165                 1170

Leu
```

<210> SEQ ID NO 3
<211> LENGTH: 1173
<212> TYPE: PRT
<213> ORGANISM: Mycobacterium smegmatis

<400> SEQUENCE: 3

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
```

```
                35                  40                  45
Ala His Lys Pro Gly Leu Arg Leu Ala Glu Ile Leu Gln Thr Leu Phe
 50                      55                  60

Thr Gly Tyr Gly Asp Arg Pro Ala Leu Gly Tyr Arg Ala Arg Glu Leu
65                  70                  75                  80

Ala Thr Asp Glu Gly Arg Thr Val Thr Arg Leu Leu Pro Arg Phe
                85                  90                  95

Asp Thr Leu Thr Tyr Ala Gln Val Trp Ser Arg Val Gln Ala Val Ala
                100                 105                 110

Ala Ala Leu Arg His Asn Phe Ala Gln Pro Ile Tyr Pro Gly Asp Ala
            115                 120                 125

Val Ala Thr Ile Gly Phe Ala Ser Pro Asp Tyr Leu Thr Leu Asp Leu
130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
                180                 185                 190

Asp Val Asn Ser Val Ser Gln Leu Val Val Phe Asp His His Pro Glu
            195                 200                 205

Val Asp Asp His Arg Asp Ala Leu Ala Arg Ala Arg Glu Gln Leu Ala
210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
                260                 265                 270

Ala Met Tyr Thr Glu Ala Met Val Ala Arg Leu Trp Thr Met Ser Phe
            275                 280                 285

Ile Thr Gly Asp Pro Thr Pro Val Ile Asn Val Asn Phe Met Pro Leu
290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
            355                 360                 365

Thr Gln Gly Ala Asp Glu Leu Thr Ala Glu Lys Gln Ala Gly Ala Glu
            370                 375                 380

Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
                420                 425                 430

Thr Arg Asp Gly Val Ile Val Arg Pro Pro Val Ile Asp Tyr Lys Leu
            435                 440                 445

Ile Asp Val Pro Glu Leu Gly Tyr Phe Ser Thr Asp Lys Pro Tyr Pro
450                 455                 460
```

-continued

```
Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
    530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
        595                 600                 605

Phe Ser Ala Ala Asn Gly Leu Leu Ser Gly Val Gly Lys Leu Leu Arg
610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
        675                 680                 685

Leu Gly Gly Asp Ser Leu Ser Ala Leu Thr Leu Ser Asn Leu Leu Ser
    690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
                725                 730                 735

Gly Asp Arg Arg Pro Ser Phe Thr Thr Val His Gly Ala Asp Ala Thr
            740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
    770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
                805                 810                 815

Ile Val Arg Gly Arg Asp Asp Ala Ala Ala Arg Ala Arg Leu Thr Gln
            820                 825                 830

Ala Tyr Asp Thr Asp Pro Glu Leu Ser Arg Arg Phe Ala Glu Leu Ala
        835                 840                 845

Asp Arg His Leu Arg Val Val Ala Gly Asp Ile Gly Asp Pro Asn Leu
    850                 855                 860

Gly Leu Thr Pro Glu Ile Trp His Arg Leu Ala Ala Glu Val Asp Leu
865                 870                 875                 880
```

Val Val His Pro Ala Ala Leu Val Asn His Val Leu Pro Tyr Arg Gln
            885                 890                 895

Leu Phe Gly Pro Asn Val Val Gly Thr Ala Glu Val Ile Lys Leu Ala
        900                 905                 910

Leu Thr Glu Arg Ile Lys Pro Val Thr Tyr Leu Ser Thr Val Ser Val
    915                 920                 925

Ala Met Gly Ile Pro Asp Phe Glu Glu Asp Gly Asp Ile Arg Thr Val
930                 935                 940

Ser Pro Val Arg Pro Leu Asp Gly Gly Tyr Ala Asn Gly Tyr Gly Asn
945                 950                 955                 960

Ser Lys Trp Ala Gly Glu Val Leu Leu Arg Glu Ala His Asp Leu Cys
        965                 970                 975

Gly Leu Pro Val Ala Thr Phe Arg Ser Asp Met Ile Leu Ala His Pro
            980                 985                 990

Arg Tyr Arg Gly Gln Val Asn Val Pro Asp Met Phe Thr Arg Leu Leu
            995                 1000                1005

Leu Ser Leu Leu Ile Thr Gly Val Ala Pro Arg Ser Phe Tyr Ile
    1010                1015                1020

Gly Asp Gly Glu Arg Pro Arg Ala His Tyr Pro Gly Leu Thr Val
    1025                1030                1035

Asp Phe Val Ala Glu Ala Val Thr Thr Leu Gly Ala Gln Gln Arg
    1040                1045                1050

Glu Gly Tyr Val Ser Tyr Asp Val Met Asn Pro His Asp Asp Gly
    1055                1060                1065

Ile Ser Leu Asp Val Phe Val Asp Trp Leu Ile Arg Ala Gly His
    1070                1075                1080

Pro Ile Asp Arg Val Asp Tyr Asp Asp Trp Val Arg Arg Phe
    1085                1090                1095

Glu Thr Ala Leu Thr Ala Leu Pro Glu Lys Arg Arg Ala Gln Thr
    1100                1105                1110

Val Leu Pro Leu Leu His Ala Phe Arg Ala Pro Gln Ala Pro Leu
    1115                1120                1125

Arg Gly Ala Pro Glu Pro Thr Glu Val Phe His Ala Ala Val Arg
    1130                1135                1140

Thr Ala Lys Val Gly Pro Gly Asp Ile Pro His Leu Asp Glu Ala
    1145                1150                1155

Leu Ile Asp Lys Tyr Ile Arg Asp Leu Arg Glu Phe Gly Leu Ile
    1160                1165                1170

<210> SEQ ID NO 4
<211> LENGTH: 1148
<212> TYPE: PRT
<213> ORGANISM: Segniliparus rugosus

<400> SEQUENCE: 4

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu Ala His
    50                  55                  60

Arg Val Gly Ala Gly Tyr Glu Thr Ile Ser Tyr Gly Glu Leu Trp Ala
65                  70                  75                  80

```
Arg Val Gly Ala Ile Ala Ala Ala Trp Gln Ala Asp Gly Leu Ala Pro
                 85                  90                  95
Gly Asp Phe Val Ala Thr Val Gly Phe Thr Ser Pro Asp Tyr Val Ala
            100                 105                 110
Val Asp Leu Ala Ala Ala Arg Ser Gly Leu Val Ser Val Pro Leu Gln
        115                 120                 125
Ala Gly Ala Ser Leu Ala Gln Leu Val Gly Ile Leu Glu Glu Thr Glu
    130                 135                 140
Pro Lys Val Leu Ala Ala Ser Ala Ser Ser Leu Glu Gly Ala Val Ala
145                 150                 155                 160
Cys Ala Leu Ala Ala Pro Ser Val Gln Arg Leu Val Val Phe Asp Leu
                165                 170                 175
Arg Gly Pro Asp Ala Ser Glu Ser Ala Ala Asp Glu Arg Arg Gly Ala
            180                 185                 190
Leu Ala Asp Ala Glu Glu Gln Leu Ala Arg Ala Gly Arg Ala Val Val
        195                 200                 205
Val Glu Thr Leu Ala Asp Leu Ala Ala Arg Gly Glu Ala Leu Pro Glu
    210                 215                 220
Ala Pro Leu Phe Glu Pro Ala Glu Gly Glu Asp Pro Leu Ala Leu Leu
225                 230                 235                 240
Ile Tyr Thr Ser Gly Ser Thr Gly Ala Pro Lys Gly Ala Met Tyr Ser
                245                 250                 255
Gln Arg Leu Val Ser Gln Leu Trp Gly Arg Thr Pro Val Val Pro Gly
            260                 265                 270
Met Pro Asn Ile Ser Leu His Tyr Met Pro Leu Ser His Ser Tyr Gly
        275                 280                 285
Arg Ala Val Leu Ala Gly Ala Leu Ser Ala Gly Gly Thr Ala His Phe
    290                 295                 300
Thr Ala Asn Ser Asp Leu Ser Thr Leu Phe Glu Asp Ile Ala Leu Ala
305                 310                 315                 320
Arg Pro Thr Phe Leu Ala Leu Val Pro Arg Val Cys Glu Met Leu Phe
                325                 330                 335
Gln Glu Ser Gln Arg Gly Gln Asp Val Ala Glu Leu Arg Glu Arg Val
            340                 345                 350
Leu Gly Gly Arg Leu Leu Val Ala Val Cys Gly Ser Ala Pro Leu Ser
        355                 360                 365
Pro Glu Met Arg Ala Phe Met Glu Glu Val Leu Gly Phe Pro Leu Leu
    370                 375                 380
Asp Gly Tyr Gly Ser Thr Glu Ala Leu Gly Val Met Arg Asn Gly Ile
385                 390                 395                 400
Ile Gln Arg Pro Pro Val Ile Asp Tyr Lys Leu Val Asp Val Pro Glu
                405                 410                 415
Leu Gly Tyr Arg Thr Thr Asp Lys Pro Tyr Pro Arg Gly Glu Leu Cys
            420                 425                 430
Ile Arg Ser Thr Ser Leu Ile Ser Gly Tyr Tyr Lys Arg Pro Glu Ile
        435                 440                 445
Thr Ala Glu Val Phe Asp Ala Gln Gly Tyr Tyr Lys Thr Gly Asp Val
    450                 455                 460
Met Ala Glu Ile Ala Pro Asp His Leu Val Tyr Val Asp Arg Ser Lys
465                 470                 475                 480
Asn Val Leu Lys Leu Ser Gln Gly Glu Phe Val Ala Val Ala Lys Leu
                485                 490                 495
```

```
Glu Ala Ala Tyr Gly Thr Ser Pro Tyr Val Lys Gln Ile Phe Val Tyr
                500                 505                 510

Gly Asn Ser Glu Arg Ser Phe Leu Leu Ala Val Val Pro Asn Ala
            515                 520                 525

Glu Val Leu Gly Ala Arg Asp Gln Glu Ala Lys Pro Leu Ile Ala
    530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
            580                 585                 590

Arg Tyr Gly Glu Ala Leu Glu Ala Arg Tyr Asp Glu Ile Ala His Gly
    595                 600                 605

Gln Ala Asp Glu Leu Arg Ala Leu Arg Asp Gly Ala Gly Gln Arg Pro
    610                 615                 620

Val Val Glu Thr Val Val Arg Ala Ala Val Ala Ile Ser Gly Ser Glu
625                 630                 635                 640

Gly Ala Glu Val Gly Pro Glu Ala Asn Phe Ala Asp Leu Gly Gly Asp
                645                 650                 655

Ser Leu Ser Ala Leu Ser Leu Ala Asn Leu Leu His Asp Val Phe Glu
            660                 665                 670

Val Glu Val Pro Val Arg Ile Ile Ile Gly Pro Thr Ala Ser Leu Ala
    675                 680                 685

Gly Ile Ala Lys His Ile Glu Ala Glu Arg Ala Gly Ala Ser Ala Pro
    690                 695                 700

Thr Ala Ala Ser Val His Gly Ala Gly Ala Thr Arg Ile Arg Ala Ser
705                 710                 715                 720

Glu Leu Thr Leu Glu Lys Phe Leu Pro Glu Asp Leu Leu Ala Ala Ala
                725                 730                 735

Lys Gly Leu Pro Ala Ala Asp Gln Val Arg Thr Val Leu Leu Thr Gly
            740                 745                 750

Ala Asn Gly Trp Leu Gly Arg Phe Leu Ala Leu Glu Gln Leu Glu Arg
    755                 760                 765

Leu Ala Arg Ser Gly Gln Asp Gly Gly Lys Leu Ile Cys Leu Val Arg
    770                 775                 780

Gly Lys Asp Ala Ala Ala Arg Arg Arg Ile Glu Glu Thr Leu Gly
785                 790                 795                 800

Thr Asp Pro Ala Leu Ala Ala Arg Phe Ala Glu Leu Ala Glu Gly Arg
                805                 810                 815

Leu Glu Val Val Pro Gly Asp Val Gly Glu Pro Lys Phe Gly Leu Asp
            820                 825                 830

Asp Ala Ala Trp Asp Arg Leu Ala Glu Glu Val Asp Val Ile Val His
    835                 840                 845

Pro Ala Ala Leu Val Asn His Val Leu Pro Tyr His Gln Leu Phe Gly
    850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
                885                 890                 895

Val Glu Pro Ser Ser Phe Glu Asp Gly Asp Ile Arg Ala Val Val
            900                 905                 910

Pro Glu Arg Pro Leu Gly Asp Gly Tyr Ala Asn Gly Tyr Gly Asn Ser
```

```
            915                 920                 925
Lys Trp Ala Gly Glu Val Leu Leu Arg Glu Ala His Glu Leu Val Gly
    930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
                965                 970                 975

Ser Leu Leu Ala Thr Gly Ile Ala Pro Lys Ser Phe Tyr Gln Gln Gly
            980                 985                 990

Ala Ala Gly Glu Arg Gln Arg Ala His Tyr Asp Gly Ile Pro Val Asp
        995                 1000                1005

Phe Thr Ala Glu Ala Ile Thr Thr Leu Gly Ala Glu Pro Ser Trp
    1010                1015                1020

Phe Asp Gly Gly Ala Gly Phe Arg Ser Phe Asp Val Phe Asn Pro
    1025                1030                1035

His His Asp Gly Val Gly Leu Asp Glu Phe Val Asp Trp Leu Ile
    1040                1045                1050

Glu Ala Gly His Pro Ile Ser Arg Ile Asp Asp His Lys Glu Trp
    1055                1060                1065

Phe Ala Arg Phe Glu Thr Ala Val Arg Gly Leu Pro Glu Ala Gln
    1070                1075                1080

Arg Gln His Ser Leu Leu Pro Leu Leu Arg Ala Tyr Ser Phe Pro
    1085                1090                1095

His Pro Pro Val Asp Gly Ser Val Tyr Pro Thr Gly Lys Phe Gln
    1100                1105                1110

Gly Ala Val Lys Ala Ala Gln Val Gly Ser Asp His Asp Val Pro
    1115                1120                1125

His Leu Gly Lys Ala Leu Ile Val Lys Tyr Ala Asp Asp Leu Lys
    1130                1135                1140

Ala Leu Gly Leu Leu
    1145

<210> SEQ ID NO 5
<211> LENGTH: 1168
<212> TYPE: PRT
<213> ORGANISM: Mycobacterium smegmatis

<400> SEQUENCE: 5

Met Thr Ile Glu Thr Arg Glu Asp Arg Phe Asn Arg Arg Ile Asp His
1               5                   10                  15

Leu Phe Glu Thr Asp Pro Gln Phe Ala Ala Arg Pro Asp Glu Ala
            20                  25                  30

Ile Ser Ala Ala Ala Asp Pro Glu Leu Arg Leu Pro Ala Ala Val
        35                  40                  45

Lys Gln Ile Leu Ala Gly Tyr Ala Asp Arg Pro Ala Leu Gly Lys Arg
    50                  55                  60

Ala Val Glu Phe Val Thr Asp Glu Glu Gly Arg Thr Ala Lys Leu
65                  70                  75                  80

Leu Pro Arg Phe Asp Thr Ile Thr Tyr Arg Gln Leu Ala Gly Arg Ile
                85                  90                  95

Gln Ala Val Thr Asn Ala Trp His Asn His Pro Val Asn Ala Gly Asp
            100                 105                 110

Arg Val Ala Ile Leu Gly Phe Thr Ser Val Asp Tyr Thr Thr Ile Asp
        115                 120                 125
```

```
Ile Ala Leu Leu Glu Leu Gly Ala Val Ser Val Pro Leu Gln Thr Ser
    130                 135                 140
Ala Pro Val Ala Gln Leu Gln Pro Ile Val Ala Glu Thr Glu Pro Lys
145                 150                 155                 160
Val Ile Ala Ser Ser Val Asp Phe Leu Ala Asp Ala Val Ala Leu Val
                165                 170                 175
Glu Ser Gly Pro Ala Pro Ser Arg Leu Val Val Phe Asp Tyr Ser His
            180                 185                 190
Glu Val Asp Asp Gln Arg Glu Ala Phe Glu Ala Ala Lys Gly Lys Leu
        195                 200                 205
Ala Gly Thr Gly Val Val Glu Thr Ile Thr Asp Ala Leu Asp Arg
    210                 215                 220
Gly Arg Ser Leu Ala Asp Ala Pro Leu Tyr Val Pro Asp Glu Ala Asp
225                 230                 235                 240
Pro Leu Thr Leu Leu Ile Tyr Thr Ser Gly Ser Thr Gly Thr Pro Lys
                245                 250                 255
Gly Ala Met Tyr Pro Glu Ser Lys Thr Ala Thr Met Trp Gln Ala Gly
            260                 265                 270
Ser Lys Ala Arg Trp Asp Glu Thr Leu Gly Val Met Pro Ser Ile Thr
        275                 280                 285
Leu Asn Phe Met Pro Met Ser His Val Met Gly Arg Gly Ile Leu Cys
    290                 295                 300
Ser Thr Leu Ala Ser Gly Gly Thr Ala Tyr Phe Ala Ala Arg Ser Asp
305                 310                 315                 320
Leu Ser Thr Phe Leu Glu Asp Leu Ala Leu Val Arg Pro Thr Gln Leu
                325                 330                 335
Asn Phe Val Pro Arg Ile Trp Asp Met Leu Phe Gln Glu Tyr Gln Ser
            340                 345                 350
Arg Leu Asp Asn Arg Arg Ala Glu Gly Ser Glu Asp Arg Ala Glu Ala
        355                 360                 365
Ala Val Leu Glu Glu Val Arg Thr Gln Leu Leu Gly Gly Arg Phe Val
    370                 375                 380
Ser Ala Leu Thr Gly Ser Ala Pro Ile Ser Ala Glu Met Lys Ser Trp
385                 390                 395                 400
Val Glu Asp Leu Leu Asp Met His Leu Leu Glu Gly Tyr Gly Ser Thr
                405                 410                 415
Glu Ala Gly Ala Val Phe Ile Asp Gly Gln Ile Gln Arg Pro Pro Val
            420                 425                 430
Ile Asp Tyr Lys Leu Val Asp Val Pro Asp Leu Gly Tyr Phe Ala Thr
        435                 440                 445
Asp Arg Pro Tyr Pro Arg Gly Glu Leu Leu Val Lys Ser Glu Gln Met
    450                 455                 460
Phe Pro Gly Tyr Tyr Lys Arg Pro Glu Ile Thr Ala Glu Met Phe Asp
465                 470                 475                 480
Glu Asp Gly Tyr Tyr Arg Thr Gly Asp Ile Val Ala Glu Leu Gly Pro
                485                 490                 495
Asp His Leu Glu Tyr Leu Asp Arg Arg Asn Asn Val Leu Lys Leu Ser
            500                 505                 510
Gln Gly Glu Phe Val Thr Val Ser Lys Leu Glu Ala Val Phe Gly Asp
        515                 520                 525
Ser Pro Leu Val Arg Gln Ile Tyr Val Tyr Gly Asn Ser Ala Arg Ser
    530                 535                 540
Tyr Leu Leu Ala Val Val Val Pro Thr Glu Glu Ala Leu Ser Arg Trp
```

```
        545                 550                 555                 560
Asp Gly Asp Glu Leu Lys Ser Arg Ile Ser Asp Ser Leu Gln Asp Ala
                565                 570                 575

Ala Arg Ala Ala Gly Leu Gln Ser Tyr Glu Ile Pro Arg Asp Phe Leu
                580                 585                 590

Val Glu Thr Thr Pro Phe Thr Leu Glu Asn Gly Leu Leu Thr Gly Ile
                595                 600                 605

Arg Lys Leu Ala Arg Pro Lys Leu Lys Ala His Tyr Gly Glu Arg Leu
                610                 615                 620

Glu Gln Leu Tyr Thr Asp Leu Ala Glu Gly Gln Ala Asn Glu Leu Arg
625                 630                 635                 640

Glu Leu Arg Arg Asn Gly Ala Asp Arg Pro Val Val Glu Thr Val Ser
                645                 650                 655

Arg Ala Ala Val Ala Leu Leu Gly Ala Ser Val Thr Asp Leu Arg Ser
                660                 665                 670

Asp Ala His Phe Thr Asp Leu Gly Gly Asp Ser Leu Ser Ala Leu Ser
                675                 680                 685

Phe Ser Asn Leu Leu His Glu Ile Phe Asp Val Asp Val Pro Val Gly
                690                 695                 700

Val Ile Val Ser Pro Ala Thr Asp Leu Ala Gly Val Ala Ala Tyr Ile
705                 710                 715                 720

Glu Gly Glu Leu Arg Gly Ser Lys Arg Pro Thr Tyr Ala Ser Val His
                725                 730                 735

Gly Arg Asp Ala Thr Glu Val Arg Ala Arg Asp Leu Ala Leu Gly Lys
                740                 745                 750

Phe Ile Asp Ala Lys Thr Leu Ser Ala Ala Pro Gly Leu Pro Arg Ser
                755                 760                 765

Gly Thr Glu Ile Arg Thr Val Leu Leu Thr Gly Ala Thr Gly Phe Leu
                770                 775                 780

Gly Arg Tyr Leu Ala Leu Glu Trp Leu Glu Arg Met Asp Leu Val Asp
785                 790                 795                 800

Gly Lys Val Ile Cys Leu Val Arg Ala Arg Ser Asp Asp Glu Ala Arg
                805                 810                 815

Ala Arg Leu Asp Ala Thr Phe Asp Thr Gly Asp Ala Thr Leu Leu Glu
                820                 825                 830

His Tyr Arg Ala Leu Ala Ala Asp His Leu Glu Val Ile Ala Gly Asp
                835                 840                 845

Lys Gly Glu Ala Asp Leu Gly Leu Asp His Asp Thr Trp Gln Arg Leu
                850                 855                 860

Ala Asp Thr Val Asp Leu Ile Val Asp Pro Ala Ala Leu Val Asn His
865                 870                 875                 880

Val Leu Pro Tyr Ser Gln Met Phe Gly Pro Asn Ala Leu Gly Thr Ala
                885                 890                 895

Glu Leu Ile Arg Ile Ala Leu Thr Thr Thr Ile Lys Pro Tyr Val Tyr
                900                 905                 910

Val Ser Thr Ile Gly Val Gly Gln Gly Ile Ser Pro Glu Ala Phe Val
                915                 920                 925

Glu Asp Ala Asp Ile Arg Glu Ile Ser Ala Thr Arg Arg Val Asp Asp
                930                 935                 940

Ser Tyr Ala Asn Gly Tyr Gly Asn Ser Lys Trp Ala Gly Glu Val Leu
945                 950                 955                 960

Leu Arg Glu Ala His Asp Trp Cys Gly Leu Pro Val Ser Val Phe Arg
                965                 970                 975
```

```
Cys Asp Met Ile Leu Ala Asp Thr Thr Tyr Ser Gly Gln Leu Asn Leu
            980                 985                 990

Pro Asp Met Phe Thr Arg Leu Met  Leu Ser Leu Val Ala  Thr Gly Ile
            995                1000                1005

Ala Pro  Gly Ser Phe Tyr Glu  Leu Asp Ala Asp Gly  Asn Arg Gln
        1010                1015                1020

Arg Ala  His Tyr Asp Gly Leu  Pro Val Glu Phe Ile  Ala Glu Ala
        1025                1030                1035

Ile Ser  Thr Ile Gly Ser Gln  Val Thr Asp Gly Phe  Glu Thr Phe
        1040                1045                1050

His Val  Met Asn Pro Tyr Asp  Asp Gly Ile Gly Leu  Asp Glu Tyr
        1055                1060                1065

Val Asp  Trp Leu Ile Glu Ala  Gly Tyr Pro Val His  Arg Val Asp
        1070                1075                1080

Asp Tyr  Ala Thr Trp Leu Ser  Arg Phe Glu Thr Ala  Leu Arg Ala
        1085                1090                1095

Leu Pro  Glu Arg Gln Arg Gln  Ala Ser Leu Leu Pro  Leu Leu His
        1100                1105                1110

Asn Tyr  Gln Gln Pro Ser Pro  Pro Val Cys Gly Ala  Met Ala Pro
        1115                1120                1125

Thr Asp  Arg Phe Arg Ala Ala  Val Gln Asp Ala Lys  Ile Gly Pro
        1130                1135                1140

Asp Lys  Asp Ile Pro His Val  Thr Ala Asp Val Ile  Val Lys Tyr
        1145                1150                1155

Ile Ser  Asn Leu Gln Met Leu  Gly Leu Leu
        1160                1165

<210> SEQ ID NO 6
<211> LENGTH: 1185
<212> TYPE: PRT
<213> ORGANISM: Mycobacterium massiliense

<400> SEQUENCE: 6

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
            35                  40                  45

Ala Ile Ala Ala Leu Met Thr Gly Tyr Ala Glu Arg Pro Ala Leu Gly
        50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Gly Val Ala Val
        130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
```

-continued

```
                165                 170                 175
Ala Met Glu Ser Val Arg Ala Thr Pro Ser Ile Lys Gln Val Val
                180                 185                 190

Phe Asp Tyr Thr Pro Glu Val Asp Asp Gln Arg Glu Ala Phe Glu Ala
            195                 200                 205

Ala Ser Thr Gln Leu Ala Gly Thr Gly Ile Ala Leu Glu Thr Leu Asp
        210                 215                 220

Ala Val Ile Ala Arg Gly Ala Leu Pro Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met His Ser Glu Asn Ile Val Arg
                260                 265                 270

Arg Trp Trp Ile Arg Glu Asp Val Met Ala Gly Thr Glu Asn Leu Pro
                275                 280                 285

Met Ile Gly Leu Asn Phe Met Pro Met Ser His Ile Met Gly Arg Gly
                290                 295                 300

Thr Leu Thr Ser Thr Leu Ser Thr Gly Gly Thr Gly Tyr Phe Ala Ala
305                 310                 315                 320

Ser Ser Asp Met Ser Thr Leu Phe Glu Asp Met Glu Leu Ile Arg Pro
                325                 330                 335

Thr Ala Leu Ala Leu Val Pro Arg Val Cys Asp Met Val Phe Gln Arg
                340                 345                 350

Phe Gln Thr Glu Val Asp Arg Arg Leu Ala Ser Gly Asp Thr Ala Ser
                355                 360                 365

Ala Glu Ala Val Ala Ala Glu Val Lys Ala Asp Ile Arg Asp Asn Leu
                370                 375                 380

Phe Gly Gly Arg Val Ser Ala Val Met Val Gly Ser Ala Pro Leu Ser
385                 390                 395                 400

Glu Glu Leu Gly Glu Phe Ile Glu Ser Cys Phe Glu Leu Asn Leu Thr
                405                 410                 415

Asp Gly Tyr Gly Ser Thr Glu Ala Gly Met Val Phe Arg Asp Gly Ile
                420                 425                 430

Val Gln Arg Pro Pro Val Ile Asp Tyr Lys Leu Val Asp Val Pro Glu
                435                 440                 445

Leu Gly Tyr Phe Ser Thr Asp Lys Pro His Pro Arg Gly Glu Leu Leu
                450                 455                 460

Leu Lys Thr Asp Gly Met Phe Leu Gly Tyr Tyr Lys Arg Pro Glu Val
465                 470                 475                 480

Thr Ala Ser Val Phe Asp Ala Asp Gly Phe Tyr Met Thr Gly Asp Ile
                485                 490                 495

Val Ala Glu Leu Ala His Asp Asn Ile Glu Ile Asp Arg Arg Asn
                500                 505                 510

Asn Val Leu Lys Leu Ser Gln Gly Glu Phe Val Ala Val Ala Thr Leu
                515                 520                 525

Glu Ala Glu Tyr Ala Asn Ser Pro Val Val His Gln Ile Tyr Val Tyr
                530                 535                 540

Gly Ser Ser Glu Arg Ser Tyr Leu Leu Ala Val Val Pro Thr Pro
545                 550                 555                 560

Glu Ala Val Ala Ala Ala Lys Gly Asp Ala Ala Ala Leu Lys Thr Thr
                565                 570                 575

Ile Ala Asp Ser Leu Gln Asp Ile Ala Lys Glu Ile Gln Leu Gln Ser
                580                 585                 590
```

```
Tyr Glu Val Pro Arg Asp Phe Ile Ile Glu Pro Gln Pro Phe Thr Gln
        595                 600                 605

Gly Asn Gly Leu Leu Thr Gly Ile Ala Lys Leu Ala Arg Pro Asn Leu
    610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
                660                 665                 670

Val Ser Ser Ala Glu Leu Ala Ala Asp Ala His Phe Thr Asp Leu Gly
            675                 680                 685

Gly Asp Ser Leu Ser Ala Leu Ser Phe Ser Asp Leu Leu Arg Asp Ile
        690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
        755                 760                 765

His Ala Ala Pro Ser Leu Pro Lys Ala Ala Gly Ile Pro His Thr Val
770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
            820                 825                 830

Asp Thr Gly Asp Thr Glu Leu Leu Ala His Phe Arg Ser Leu Ala Asp
        835                 840                 845

Lys His Leu Glu Val Leu Ala Gly Asp Ile Gly Asp Pro Asn Leu Gly
    850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
            900                 905                 910

Thr Thr Lys Ile Lys Pro Val Thr Tyr Leu Ser Thr Val Ala Val Ala
        915                 920                 925

Ala Tyr Val Asp Pro Thr Thr Phe Asp Glu Glu Ser Asp Ile Arg Leu
    930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
            980                 985                 990

Ser Arg Tyr Thr Gly Gln Leu Asn Val Pro Asp Gln Phe Thr Arg Leu
        995                 1000                1005
```

```
Ile Leu Ser Leu Ile Ala Thr Gly Ile Ala Pro Gly Ser Phe Tyr
    1010                1015                1020

Gln Ala Gln Thr Thr Gly Glu Arg Pro Leu Ala His Tyr Asp Gly
    1025                1030                1035

Leu Pro Gly Asp Phe Thr Ala Glu Ala Ile Thr Thr Leu Gly Thr
    1040                1045                1050

Gln Val Pro Glu Gly Ser Glu Gly Phe Val Thr Tyr Asp Cys Val
    1055                1060                1065

Asn Pro His Ala Asp Gly Ile Ser Leu Asp Asn Phe Val Asp Trp
    1070                1075                1080

Leu Ile Glu Ala Gly Tyr Pro Ile Ala Arg Ile Asp Asn Tyr Thr
    1085                1090                1095

Glu Trp Phe Thr Arg Phe Asp Thr Ala Ile Arg Gly Leu Ser Glu
    1100                1105                1110

Lys Gln Lys Gln His Ser Leu Leu Pro Leu Leu His Ala Phe Glu
    1115                1120                1125

Gln Pro Ser Ala Ala Glu Asn His Gly Val Val Pro Ala Lys Arg
    1130                1135                1140

Phe Gln His Ala Val Gln Ala Ala Gly Ile Gly Pro Val Gly Gln
    1145                1150                1155

Asp Gly Thr Thr Asp Ile Pro His Leu Ser Arg Arg Leu Ile Val
    1160                1165                1170

Lys Tyr Ala Lys Asp Leu Glu Gln Leu Gly Leu Leu
    1175                1180                1185
```

<210> SEQ ID NO 7
<211> LENGTH: 1186
<212> TYPE: PRT
<213> ORGANISM: Segniliparus rotundus

<400> SEQUENCE: 7

```
Met Thr Gln Ser His Thr Gln Gly Pro Gln Ala Ser Ala His Ser
1               5                   10                  15

Arg Leu Ala Arg Arg Ala Ala Glu Leu Leu Ala Thr Asp Pro Gln Ala
                20                  25                  30

Ala Ala Thr Leu Pro Asp Pro Glu Val Val Arg Gln Ala Thr Arg Pro
            35                  40                  45

Gly Leu Arg Leu Ala Glu Arg Val Asp Ala Ile Leu Ser Gly Tyr Ala
        50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190
```

-continued

```
Ser Val Arg Arg Leu Leu Val Phe Asp Tyr Arg Ala Gly Ser Asp Glu
        195                 200                 205
Asp Arg Glu Ala Val Glu Ala Ala Lys Arg Lys Ile Ala Asp Ala Gly
    210                 215                 220
Ser Ser Val Leu Val Asp Val Leu Asp Glu Val Ile Ala Arg Gly Lys
225                 230                 235                 240
Ser Ala Pro Lys Ala Pro Leu Pro Pro Ala Thr Asp Ala Gly Asp Asp
                245                 250                 255
Ser Leu Ser Leu Leu Ile Tyr Thr Ser Gly Ser Thr Gly Thr Pro Lys
            260                 265                 270
Gly Ala Met Tyr Pro Glu Arg Asn Val Ala His Phe Trp Gly Gly Val
        275                 280                 285
Trp Ala Ala Ala Phe Asp Glu Asp Ala Ala Pro Pro Val Pro Ala Ile
    290                 295                 300
Asn Ile Thr Phe Leu Pro Leu Ser His Val Ala Ser Arg Leu Ser Leu
305                 310                 315                 320
Met Pro Thr Leu Ala Arg Gly Gly Leu Met His Phe Val Ala Lys Ser
                325                 330                 335
Asp Leu Ser Thr Leu Phe Glu Asp Leu Lys Leu Ala Arg Pro Thr Asn
            340                 345                 350
Leu Phe Leu Val Pro Arg Val Val Glu Met Leu Tyr Gln His Tyr Gln
        355                 360                 365
Ser Glu Leu Asp Arg Arg Gly Val Gln Asp Gly Thr Arg Glu Ala Glu
    370                 375                 380
Ala Val Lys Asp Asp Leu Arg Thr Gly Leu Leu Gly Gly Arg Ile Leu
385                 390                 395                 400
Thr Ala Gly Phe Gly Ser Ala Pro Leu Ser Ala Glu Leu Ala Gly Phe
                405                 410                 415
Ile Glu Ser Leu Leu Gln Ile His Leu Val Asp Gly Tyr Gly Ser Thr
            420                 425                 430
Glu Ala Gly Pro Val Trp Arg Asp Gly Tyr Leu Val Lys Pro Pro Val
        435                 440                 445
Thr Asp Tyr Lys Leu Ile Asp Val Pro Glu Leu Gly Tyr Phe Ser Thr
    450                 455                 460
Asp Ser Pro His Pro Arg Gly Glu Leu Ala Ile Lys Thr Gln Thr Ile
465                 470                 475                 480
Leu Pro Gly Tyr Tyr Lys Arg Pro Glu Thr Thr Ala Glu Val Phe Asp
                485                 490                 495
Glu Asp Gly Phe Tyr Leu Thr Gly Asp Val Val Ala Gln Ile Gly Pro
            500                 505                 510
Glu Gln Phe Ala Tyr Val Asp Arg Arg Lys Asn Val Leu Lys Leu Ser
        515                 520                 525
Gln Gly Glu Phe Val Thr Leu Ala Lys Leu Glu Ala Ala Tyr Ser Ser
    530                 535                 540
Ser Pro Leu Val Arg Gln Leu Phe Val Tyr Gly Ser Ser Glu Arg Ser
545                 550                 555                 560
Tyr Leu Leu Ala Val Ile Val Pro Thr Pro Asp Ala Leu Lys Lys Phe
                565                 570                 575
Gly Val Gly Glu Ala Ala Lys Ala Ala Leu Gly Glu Ser Leu Gln Lys
            580                 585                 590
Ile Ala Arg Asp Glu Gly Leu Gln Ser Tyr Glu Val Pro Arg Asp Phe
        595                 600                 605
```

-continued

```
Ile Ile Glu Thr Asp Pro Phe Thr Val Glu Asn Gly Leu Leu Ser Asp
610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
                645                 650                 655

Arg Asp Ile Arg Arg Gly Val Gln Gln Arg Pro Thr Leu Glu Thr Val
            660                 665                 670

Arg Arg Ala Ala Ala Met Leu Gly Ala Ser Ala Ala Glu Ile Lys
                675                 680                 685

Pro Asp Ala His Phe Thr Asp Leu Gly Gly Asp Ser Leu Ser Ala Leu
690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
                725                 730                 735

Ile Asp Ala Gln Leu Ala Gly Gly Arg Ala Arg Pro Thr Phe Ala Thr
                740                 745                 750

Val His Gly Lys Gly Ser Thr Thr Ile Lys Ala Ser Asp Leu Thr Leu
        755                 760                 765

Asp Lys Phe Ile Asp Glu Gln Thr Leu Glu Ala Ala Lys His Leu Pro
770                 775                 780

Lys Pro Ala Asp Pro Pro Arg Thr Val Leu Leu Thr Gly Ala Asn Gly
785                 790                 795                 800

Trp Leu Gly Arg Phe Leu Ala Leu Glu Trp Leu Glu Arg Leu Ala Pro
                805                 810                 815

Ala Gly Gly Lys Leu Ile Thr Ile Val Arg Gly Lys Asp Ala Ala Gln
        820                 825                 830

Ala Lys Ala Arg Leu Asp Ala Ala Tyr Glu Ser Gly Asp Pro Lys Leu
        835                 840                 845

Ala Gly His Tyr Gln Asp Leu Ala Ala Thr Thr Leu Glu Val Leu Ala
        850                 855                 860

Gly Asp Phe Ser Glu Pro Arg Leu Gly Leu Asp Glu Ala Thr Trp Asn
865                 870                 875                 880

Arg Leu Ala Asp Glu Val Asp Phe Ile Ser His Pro Gly Ala Leu Val
                885                 890                 895

Asn His Val Leu Pro Tyr Asn Gln Leu Phe Gly Pro Asn Val Ala Gly
            900                 905                 910

Val Ala Glu Ile Ile Lys Leu Ala Ile Thr Thr Arg Ile Lys Pro Val
        915                 920                 925

Thr Tyr Leu Ser Thr Val Ala Val Ala Ala Gly Val Glu Pro Ser Ala
    930                 935                 940

Leu Asp Glu Asp Gly Asp Ile Arg Thr Val Ser Ala Glu Arg Ser Val
945                 950                 955                 960

Asp Glu Gly Tyr Ala Asn Gly Tyr Gly Asn Ser Lys Trp Gly Gly Glu
                965                 970                 975

Val Leu Leu Arg Glu Ala His Asp Arg Thr Gly Leu Pro Val Arg Val
                980                 985                 990

Phe Arg Ser Asp Met Ile Leu Ala His Gln Lys Tyr Thr Gly Gln Val
            995                 1000                1005

Asn Ala Thr Asp Gln Phe Thr Arg Leu Val Gln Ser Leu Leu Ala
        1010                1015                1020

Thr Gly Leu Ala Pro Lys Ser Phe Tyr Glu Leu Asp Ala Gln Gly
```

-continued

```
                    1025                1030                1035

Asn Arg  Gln Arg Ala His Tyr  Asp Gly Ile Pro Val  Asp Phe Thr
        1040             1045             1050

Ala Glu  Ser Ile Thr Thr Leu  Gly Gly Asp Gly Leu  Glu Gly Tyr
        1055             1060             1065

Arg Ser  Tyr Asn Val Phe Asn  Pro His Arg Asp Gly  Val Gly Leu
        1070             1075             1080

Asp Glu  Phe Val Asp Trp Leu  Ile Glu Ala Gly His  Pro Ile Thr
        1085             1090             1095

Arg Ile  Asp Asp Tyr Asp Gln  Trp Leu Ser Arg Phe  Glu Thr Ser
        1100             1105             1110

Leu Arg  Gly Leu Pro Glu Ser  Lys Arg Gln Ala Ser  Val Leu Pro
        1115             1120             1125

Leu Leu  His Ala Phe Ala Arg  Pro Gly Pro Ala Val  Asp Gly Ser
        1130             1135             1140

Pro Phe  Arg Asn Thr Val Phe  Arg Thr Asp Val Gln  Lys Ala Lys
        1145             1150             1155

Ile Gly  Ala Glu His Asp Ile  Pro His Leu Gly Lys  Ala Leu Val
        1160             1165             1170

Leu Lys  Tyr Ala Asp Asp Ile  Lys Gln Leu Gly Leu  Leu
        1175             1180             1185
```

<210> SEQ ID NO 8
<211> LENGTH: 459
<212> TYPE: PRT
<213> ORGANISM: Chromobacterium violaceum

<400> SEQUENCE: 8

```
Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205
```

Glu Glu Lys Ile Leu Glu Ile Gly Ala Asp Lys Val Ala Ala Phe Val
210                 215                 220

Gly Glu Pro Ile Gln Gly Ala Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
260                 265                 270

Gly His Gln His Phe Gly Phe Gln Pro Asp Leu Phe Thr Ala Ala Lys
            275                 280                 285

Gly Leu Ser Ser Gly Tyr Leu Pro Ile Gly Ala Val Phe Val Gly Lys
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455

<210> SEQ ID NO 9
<211> LENGTH: 468
<212> TYPE: PRT
<213> ORGANISM: Pseudomonas aeruginosa

<400> SEQUENCE: 9

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
                20                  25                  30

Asp His Arg Val Asn Gly Ser Leu Asn Ile Ala Ala Gly Asp Gly Ala
            35                  40                  45

Tyr Ile Tyr Asp Thr Ala Gly Asn Arg Tyr Leu Asp Ala Val Gly Gly
        50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

```
Ala Val Asp Thr Ala Ile Arg Leu Met His Tyr Tyr Gln Asn Cys Arg
            130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270

Gly Arg Leu Gly His Phe Phe Ala Ser Gln Ala Val Phe Gly Val Gln
        275                 280                 285

Pro Asp Ile Ile Leu Thr Ala Lys Gly Leu Thr Ser Gly Tyr Gln Pro
    290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
            340                 345                 350

Glu Gly Leu Leu Ala His Ala Asp Glu Val Gly Arg Tyr Phe Glu Glu
        355                 360                 365

Arg Leu Gln Ser Leu Arg Asp Leu Pro Ile Val Gly Asp Val Arg Gly
    370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
            420                 425                 430

Met Ser Pro Pro Leu Ile Leu Thr Arg Glu Gln Val Asp Thr Val Val
        435                 440                 445

Arg Val Leu Arg Glu Ser Ile Glu Glu Thr Val Glu Asp Leu Val Arg
    450                 455                 460

Ala Gly His Arg
465

<210> SEQ ID NO 10
<211> LENGTH: 454
<212> TYPE: PRT
<213> ORGANISM: Pseudomonas syringae

<400> SEQUENCE: 10

Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
```

```
            20                  25                  30
Gly Pro Arg Ile Ile Thr Arg Ala Glu Gly Val Tyr Leu Trp Asp Ser
            35                  40                  45
Glu Gly Asn Lys Ile Leu Asp Gly Met Ser Gly Leu Trp Cys Val Ala
        50                  55                  60
Ile Gly Tyr Gly Arg Glu Leu Ala Asp Ala Ala Ser Lys Gln Met
65                  70                  75                  80
Arg Glu Leu Pro Tyr Tyr Asn Leu Phe Phe Gln Thr Ala His Pro Pro
                85                  90                  95
Val Leu Glu Leu Ala Lys Ala Ile Ser Asp Ile Ala Pro Glu Gly Met
            100                 105                 110
Asn His Val Phe Phe Thr Gly Ser Gly Ser Glu Gly Asn Asp Thr Met
            115                 120                 125
Leu Arg Met Val Arg His Tyr Trp Ala Leu Lys Gly Gln Pro Asn Lys
            130                 135                 140
Lys Thr Ile Ile Ser Arg Val Asn Gly Tyr His Gly Ser Thr Val Ala
145                 150                 155                 160
Gly Ala Ser Leu Gly Gly Met Thr Tyr Met His Glu Gln Gly Asp Leu
                165                 170                 175
Pro Ile Pro Gly Val Val His Ile Pro Gln Pro Tyr Trp Phe Gly Glu
            180                 185                 190
Gly Gly Asp Met Thr Pro Asp Glu Phe Gly Ile Trp Ala Ala Glu Gln
            195                 200                 205
Leu Glu Lys Lys Ile Leu Glu Leu Gly Val Glu Asn Val Gly Ala Phe
            210                 215                 220
Ile Ala Glu Pro Ile Gln Gly Ala Gly Gly Val Ile Val Pro Pro Asp
225                 230                 235                 240
Ser Tyr Trp Pro Lys Ile Lys Glu Ile Leu Ser Arg Tyr Asp Ile Leu
                245                 250                 255
Phe Ala Ala Asp Glu Val Ile Cys Gly Phe Gly Arg Thr Ser Glu Trp
            260                 265                 270
Phe Gly Ser Asp Phe Tyr Gly Leu Arg Pro Asp Met Met Thr Ile Ala
            275                 280                 285
Lys Gly Leu Thr Ser Gly Tyr Val Pro Met Gly Gly Leu Ile Val Arg
            290                 295                 300
Asp Glu Ile Val Ala Val Leu Asn Glu Gly Gly Asp Phe Asn His Gly
305                 310                 315                 320
Phe Thr Tyr Ser Gly His Pro Val Ala Ala Val Ala Leu Glu Asn
                325                 330                 335
Ile Arg Ile Leu Arg Glu Glu Lys Ile Val Glu Arg Val Arg Ser Glu
            340                 345                 350
Thr Ala Pro Tyr Leu Gln Lys Arg Leu Arg Glu Leu Ser Asp His Pro
            355                 360                 365
Leu Val Gly Glu Val Arg Gly Val Gly Leu Leu Gly Ala Ile Glu Leu
            370                 375                 380
Val Lys Asp Lys Thr Thr Arg Glu Arg Tyr Thr Asp Lys Gly Ala Gly
385                 390                 395                 400
Met Ile Cys Arg Thr Phe Cys Phe Asp Asn Gly Leu Ile Met Arg Ala
                405                 410                 415
Val Gly Asp Thr Met Ile Ile Ala Pro Pro Leu Val Ile Ser Phe Ala
            420                 425                 430
Gln Ile Asp Glu Leu Val Glu Lys Ala Arg Thr Cys Leu Asp Leu Thr
            435                 440                 445
```

```
Leu Ala Val Leu Gln Gly
    450

<210> SEQ ID NO 11
<211> LENGTH: 467
<212> TYPE: PRT
<213> ORGANISM: Rhodobacter sphaeroides

<400> SEQUENCE: 11

Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys
    50                  55                  60

Ala Gln Val Gly Tyr Gly Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
            100                 105                 110

Leu Asn Arg Ile Phe Phe Thr Thr Gly Gly Ser Thr Ala Val Asp Ser
        115                 120                 125

Ala Leu Arg Phe Ser Glu Phe Tyr Asn Asn Val Leu Gly Arg Pro Gln
    130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
            180                 185                 190

Ala Gly Asn Arg Ser Gln Glu Ala Phe Leu Asp Asp Leu Val Gln Glu
        195                 200                 205

Phe Glu Asp Arg Ile Glu Ser Leu Gly Pro Asp Thr Ile Ala Ala Phe
    210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
            260                 265                 270

Phe Ala Ser Glu Lys Val Phe Gly Val Pro Asp Ile Ile Thr Phe
        275                 280                 285

Ala Lys Gly Val Thr Ser Gly Tyr Val Pro Leu Gly Gly Leu Ala Ile
    290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
            340                 345                 350

Gln Ala Arg Glu Met Ala Asp Tyr Phe Ala Ala Ala Leu Ala Ser Leu
```

```
                355                 360                 365
Arg Asp Leu Pro Gly Val Ala Glu Thr Arg Ser Val Gly Leu Val Gly
    370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
            420                 425                 430

Ile Ile Ser Arg Ala Gln Ile Asp Glu Met Val Ala Ile Met Arg Gln
        435                 440                 445

Ala Ile Thr Glu Val Ser Ala Ala His Gly Leu Thr Ala Lys Glu Pro
    450                 455                 460

Ala Ala Val
465

<210> SEQ ID NO 12
<211> LENGTH: 459
<212> TYPE: PRT
<213> ORGANISM: Escherichia coli

<400> SEQUENCE: 12

Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
        115                 120                 125

Leu Ala Lys Thr Leu Ala Ala Leu Thr Pro Gly Lys Leu Lys Tyr Ser
    130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
                245                 250                 255
```

```
Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
    370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430

Leu Thr Ile Glu Gln Cys Glu Leu Val Ile Lys Ala Ala Arg Lys Ala
        435                 440                 445

Leu Ala Ala Met Arg Val Ser Val Glu Glu Ala
    450                 455

<210> SEQ ID NO 13
<211> LENGTH: 453
<212> TYPE: PRT
<213> ORGANISM: Vibrio fluvialis

<400> SEQUENCE: 13

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175
```

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
            195                 200                 205

Ile Gln Arg Glu Gly Ala Asp Thr Ile Ala Gly Phe Phe Ala Glu Pro
210                 215                 220

Val Met Gly Ala Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
        370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
        450

<210> SEQ ID NO 14
<211> LENGTH: 224
<212> TYPE: PRT
<213> ORGANISM: Bacillus subtilis

<400> SEQUENCE: 14

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile

```
                    85                  90                  95
Cys Ala Phe Asp Ser Gln Pro Ile Gly Ile Asp Ile Glu Lys Thr Lys
                100                 105                 110

Pro Ile Ser Leu Glu Ile Ala Lys Arg Phe Phe Ser Lys Thr Glu Tyr
            115                 120                 125

Ser Asp Leu Leu Ala Lys Asp Lys Glu Gln Thr Asp Tyr Phe Tyr
130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
            195                 200                 205

Pro Asp Phe Pro Glu Asp Ile Thr Met Val Ser Tyr Glu Glu Leu Leu
210                 215                 220
```

<210> SEQ ID NO 15
<211> LENGTH: 222
<212> TYPE: PRT
<213> ORGANISM: Nocardia sp. NRRL 5646

<400> SEQUENCE: 15

```
Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu Glu His Leu Ile
            20                  25                  30

Ala Lys Ser Val Glu Lys Arg Arg Asp Phe Ile Gly Ala Arg His
            35                  40                  45

Cys Ala Arg Leu Ala Leu Ala Glu Leu Gly Glu Pro Pro Val Ala Ile
        50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Val Ala His Lys
                85                  90                  95

Met Arg Phe Arg Ser Ile Gly Ile Asp Ala Glu Pro His Ala Thr Leu
                100                 105                 110

Pro Glu Gly Val Leu Asp Ser Val Ser Leu Pro Pro Glu Arg Glu Trp
            115                 120                 125

Leu Lys Thr Thr Asp Ser Ala Leu His Leu Asp Arg Leu Leu Phe Cys
130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
            195                 200                 205

Leu Ile Ala Asp Gly Phe Ile Leu Thr Ala Ile Ala Tyr Ala
210                 215                 220
```

<210> SEQ ID NO 16
<211> LENGTH: 269

```
<212> TYPE: PRT
<213> ORGANISM: Bacillus cereus

<400> SEQUENCE: 16

Met Ile Asn Lys Thr Leu Leu Gln Lys Arg Phe Asn Val Ala Ala Val
1               5                   10                  15

Ser Tyr Asp Gln Tyr Ala Asn Val Gln Lys Lys Met Ala His Ser Leu
            20                  25                  30

Leu Ser Thr Leu Asn Arg Arg Tyr Ser Thr Asn Ser Ser Ile Arg Ile
        35                  40                  45

Leu Glu Leu Gly Cys Gly Thr Gly Tyr Val Thr Glu Gln Leu Ser Asn
    50                  55                  60

Leu Phe Pro Lys Ala Gln Ile Thr Ala Ile Asp Phe Ala Glu Ser Met
65                  70                  75                  80

Ile Ala Val Ala Lys Thr Arg Gln Asn Val Asn Asn Val Thr Phe Tyr
                85                  90                  95

Cys Glu Asp Ile Glu Arg Leu Arg Leu Glu Glu Thr Tyr Asp Val Ile
            100                 105                 110

Ile Ser Asn Ala Thr Phe Gln Trp Leu Asn Asp Leu Lys Gln Val Ile
        115                 120                 125

Thr Asn Leu Phe Arg His Leu Ser Ile Glu Gly Ile Leu Leu Phe Ser
    130                 135                 140

Thr Phe Gly Gln Glu Thr Phe Gln Glu Leu His Ala Ser Phe Gln Arg
145                 150                 155                 160

Ala Lys Glu Glu Lys Asn Ile Gln Asn Glu Thr Ser Ile Gly Gln Arg
                165                 170                 175

Phe Tyr Ser Lys Asn Gln Leu Arg His Ile Cys Glu Ile Glu Thr Gly
            180                 185                 190

Asp Val His Val Ser Glu Thr Cys Tyr Ile Glu Arg Phe Thr Glu Val
        195                 200                 205

Arg Glu Phe Leu His Ser Ile Arg Lys Val Gly Ala Thr Asn Ser Asn
    210                 215                 220

Glu Glu Ser Tyr Cys Gln Ser Pro Ser Leu Phe Arg Ala Met Leu Arg
225                 230                 235                 240

Ile Tyr Glu Arg Asp Phe Thr Gly Asn Glu Gly Ile Met Ala Thr Tyr
                245                 250                 255

His Ala Leu Phe Val His Ile Thr Lys Glu Gly Lys Arg
            260                 265

<210> SEQ ID NO 17
<211> LENGTH: 256
<212> TYPE: PRT
<213> ORGANISM: Escherichia coli

<400> SEQUENCE: 17

Met Asn Asn Ile Trp Trp Gln Thr Lys Gly Gln Gly Asn Val His Leu
1               5                   10                  15

Val Leu Leu His Gly Trp Gly Leu Asn Ala Glu Val Trp Arg Cys Ile
            20                  25                  30

Asp Glu Glu Leu Ser Ser His Phe Thr Leu His Leu Val Asp Leu Pro
        35                  40                  45

Gly Phe Gly Arg Ser Arg Gly Phe Gly Ala Leu Ser Leu Ala Asp Met
    50                  55                  60

Ala Glu Ala Val Leu Gln Gln Ala Pro Asp Lys Ala Ile Trp Leu Gly
65                  70                  75                  80
```

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
            100                 105                 110

Ala Arg Asp Glu Trp Pro Gly Ile Lys Pro Asp Val Leu Ala Gly Phe
        115                 120                 125

Gln Gln Gln Leu Ser Asp Asp Phe Gln Arg Thr Val Glu Arg Phe Leu
    130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
        195                 200                 205

Leu Val Pro Arg Lys Val Val Pro Met Leu Asp Lys Leu Trp Pro His
    210                 215                 220

Ser Glu Ser Tyr Ile Phe Ala Lys Ala Ala His Ala Pro Phe Ile Ser
225                 230                 235                 240

His Pro Ala Glu Phe Cys His Leu Leu Val Ala Leu Lys Gln Arg Val
                245                 250                 255

<210> SEQ ID NO 18
<211> LENGTH: 556
<212> TYPE: PRT
<213> ORGANISM: Clostridium cylindrosporum

<400> SEQUENCE: 18

Met Lys Thr Asp Val Gln Ile Ala Gln Glu Ala Gln Met Lys Pro Ile
1               5                   10                  15

Thr Glu Val Ala Asn Tyr Leu Gly Ile Gln Asp Asp Glu Leu Glu Leu
                20                  25                  30

Tyr Gly Lys Tyr Lys Ala Lys Val Ser Leu Asp Val Leu Glu Arg Gln
            35                  40                  45

Lys Asp Lys Glu Asp Ala Lys Leu Val Leu Val Thr Ala Ile Asn Pro
        50                  55                  60

Thr Pro Ala Gly Glu Gly Lys Thr Thr Thr Asn Val Gly Leu Ser Met
65                  70                  75                  80

Gly Leu Asn Lys Ile Gly Lys Arg Thr Ile Thr Ala Leu Arg Glu Pro
                85                  90                  95

Ser Leu Gly Pro Cys Phe Gly Val Lys Gly Ala Ala Gly Gly Gly
            100                 105                 110

Tyr Ala Gln Val Val Pro Met Asp Asp Ile Asn Leu His Phe Thr Gly
        115                 120                 125

Asp Phe His Ala Ile Thr Ser Ala His Asn Leu Leu Ala Ala Leu Leu
    130                 135                 140

Asp Asn His Leu His Gln Gly Asn Ala Leu Asn Ile Asn Pro Lys Lys
145                 150                 155                 160

Ile Val Trp Lys Arg Val Ile Asp Met Asn Asp Arg Ser Leu Arg Asn
                165                 170                 175

Val Ile Ile Gly Leu Gly Gly Asn Gly Asp Gly Phe Val Arg Gln Ala
            180                 185                 190

Gln Phe Asp Ile Thr Val Ala Ser Glu Ile Met Ala Ile Leu Cys Leu
        195                 200                 205

```
Ala Thr Ser Met Ser Asp Leu Lys Glu Arg Leu Ser Lys Met Ile Val
    210                 215                 220

Ala Tyr Ala Lys Asp Gly Ser Ala Val Thr Ala Gly Gln Leu Glu Ala
225                 230                 235                 240

Thr Gly Ala Met Ala Leu Leu Leu Lys Asp Ala Val Lys Pro Asn Leu
                245                 250                 255

Val Gln Thr Leu Glu Asn Thr Pro Ala Phe Ile His Gly Gly Pro Phe
            260                 265                 270

Ala Asn Ile Ala His Gly Cys Asn Ser Val Leu Ala Thr Lys Val Ala
        275                 280                 285

Leu Lys Leu Ala Asp Tyr Val Val Thr Glu Gly Gly Phe Gly Ala Asp
    290                 295                 300

Leu Gly Ala Glu Lys Phe Phe Asp Ile Lys Ser Arg Phe Ala Gly Leu
305                 310                 315                 320

Lys Pro Asn Cys Asp Val Ser Val Ala Thr Val Arg Ala Leu Lys Met
                325                 330                 335

Asn Gly Gly Val Pro Lys Thr Glu Leu Ala Ala Glu Asn Val Glu Ala
            340                 345                 350

Val Lys Lys Gly Val Ala Asn Leu Glu Arg His Ile Glu Asn Val Ala
    355                 360                 365

Lys Phe Gly Val Pro Ala Val Val Ala Ile Asn Lys Phe Pro Leu Asp
370                 375                 380

Thr Glu Ala Glu Leu Lys Ala Val Glu Asp Ala Cys Asn Ala Lys Gly
385                 390                 395                 400

Ala Asp Val Val Leu Ser Asp Val Trp Ala Asn Gly Gly Glu Gly Gly
                405                 410                 415

Val Glu Met Ala Lys Lys Val Val Glu Ile Cys Glu Lys Asn Glu Ala
            420                 425                 430

Asn Phe Ala Pro Leu Tyr Asp Val Asn Leu Ser Ile Pro Glu Lys Ile
        435                 440                 445

Glu Lys Ile Ala Thr Thr Ile Tyr Arg Ala Asp Gly Val Asp Phe Thr
    450                 455                 460

Ser Asp Cys Lys Lys Gln Ile Ala Glu Leu Glu Lys Leu Gly Leu Asp
465                 470                 475                 480

Lys Met Pro Ile Cys Met Ala Lys Thr Gln Tyr Ser Phe Ser Asp Asp
                485                 490                 495

Pro Thr Leu Leu Gly Ala Pro Thr Gly Phe Arg Ile Thr Val Arg Glu
            500                 505                 510

Val Arg Val Ser Ala Gly Ala Gly Phe Ile Val Ala Leu Thr Gly Asn
    515                 520                 525

Met Met Thr Met Pro Gly Leu Pro Lys Val Pro Ala Ala Asn Gly Met
530                 535                 540

Asp Ile Leu Glu Ser Gly Glu Ile Ile Gly Leu Ser
545                 550                 555

<210> SEQ ID NO 19
<211> LENGTH: 556
<212> TYPE: PRT
<213> ORGANISM: Alkaliphilus oremlandii (strain OhILAs)

<400> SEQUENCE: 19

Met Lys Thr Asp Val Gln Ile Ala Gln Glu Ala Lys Met Leu Pro Ile
1               5                   10                  15

Ala Asp Ile Ala Ala Gly Leu Gly Ile Gln Asp Asp Glu Leu Glu Leu
```

-continued

```
                 20                  25                  30
Tyr Gly Lys Tyr Lys Ala Lys Val Ser Leu Asp Val Phe Asp Arg Leu
             35                  40                  45
Lys Asp Lys Pro Asp Gly Lys Leu Ile Leu Val Thr Ala Ile Asn Pro
 50                  55                  60
Thr Pro Ala Gly Glu Gly Lys Thr Thr Thr Asn Val Gly Leu Ser Met
 65                  70                  75                  80
Gly Leu Asn Lys Ile Gly Lys Lys Thr Ile Thr Ala Leu Arg Glu Pro
                 85                  90                  95
Ser Leu Gly Pro Asn Phe Gly Val Lys Gly Ala Ala Gly Gly Gly
             100                 105                 110
Tyr Ala Gln Val Val Pro Met Glu Asp Ile Asn Leu His Phe Thr Gly
             115                 120                 125
Asp Ile His Ala Ile Thr Thr Ala His Asn Leu Leu Ala Ala Leu Leu
         130                 135                 140
Asp Asn His Leu His Gln Gly Asn Lys Leu Asn Ile Asp Ser Arg Arg
145                 150                 155                 160
Ile Val Trp Arg Arg Val Leu Asp Met Asn Asp Arg Ala Leu Arg Asn
                 165                 170                 175
Thr Val Ile Gly Leu Gly Ser Arg Gly Asp Gly Val Pro Arg Gln Asp
             180                 185                 190
Gly Phe Asp Ile Thr Val Ala Ser Glu Ile Met Ala Ile Leu Cys Leu
         195                 200                 205
Ser Asn Ser Leu Glu Asp Leu Lys Asp Arg Ile Ser Arg Met Val Val
     210                 215                 220
Ala Tyr Asn Leu Asp Asn Gln Pro Ile Thr Val Asn Asp Leu Glu Ala
225                 230                 235                 240
Thr Gly Ala Leu Ser Leu Leu Leu Lys Asp Ala Ile Lys Pro Asn Leu
             245                 250                 255
Val Gln Thr Leu Glu Asn Thr Pro Ala Phe Ile His Gly Gly Pro Phe
         260                 265                 270
Ala Asn Ile Ala His Gly Cys Asn Ser Val Leu Ala Thr Lys Leu Gly
     275                 280                 285
Leu Lys Leu Ala Asp Tyr Val Val Thr Glu Ala Gly Phe Gly Ala Asp
         290                 295                 300
Leu Gly Ala Glu Lys Phe Phe Asp Ile Lys Cys Arg Phe Ala Gly Leu
305                 310                 315                 320
Lys Pro Asp Cys Ala Val Ile Val Ala Thr Val Arg Ala Leu Lys Asn
             325                 330                 335
His Gly Gly Val Pro Lys Ala Glu Leu Asn Asn Glu Asn Leu Glu Ala
         340                 345                 350
Leu Glu Lys Gly Tyr Arg Asn Leu Glu Lys His Ile Glu Asn Val Gln
     355                 360                 365
Lys Phe Gly Val Pro Ala Val Val Ala Ile Asn Lys Phe Pro Thr Asp
         370                 375                 380
Thr Glu Ala Glu Leu Asn Phe Leu Arg Lys His Cys Ala Glu Met Gly
385                 390                 395                 400
Ala Glu Val Val Leu Ser Asp Val Trp Ala Asn Gly Gly Asp Gly Gly
             405                 410                 415
Ile Glu Met Ala Lys Lys Val Val Glu Val Val Glu Ser Lys Glu Ser
             420                 425                 430
Asn Phe Lys Pro Leu Tyr Asp Val Asn Ala Ser Ile Val Glu Lys Ile
             435                 440                 445
```

```
Asn Thr Ile Ala Lys Glu Val Tyr Gly Ala Asp Gly Val Asp Phe Thr
    450                 455                 460
Lys Ser Ala Gln Thr Gln Ile Lys Lys Tyr Glu Asp Leu Gly Leu Asp
465                 470                 475                 480
Lys Met Pro Ile Cys Met Ala Lys Thr Gln Tyr Ser Leu Ser Asp Asp
                485                 490                 495
Pro Ser Leu Ile Gly Arg Pro Ser Gly Phe Arg Ile Thr Val Lys Glu
            500                 505                 510
Ile Arg Leu Ser Ala Gly Ala Gly Phe Leu Val Ala Leu Thr Gly Asp
        515                 520                 525
Ile Met Val Met Pro Gly Leu Pro Lys Val Pro Ala Ala Asn His Met
    530                 535                 540
Asp Ile Leu Glu Ser Gly Glu Ile Ile Gly Leu Phe
545                 550                 555

<210> SEQ ID NO 20
<211> LENGTH: 556
<212> TYPE: PRT
<213> ORGANISM: Clostridium acidurici

<400> SEQUENCE: 20

Met Lys Thr Asp Ile Gln Ile Ala Gln Glu Ala Gln Met Lys His Ile
1               5                   10                  15
Lys Asp Val Ala Glu Leu Ile Asp Ile His Glu Asp Asp Leu Glu Leu
                20                  25                  30
Tyr Gly Lys Tyr Lys Ala Lys Val Ser Leu Asp Val Leu Asp Gln Leu
            35                  40                  45
Lys Asp Lys Pro Asp Gly Lys Leu Val Leu Val Thr Ala Ile Asn Pro
50                  55                  60
Thr Pro Ala Gly Glu Gly Lys Thr Thr Thr Asn Ile Gly Leu Ser Met
65                  70                  75                  80
Gly Leu Asn Lys Leu Gly Lys Lys Thr Ser Thr Ala Leu Arg Glu Pro
                85                  90                  95
Ser Leu Gly Pro Ser Phe Gly Val Lys Gly Gly Ala Ala Gly Gly Gly
            100                 105                 110
Tyr Ala Gln Val Val Pro Met Ala Asp Ile Asn Leu His Phe Thr Gly
        115                 120                 125
Asp Phe His Ala Ile Thr Ser Ala His Ser Leu Leu Ala Ala Leu Val
    130                 135                 140
Asp Asn His Leu His His Gly Asn Ala Leu Arg Ile Asp Thr Asn Arg
145                 150                 155                 160
Ile Val Trp Lys Arg Val Val Asp Met Asn Asp Arg Ala Leu Arg Lys
                165                 170                 175
Ile Val Val Gly Leu Gly Gly Lys Ala Gln Gly Ile Thr Arg Glu Asp
            180                 185                 190
Gly Phe Asp Ile Thr Val Ala Ser Glu Ile Met Ala Ile Leu Cys Leu
        195                 200                 205
Ala Asn Asp Arg Glu Asp Leu Lys Glu Arg Leu Gly Asn Met Val Val
    210                 215                 220
Ala Tyr Asn Val Asp Gly Asp Ala Val Arg Ala Lys Asp Leu Glu Ala
225                 230                 235                 240
Gln Gly Ala Leu Thr Leu Ile Leu Lys Asp Ala Ile Asn Pro Asn Ile
                245                 250                 255
Val Gln Thr Leu Glu Asn Thr Pro Ala Phe Ile His Gly Gly Pro Phe
```

```
                260                 265                 270
Ala Asn Ile Ala His Gly Cys Asn Ser Val Leu Ala Thr Lys Leu Ala
            275                 280                 285

Leu Lys Thr Gly Asp Tyr Ala Val Thr Glu Ala Gly Phe Gly Ala Asp
290                 295                 300

Leu Gly Ala Glu Lys Phe Phe Asp Ile Lys Cys Arg Tyr Ala Gly Leu
305                 310                 315                 320

Asn Pro Asp Val Ala Val Ile Val Ala Thr Val Arg Ala Leu Lys Met
            325                 330                 335

His Gly Gly Val Ala Lys Glu Asp Leu Gly Thr Glu Asn Leu Asp Ala
            340                 345                 350

Leu Ala Lys Gly Met Thr Asn Leu Glu Arg His Ile Glu Asn Val Ala
            355                 360                 365

Lys Phe Gly Val Pro Ser Val Val Ala Ile Asn Ala Phe Pro Thr Asp
            370                 375                 380

Thr Glu Ala Glu Lys Gln Leu Val Phe Asp Lys Cys Lys Glu Met Gly
385                 390                 395                 400

Val Asp Val Ala Ile Ser Asp Val Phe Ala Lys Gly Gly Asp Gly Gly
            405                 410                 415

Val Glu Leu Ala Gln Lys Val Ile Asp Val Cys Glu Asn Lys Lys Ser
            420                 425                 430

Asp Phe Lys Val Leu Tyr Asp Val Glu Glu Ser Ile Pro Glu Lys Ile
            435                 440                 445

Thr Lys Ile Ala Lys Glu Ile Tyr Arg Ala Asp Lys Val Asn Phe Ser
450                 455                 460

Lys Ala Ala Lys Lys Gln Ile Ala Glu Leu Glu Lys Leu Gly Leu Asp
465                 470                 475                 480

Lys Leu Pro Ile Cys Met Ala Lys Thr Gln Tyr Ser Phe Ser Asp Asp
            485                 490                 495

Pro Ala Leu Leu Gly Ala Pro Glu Gly Phe Glu Leu Thr Ile Arg Asp
            500                 505                 510

Leu Glu Leu Ala Ala Gly Ala Gly Phe Ile Val Ala Leu Thr Gly Asp
            515                 520                 525

Ile Met Arg Met Pro Gly Leu Pro Lys Val Pro Ala Ala Asn Arg Met
            530                 535                 540

Asp Val Leu Pro Asn Gly Glu Ile Ile Gly Leu Phe
545                 550                 555

<210> SEQ ID NO 21
<211> LENGTH: 556
<212> TYPE: PRT
<213> ORGANISM: Eubacterium acidaminophilum

<400> SEQUENCE: 21

Met Lys Thr Asp Val Gln Ile Ala Gln Glu Ala Lys Met Leu Pro Ile
1               5                   10                  15

Met Glu Val Ala Lys Gln Ile Gly Leu Gly Glu Asp Ile Glu Leu
            20                  25                  30

Tyr Gly Lys Tyr Lys Ala Lys Ile Ser Leu Asp Val Tyr Lys Arg Leu
            35                  40                  45

Ala Asp Lys Pro Asp Gly Lys Leu Val Leu Val Thr Ala Ile Asn Pro
            50                  55                  60

Thr Pro Ala Gly Glu Gly Lys Thr Thr Thr Asn Val Gly Leu Ser Met
65                  70                  75                  80
```

```
Gly Leu Asn Lys Ile Gly Lys Lys Thr Ile Thr Ala Leu Asn Glu Pro
                85                  90                  95

Ser Leu Gly Pro Cys Phe Gly Val Lys Gly Ala Ala Gly Gly Gly
            100                 105                 110

Tyr Ala Gln Val Val Pro Met Asp Asp Ile Asn Leu His Phe Thr Gly
            115                 120                 125

Asp Ile His Ala Ile Thr Thr Ala His Asn Leu Leu Ala Ala Leu Met
            130                 135                 140

Asp Asn His Ile Lys Gln Gly Asn Ala Leu Gly Ile Asp Ile Asn Lys
145                 150                 155                 160

Ile Thr Trp Lys Arg Val Leu Asp Met Asn Asp Arg Ala Leu Arg Asp
                165                 170                 175

Ile Val Ile Gly Leu Gly Gly Thr Ala Asn Gly Ile Pro Arg Gln Asp
            180                 185                 190

Gly Phe Asp Ile Thr Val Ala Ser Glu Ile Met Ala Ile Met Cys Leu
            195                 200                 205

Ala Thr Ser Leu Ser Asp Leu Lys Asp Arg Leu Ser Arg Met Ile Val
            210                 215                 220

Gly Tyr Thr Ser Arg Arg Leu Ala Val Thr Ala Asp Ser Leu Thr Leu
225                 230                 235                 240

Arg Gly Ala Leu Ala Leu Leu Lys Asp Ala Leu Lys Pro Asn Leu
                245                 250                 255

Val Gln Thr Leu Glu Asn Thr Pro Ala Ile Ile His Gly Gly Pro Phe
            260                 265                 270

Ala Asn Ile Ala His Gly Cys Asn Ser Val Thr Thr Thr Lys Thr Ala
            275                 280                 285

Leu Lys Ile Ala Asp Tyr Val Val Thr Glu Ala Gly Phe Gly Ala Asp
    290                 295                 300

Leu Gly Ala Glu Lys Phe Phe Asp Ile Lys Cys Arg Phe Ala Asp Leu
305                 310                 315                 320

Lys Pro Asp Val Ala Val Ile Val Ala Thr Val Arg Ala Leu Lys Asn
                325                 330                 335

His Gly Gly Val Ala Lys Ala Asn Leu Gly Ala Glu Asn Met Lys Ala
            340                 345                 350

Leu Glu Asp Gly Phe Gly Asn Leu Glu Arg His Ile Glu Asn Val His
            355                 360                 365

Lys Phe Gly Val Pro Ala Val Val Ala Ile Asn Ala Phe Pro Thr Asp
            370                 375                 380

Thr Glu Lys Glu Leu Lys Phe Val Glu Asp Ala Cys Arg Lys Leu Gly
385                 390                 395                 400

Ala Asp Val Val Leu Ser Glu Val Trp Ala Lys Gly Gly Glu Gly Gly
                405                 410                 415

Val Glu Leu Ala Lys Lys Val Val Glu Val Thr Glu Lys Gly Ala Ala
            420                 425                 430

Lys Phe Lys Pro Leu Tyr Pro Ala Glu Met Pro Leu Lys Gln Lys Ile
            435                 440                 445

Glu Thr Ile Ala Lys Glu Ile Tyr Arg Ala Asp Gly Val Glu Phe Ser
            450                 455                 460

Ala Lys Ala Ser Lys Glu Leu Asp Lys Phe Glu Lys Leu Gly Phe Gly
465                 470                 475                 480

Asn Leu Pro Ile Cys Val Ala Lys Thr Gln Tyr Ser Phe Ser Asp Asn
                485                 490                 495

Pro Asn Leu Lys Gly Ala Pro Lys Gly Phe Thr Val Ser Val Ser Asn
```

```
            500             505             510
Ala Arg Ile Ser Ala Gly Ala Gly Phe Ile Val Val Leu Thr Gly Asp
        515                 520                 525
Ile Met Thr Met Pro Gly Leu Pro Lys Val Pro Ala Ala Asn His Met
        530                 535                 540
Asp Val Leu Glu Ser Gly Glu Ile Val Gly Leu Phe
545                 550                 555

<210> SEQ ID NO 22
<211> LENGTH: 556
<212> TYPE: PRT
<213> ORGANISM: Desulfitobacterium hafniense (strain Y51)

<400> SEQUENCE: 22

Met Lys Thr Asp Ile Glu Ile Ala Gln Glu Ala Thr Met Lys Pro Ile
1               5                   10                  15
Thr Glu Ile Ala Gln Gly Leu Asp Leu Leu Glu Asp Glu Ile Glu Leu
                20                  25                  30
Tyr Gly Lys Tyr Lys Ala Lys Val Asn Phe Ser Ala Trp Glu Arg Leu
            35                  40                  45
Lys Asp Lys Pro Asp Ala Lys Leu Ile Leu Val Thr Ala Ile Asn Pro
50                  55                  60
Thr Pro Ala Gly Glu Gly Lys Thr Thr Thr Thr Val Gly Leu Gly Gln
65                  70                  75                  80
Ala Met Ser Lys Ile Gly Lys Asn Ala Met Ile Ala Leu Arg Glu Pro
                85                  90                  95
Ser Leu Gly Pro Cys Phe Gly Val Lys Gly Gly Ala Ala Gly Gly Gly
                100                 105                 110
Tyr Ala Gln Val Val Pro Met Glu Asp Ile Asn Leu His Phe Thr Gly
            115                 120                 125
Asp Phe His Ala Ile Thr Ser Thr His Asn Leu Leu Ala Ala Leu Leu
130                 135                 140
Asp Asn His Ile Gln Gln Gly Asn Leu Leu Asn Ile Asp Pro Arg Gln
145                 150                 155                 160
Ile Val Phe Arg Arg Val Met Asp Met Asn Asp Arg Ala Leu Arg Lys
                165                 170                 175
Ile Val Ile Gly Leu Gly Gly Arg Thr Glu Gly Ile Pro Arg Glu Asn
            180                 185                 190
Gly Phe Asp Ile Thr Val Ala Ser Glu Ile Met Ala Ile Leu Cys Leu
            195                 200                 205
Ala Lys Asp Leu Met Asp Leu Lys Glu Arg Phe Gly Arg Ile Val Val
210                 215                 220
Ala Tyr Thr Tyr Asp Gly Lys Ala Ile Thr Ala His Asp Leu Glu Ala
225                 230                 235                 240
Glu Gly Ala Met Ala Leu Leu Met Lys Asp Ala Ile Lys Pro Asn Leu
                245                 250                 255
Val Gln Thr Leu Glu Asn Thr Pro Val Phe Ile His Gly Gly Pro Phe
                260                 265                 270
Ala Asn Ile Ala His Gly Cys Asn Ser Val Val Ala Thr Arg Met Ala
            275                 280                 285
Met Lys Leu Ala Asp Tyr Val Ile Thr Glu Ala Gly Phe Gly Ala Asp
        290                 295                 300
Leu Gly Ala Glu Lys Phe Tyr Asp Leu Lys Cys Arg Phe Ala Glu Leu
305                 310                 315                 320
```

Lys Pro Ala Ala Thr Val Ile Val Ala Thr Val Arg Ala Leu Lys Met
                325                 330                 335

Asn Gly Gly Val Ala Lys Glu Asp Leu Gly Pro Glu Asn Leu Glu Ala
            340                 345                 350

Leu Ala Lys Gly Ile Val Asn Leu Glu Lys His Ile Glu Asn Ile Gly
        355                 360                 365

Lys Phe Gly Val Pro Ala Val Ala Ile Asn Arg Phe Pro Thr Asp
    370                 375                 380

Thr Asp Ala Glu Leu Glu Phe Val Ala Glu Cys Arg Gln Leu Gly
385                 390                 395                 400

Ala Glu Phe Ala Leu Ser Glu Val Phe Thr Lys Gly Glu Gly Gly
                405                 410                 415

Ile Glu Leu Ala Lys Ala Val Leu Asn Ile Val Asp Asn Lys Glu Ser
                420                 425                 430

Asn Phe His Val Leu Tyr Glu Leu Asp Leu Pro Ile Ala Lys Lys Ile
            435                 440                 445

Glu Thr Ile Cys Lys Glu Val Tyr Gly Ala Asp Gly Val Asn Phe Thr
        450                 455                 460

Lys Glu Ala Leu Thr Ser Met Lys Lys Tyr Glu Glu Leu Gly Tyr Gly
465                 470                 475                 480

Gln Leu Pro Ile Cys Met Ala Lys Thr Gln Tyr Ser Leu Thr Asp Asp
                485                 490                 495

Gln Asn Val Leu Gly Arg Pro Ser Gly Phe Thr Ile Thr Val Arg Glu
                500                 505                 510

Leu Arg Leu Ser Ala Gly Ala Gly Phe Leu Val Ala Ile Thr Gly Ala
            515                 520                 525

Ile Met Thr Met Pro Gly Leu Pro Lys Arg Pro Ala Ala Leu Arg Met
        530                 535                 540

Asp Ile Asp Ala Ala Gly Arg Ile Thr Gly Leu Phe
545                 550                 555

<210> SEQ ID NO 23
<211> LENGTH: 369
<212> TYPE: PRT
<213> ORGANISM: Escherichia coli (strain K12)

<400> SEQUENCE: 23

Met Lys Ser Arg Ala Ala Val Ala Phe Ala Pro Gly Lys Pro Leu Glu
1               5                   10                  15

Ile Val Glu Ile Asp Val Ala Pro Pro Lys Lys Gly Glu Val Leu Ile
            20                  25                  30

Lys Val Thr His Thr Gly Val Cys His Thr Asp Ala Phe Thr Leu Ser
        35                  40                  45

Gly Asp Asp Pro Glu Gly Val Phe Pro Val Val Leu Gly His Glu Gly
    50                  55                  60

Ala Gly Val Val Glu Val Gly Glu Gly Val Thr Ser Val Lys Pro
65                  70                  75                  80

Gly Asp His Val Ile Pro Leu Tyr Thr Ala Glu Cys Gly Glu Cys Glu
                85                  90                  95

Phe Cys Arg Ser Gly Lys Thr Asn Leu Cys Val Ala Val Arg Glu Thr
            100                 105                 110

Gln Gly Lys Gly Leu Met Pro Asp Gly Thr Thr Arg Phe Ser Tyr Asn
        115                 120                 125

Gly Gln Pro Leu Tyr His Tyr Met Gly Cys Ser Thr Phe Ser Glu Tyr
    130                 135                 140

```
Thr Val Val Ala Glu Val Ser Leu Ala Lys Ile Asn Pro Glu Ala Asn
145                 150                 155                 160

His Glu His Val Cys Leu Leu Gly Cys Gly Val Thr Thr Gly Ile Gly
            165                 170                 175

Ala Val His Asn Thr Ala Lys Val Gln Pro Gly Asp Ser Val Ala Val
        180                 185                 190

Phe Gly Leu Gly Ala Ile Gly Leu Ala Val Val Gln Gly Ala Arg Gln
    195                 200                 205

Ala Lys Ala Gly Arg Ile Ile Ala Ile Asp Thr Asn Pro Lys Lys Phe
210                 215                 220

Asp Leu Ala Arg Arg Phe Gly Ala Thr Asp Cys Ile Asn Pro Asn Asp
225                 230                 235                 240

Tyr Asp Lys Pro Ile Lys Asp Val Leu Leu Asp Ile Asn Lys Trp Gly
                245                 250                 255

Ile Asp His Thr Phe Glu Cys Ile Gly Asn Val Asn Val Met Arg Ala
            260                 265                 270

Ala Leu Glu Ser Ala His Arg Gly Trp Gly Gln Ser Val Ile Ile Gly
        275                 280                 285

Val Ala Val Ala Gly Gln Glu Ile Ser Thr Arg Pro Phe Gln Leu Val
290                 295                 300

Thr Gly Arg Val Trp Lys Gly Ser Ala Phe Gly Gly Val Lys Gly Arg
305                 310                 315                 320

Ser Gln Leu Pro Gly Met Val Glu Asp Ala Met Lys Gly Asp Ile Asp
                325                 330                 335

Leu Glu Pro Phe Val Thr His Thr Met Ser Leu Asp Glu Ile Asn Asp
            340                 345                 350

Ala Phe Asp Leu Met His Glu Gly Lys Ser Ile Arg Thr Val Ile Arg
        355                 360                 365

Tyr

<210> SEQ ID NO 24
<211> LENGTH: 369
<212> TYPE: PRT
<213> ORGANISM: Shigella sonnei (strain Ss046)

<400> SEQUENCE: 24

Met Lys Ser Arg Ala Ala Val Ala Phe Ala Pro Gly Lys Pro Leu Glu
1               5                   10                  15

Ile Val Glu Ile Asp Val Ala Pro Pro Lys Lys Gly Glu Val Leu Ile
            20                  25                  30

Lys Val Thr His Thr Gly Val Cys His Thr Asp Ala Phe Thr Leu Ser
        35                  40                  45

Gly Asp Asp Pro Glu Gly Val Phe Pro Val Val Leu Gly His Glu Gly
    50                  55                  60

Ala Gly Val Val Glu Val Gly Glu Gly Val Thr Ser Val Lys Pro
65                  70                  75                  80

Gly Asp His Val Ile Pro Leu Tyr Thr Ala Glu Cys Gly Glu Cys Glu
                85                  90                  95

Phe Cys Arg Ser Gly Lys Thr Asn Leu Cys Val Ala Val Arg Glu Thr
            100                 105                 110

Gln Gly Lys Gly Leu Met Pro Asp Gly Thr Thr Arg Phe Ser Tyr Asn
        115                 120                 125

Gly Gln Pro Leu Tyr His Tyr Met Gly Cys Ser Thr Phe Ser Glu Tyr
    130                 135                 140
```

Thr Val Val Ala Glu Val Ser Leu Ala Lys Ile Asn Pro Glu Ala Asn
145                 150                 155                 160

His Glu His Val Cys Leu Leu Gly Cys Gly Val Thr Thr Gly Ile Gly
            165                 170                 175

Ala Val His Asn Thr Ala Lys Val Gln Pro Gly Asp Ser Val Ala Val
        180                 185                 190

Phe Gly Leu Gly Ala Ile Gly Leu Ala Val Val Gln Gly Ala Arg Gln
    195                 200                 205

Ala Lys Ala Gly Arg Ile Ile Ala Ile Asp Thr Asn Pro Lys Lys Phe
210                 215                 220

Asp Leu Ala Arg Arg Phe Gly Ala Thr Asp Cys Ile Asn Pro Asn Asp
225                 230                 235                 240

Tyr Asp Lys Pro Ile Lys Asp Val Leu Leu Asp Ile Asn Lys Trp Gly
                245                 250                 255

Ile Asp His Thr Phe Glu Cys Ile Gly Asn Val Asn Val Met Arg Ala
            260                 265                 270

Ala Leu Glu Ser Ala His Arg Gly Trp Gly Gln Ser Val Ile Ile Gly
        275                 280                 285

Val Ala Gly Ser Gly Gln Glu Ile Ser Thr Arg Pro Phe Gln Leu Val
    290                 295                 300

Thr Gly Arg Val Trp Lys Gly Ser Ala Phe Gly Gly Val Lys Gly Arg
305                 310                 315                 320

Ser Gln Leu Pro Gly Met Val Glu Asp Ala Met Lys Gly Asp Ile Asp
                325                 330                 335

Leu Glu Pro Phe Val Thr His Thr Met Ser Leu Asp Glu Ile Asn Asp
            340                 345                 350

Ala Phe Asp Leu Met His Glu Gly Lys Ser Ile Arg Thr Val Ile Arg
        355                 360                 365

Tyr

<210> SEQ ID NO 25
<211> LENGTH: 369
<212> TYPE: PRT
<213> ORGANISM: Achromobacter sp.

<400> SEQUENCE: 25

Met Lys Ser Arg Ala Ala Val Ala Phe Ala Pro Gly Lys Pro Leu Glu
1               5                   10                  15

Ile Val Glu Ile Asp Val Ala Pro Pro Lys Lys Gly Glu Val Leu Ile
            20                  25                  30

Lys Val Thr His Thr Gly Val Cys His Thr Asp Ala Phe Thr Leu Ser
        35                  40                  45

Gly Asp Asp Pro Glu Gly Val Phe Pro Val Val Leu Gly His Glu Gly
    50                  55                  60

Ala Gly Val Val Glu Val Gly Glu Gly Val Thr Ser Val Lys Pro
65                  70                  75                  80

Gly Asp His Val Ile Pro Leu Tyr Thr Ala Glu Cys Gly Glu Cys Glu
                85                  90                  95

Phe Cys Arg Ser Gly Lys Thr Asn Leu Cys Val Ala Val Arg Glu Thr
            100                 105                 110

Gln Gly Lys Gly Leu Met Pro Asp Gly Thr Thr Arg Phe Ser Tyr Asn
        115                 120                 125

Gly Gln Pro Leu Tyr His Tyr Met Gly Cys Ser Thr Phe Ser Glu Tyr
    130                 135                 140

```
Thr Val Val Ala Glu Val Ser Leu Ala Lys Ile Asn Pro Glu Ala Asn
145                 150                 155                 160

His Glu His Val Cys Leu Leu Gly Cys Gly Val Thr Thr Gly Ile Gly
                165                 170                 175

Ala Val His Asn Thr Ala Lys Val Gln Pro Gly Asp Ser Val Ala Val
            180                 185                 190

Phe Gly Leu Gly Ala Ile Gly Leu Ala Val Val Gln Gly Ala Arg Gln
        195                 200                 205

Ala Lys Ala Gly Arg Ile Ile Ala Ile Asp Thr Asn Pro Lys Lys Phe
210                 215                 220

Asp Leu Ala Arg Arg Phe Gly Ala Thr Asp Cys Ile Asn Pro Asn Asp
225                 230                 235                 240

Tyr Asp Lys Pro Ile Lys Asp Val Leu Leu Asp Ile Asn Lys Trp Gly
                245                 250                 255

Ile Asp His Thr Phe Glu Cys Ile Gly Asn Val Asn Val Met Arg Ala
            260                 265                 270

Ala Leu Glu Ser Ala His Arg Gly Trp Gly Gln Ser Val Ile Ile Gly
        275                 280                 285

Val Ala Gly Ala Gly Gln Glu Ile Ser Thr Arg Pro Phe Gln Leu Val
290                 295                 300

Thr Gly Arg Val Trp Lys Gly Ser Ala Phe Gly Val Lys Gly Arg
305                 310                 315                 320

Ser Gln Leu Pro Gly Met Val Glu Asp Ala Met Lys Gly Asp Ile Asp
                325                 330                 335

Leu Glu Pro Phe Val Thr His Thr Met Ser Leu Asp Glu Ile Asn Asp
            340                 345                 350

Ala Phe Asp Leu Met His Glu Gly Lys Ser Ile Arg Thr Val Ile Arg
        355                 360                 365

Tyr

<210> SEQ ID NO 26
<211> LENGTH: 369
<212> TYPE: PRT
<213> ORGANISM: Klebsiella pneumoniae IS22

<400> SEQUENCE: 26

Met Lys Ser Arg Ala Ala Val Ala Phe Ala Pro Gly Lys Pro Leu Glu
1               5                   10                  15

Ile Val Glu Ile Asp Val Ala Pro Pro Lys Lys Gly Glu Val Leu Ile
            20                  25                  30

Lys Val Thr His Thr Gly Val Cys His Thr Asp Ala Phe Thr Leu Ser
        35                  40                  45

Gly Asp Asp Pro Glu Gly Val Phe Pro Val Val Leu Gly His Glu Gly
    50                  55                  60

Ala Gly Val Val Glu Val Gly Glu Gly Val Thr Ser Val Lys Pro
65                  70                  75                  80

Gly Asp His Val Ile Pro Leu Tyr Thr Ala Glu Cys Gly Glu Cys Glu
                85                  90                  95

Phe Cys Arg Ser Gly Lys Thr Asn Leu Cys Val Ala Val Arg Glu Thr
            100                 105                 110

Gln Gly Lys Gly Leu Met Pro Asp Gly Thr Thr Arg Phe Ser Tyr Asn
        115                 120                 125

Gly Gln Pro Leu Tyr His Tyr Met Gly Cys Ser Thr Phe Ser Glu Tyr
    130                 135                 140
```

Thr Val Val Ala Glu Val Ser Leu Ala Lys Ile Asn Pro Glu Ala Asn
145                 150                 155                 160

His Glu His Val Cys Leu Leu Gly Cys Gly Val Thr Thr Gly Ile Gly
                165                 170                 175

Ala Val His Asn Thr Ala Lys Val Gln Pro Gly Asp Ser Val Ala Val
            180                 185                 190

Phe Gly Leu Gly Ala Ile Gly Leu Ala Val Val Gln Gly Ala Arg Gln
            195                 200                 205

Ala Lys Ala Gly Arg Ile Ile Ala Ile Asp Thr Asn Pro Lys Lys Phe
210                 215                 220

Asp Leu Ala Arg Arg Phe Gly Ala Thr Asp Cys Ile Asn Pro Asn Asp
225                 230                 235                 240

Tyr Asp Lys Pro Ile Lys Asp Val Leu Leu Asp Ile Asn Lys Trp Gly
            245                 250                 255

Ile Asp His Thr Phe Glu Cys Ile Gly Asn Val Asn Val Met Arg Ala
            260                 265                 270

Ala Leu Glu Ser Ala His Arg Gly Trp Gly Gln Ser Val Ile Ile Gly
            275                 280                 285

Val Ala Gly Ala Gly Gln Glu Ile Ser Thr Arg Pro Phe Gln Leu Val
290                 295                 300

Thr Gly Arg Val Trp Lys Gly Ser Ala Phe Gly Gly Val Lys Gly Arg
305                 310                 315                 320

Ser Gln Leu Pro Gly Met Val Glu Asp Ala Met Lys Gly Asp Ile Asp
            325                 330                 335

Leu Glu Pro Phe Val Thr His Thr Met Ser Leu Asp Glu Ile Asn Asp
            340                 345                 350

Ala Phe Asp Leu Met His Glu Gly Lys Ser Ile Arg Thr Val Ile Arg
            355                 360                 365

Tyr

<210> SEQ ID NO 27
<211> LENGTH: 277
<212> TYPE: PRT
<213> ORGANISM: Escherichia coli (strain K12)

<400> SEQUENCE: 27

Met Glu Leu Ile Glu Lys His Val Ser Phe Gly Gly Trp Gln Asn Met
1               5                   10                  15

Tyr Arg His Tyr Ser Gln Ser Leu Lys Cys Glu Met Asn Val Gly Val
            20                  25                  30

Tyr Leu Pro Pro Lys Ala Ala Asn Glu Lys Leu Pro Val Leu Tyr Trp
        35                  40                  45

Leu Ser Gly Leu Thr Cys Asn Glu Gln Asn Phe Ile Thr Lys Ser Gly
    50                  55                  60

Met Gln Arg Tyr Ala Ala Glu His Asn Ile Ile Val Val Ala Pro Asp
65                  70                  75                  80

Thr Ser Pro Arg Gly Ser His Val Ala Asp Ala Asp Arg Tyr Asp Leu
                85                  90                  95

Gly Gln Gly Ala Gly Phe Tyr Leu Asn Ala Thr Gln Ala Pro Trp Asn
            100                 105                 110

Glu His Tyr Lys Met Tyr Asp Tyr Ile Arg Asn Glu Leu Pro Asp Leu
        115                 120                 125

Val Met His His Phe Pro Ala Thr Ala Lys Lys Ser Ile Ser Gly His
    130                 135                 140

```
Ser Met Gly Gly Leu Gly Ala Leu Val Leu Ala Leu Arg Asn Pro Asp
145                 150                 155                 160

Glu Tyr Val Ser Val Ser Ala Phe Ser Pro Ile Val Ser Pro Ser Gln
                165                 170                 175

Val Pro Trp Gly Gln Gln Ala Phe Ala Ala Tyr Leu Ala Glu Asn Lys
            180                 185                 190

Asp Ala Trp Leu Asp Tyr Asp Pro Val Ser Leu Ile Ser Gln Gly Gln
            195                 200                 205

Arg Val Ala Glu Ile Met Val Asp Gln Gly Leu Ser Asp Asp Phe Tyr
        210                 215                 220

Ala Glu Gln Leu Arg Thr Pro Asn Leu Glu Lys Ile Cys Gln Glu Met
225                 230                 235                 240

Asn Ile Lys Thr Leu Ile Arg Tyr His Glu Gly Tyr Asp His Ser Tyr
                245                 250                 255

Tyr Phe Val Ser Ser Phe Ile Gly Glu His Ile Ala Tyr His Ala Asn
                260                 265                 270

Lys Leu Asn Met Arg
            275

<210> SEQ ID NO 28
<211> LENGTH: 277
<212> TYPE: PRT
<213> ORGANISM: Shigella sonnei (strain Ss046)

<400> SEQUENCE: 28

Met Glu Leu Ile Glu Lys His Ala Ser Phe Gly Gly Trp Gln Asn Val
1               5                   10                  15

Tyr Arg His Tyr Ser Gln Ser Leu Lys Cys Glu Met Asn Val Gly Val
                20                  25                  30

Tyr Leu Pro Pro Lys Ala Ala Asn Glu Lys Leu Pro Val Leu Tyr Trp
            35                  40                  45

Leu Ser Gly Leu Thr Cys Asn Glu Gln Asn Phe Ile Thr Lys Ser Gly
        50                  55                  60

Met Gln Arg Tyr Ala Ala Glu His Asn Ile Ile Val Val Ala Pro Asp
65                  70                  75                  80

Thr Ser Pro Arg Gly Ser His Val Ala Asp Ala Asp Arg Tyr Asp Leu
                85                  90                  95

Gly Gln Gly Ala Gly Phe Tyr Leu Asn Ala Thr Gln Ala Pro Trp Asn
            100                 105                 110

Glu His Tyr Lys Met Tyr Asp Tyr Ile Arg Asn Glu Leu Pro Asp Leu
        115                 120                 125

Val Met Gln His Phe Pro Ala Thr Thr Arg Lys Ser Ile Ser Gly His
    130                 135                 140

Ser Met Gly Gly Leu Gly Ala Leu Val Leu Ala Leu Arg Asn Pro Asp
145                 150                 155                 160

Glu Tyr Val Ser Val Ser Ala Phe Ser Pro Ile Val Ser Pro Ser Gln
                165                 170                 175

Val Pro Trp Gly Gln Gln Ala Phe Ala Ala Tyr Leu Gly Glu Asn Lys
            180                 185                 190

Asp Ala Trp Leu Asp Tyr Asp Pro Val Ser Leu Ile Ser Gln Gly Gln
            195                 200                 205

Arg Val Ala Glu Ile Met Val Asp Gln Gly Leu Ser Asp Asp Phe Tyr
        210                 215                 220

Ala Glu Gln Leu Arg Thr Pro Asn Leu Glu Lys Ile Cys Gln Glu Met
```

```
                    225                 230                 235                 240

Asn Ile Lys Thr Leu Ile Arg Tyr His Glu Gly Tyr Asp His Ser Tyr
                245                 250                 255

Tyr Phe Val Ser Ser Phe Ile Gly Glu His Ile Ala Tyr His Ala Asn
                260                 265                 270

Lys Leu Asn Met Arg
            275

<210> SEQ ID NO 29
<211> LENGTH: 277
<212> TYPE: PRT
<213> ORGANISM: Achromobacter sp.

<400> SEQUENCE: 29

Met Glu Leu Ile Glu Lys His Val Ser Phe Gly Gly Trp Gln Asn Val
1               5                   10                  15

Tyr Arg His Tyr Ser Gln Ser Leu Lys Cys Glu Met Asn Val Gly Val
                20                  25                  30

Tyr Leu Pro Pro Lys Ala Ala Asn Glu Lys Leu Pro Val Leu Tyr Trp
            35                  40                  45

Leu Ser Gly Leu Thr Cys Asn Glu Gln Asn Phe Ile Thr Lys Ser Gly
        50                  55                  60

Met Gln Arg Tyr Ala Ala Glu His Asn Ile Ile Val Val Ala Pro Asp
65                  70                  75                  80

Thr Ser Pro Arg Gly Ser His Val Ala Asp Ala Asp Arg Tyr Asp Leu
                85                  90                  95

Gly Gln Gly Ala Gly Phe Tyr Leu Asn Ala Thr Gln Ala Pro Trp Asn
            100                 105                 110

Glu His Tyr Lys Met Tyr Asp Tyr Ile Arg Asn Glu Leu Pro Asp Leu
        115                 120                 125

Val Met His His Phe Pro Ala Thr Ala Lys Lys Ser Ile Ser Gly His
    130                 135                 140

Ser Met Gly Gly Leu Gly Ala Leu Val Leu Ala Leu Arg Asn Pro Asp
145                 150                 155                 160

Glu Tyr Val Ser Val Ser Ala Phe Ser Pro Ile Val Ser Pro Ser Gln
                165                 170                 175

Val Pro Trp Gly Gln Gln Ala Phe Ala Ala Tyr Leu Ala Glu Asn Lys
            180                 185                 190

Asp Ala Trp Leu Asp Tyr Asp Pro Val Ser Leu Ile Ser Gln Gly Gln
        195                 200                 205

Arg Val Ala Glu Ile Met Val Asp Gln Gly Leu Ser Asp Asp Phe Tyr
    210                 215                 220

Ala Glu Gln Leu Arg Thr Pro Asn Leu Glu Lys Ile Cys Gln Glu Met
225                 230                 235                 240

Asn Ile Lys Thr Leu Ile Arg Tyr His Glu Gly Tyr Asp His Ser Tyr
                245                 250                 255

Tyr Phe Val Ser Ser Phe Ile Gly Glu His Ile Ala Tyr His Ala Asn
                260                 265                 270

Lys Leu Asn Met Arg
            275

<210> SEQ ID NO 30
<211> LENGTH: 277
<212> TYPE: PRT
<213> ORGANISM: Klebsiella pneumoniae IS22
```

-continued

<400> SEQUENCE: 30

Met Glu Leu Ile Glu Lys His Ala Ser Phe Gly Gly Trp Gln Asn Val
1               5                   10                  15

Tyr Arg His Tyr Ser Gln Ser Leu Lys Cys Glu Met Asn Val Gly Val
            20                  25                  30

Tyr Leu Pro Pro Lys Ala Ala Asn Glu Lys Leu Pro Val Leu Tyr Trp
        35                  40                  45

Leu Ser Gly Leu Thr Cys Asn Glu Gln Asn Phe Ile Thr Lys Ser Gly
    50                  55                  60

Met Gln Arg Tyr Ala Ala Glu His Asn Ile Ile Val Val Ala Pro Asp
65                  70                  75                  80

Thr Ser Pro Arg Gly Ser His Val Ala Asp Ala Asp Arg Tyr Asp Leu
                85                  90                  95

Gly Gln Gly Ala Gly Phe Tyr Leu Asn Ala Thr Gln Ala Pro Trp Asn
            100                 105                 110

Glu His Tyr Lys Met Tyr Asp Tyr Ile Arg Asn Glu Leu Pro Asp Leu
        115                 120                 125

Val Met His His Phe Pro Ala Thr Ala Lys Lys Ser Ile Ser Gly His
    130                 135                 140

Ser Met Gly Gly Leu Gly Ala Leu Val Leu Ala Leu Arg Asn Pro Asp
145                 150                 155                 160

Glu Tyr Val Ser Val Ser Ala Phe Ser Pro Ile Val Ser Pro Ser Gln
                165                 170                 175

Val Pro Trp Gly Gln Gln Ala Phe Ala Ala Tyr Leu Ala Glu Asn Lys
            180                 185                 190

Asp Ala Trp Leu Asp Tyr Asp Pro Val Ser Leu Ile Ser Gln Gly Gln
        195                 200                 205

Arg Val Ala Glu Ile Met Val Asp Gln Gly Leu Ser Asp Asp Phe Tyr
    210                 215                 220

Ala Glu Gln Leu Arg Thr Pro Asn Leu Glu Lys Ile Cys Gln Glu Met
225                 230                 235                 240

Asn Ile Lys Thr Leu Ile Arg Tyr His Glu Gly Tyr Asp His Ser Tyr
                245                 250                 255

Tyr Phe Val Ser Ser Phe Ile Gly Glu His Ile Ala Tyr His Ala Asn
            260                 265                 270

Lys Leu Asn Met Arg
        275

<210> SEQ ID NO 31
<211> LENGTH: 387
<212> TYPE: PRT
<213> ORGANISM: Escherichia coli (strain K12)

<400> SEQUENCE: 31

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
290                 295                 300

Leu Gln Tyr Ala Glu Arg Val Trp Asn Ile Thr Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 32
<211> LENGTH: 288
<212> TYPE: PRT
<213> ORGANISM: Escherichia coli (strain K12)

<400> SEQUENCE: 32

Met Ala Ala Lys Ile Ile Asp Gly Lys Thr Ile Ala Gln Gln Val Arg
1               5                   10                  15

Ser Glu Val Ala Gln Lys Val Gln Ala Arg Ile Ala Ala Gly Leu Arg
                20                  25                  30

Ala Pro Gly Leu Ala Val Val Leu Val Gly Ser Asn Pro Ala Ser Gln
            35                  40                  45

Ile Tyr Val Ala Ser Lys Arg Lys Ala Cys Glu Glu Val Gly Phe Val
        50                  55                  60

Ser Arg Ser Tyr Asp Leu Pro Glu Thr Thr Ser Glu Ala Glu Leu Leu
65                  70                  75                  80

Glu Leu Ile Asp Thr Leu Asn Ala Asp Asn Thr Ile Asp Gly Ile Leu
            85                  90                  95

Val Gln Leu Pro Leu Pro Ala Gly Ile Asp Asn Val Lys Val Leu Glu
            100                 105                 110

Arg Ile His Pro Asp Lys Asp Val Asp Gly Phe His Pro Tyr Asn Val
            115                 120                 125

Gly Arg Leu Cys Gln Arg Ala Pro Arg Leu Arg Pro Cys Thr Pro Arg
130                 135                 140

Gly Ile Val Thr Leu Leu Glu Arg Tyr Asn Ile Asp Thr Phe Gly Leu
145                 150                 155                 160

Asn Ala Val Val Ile Gly Ala Ser Asn Ile Val Gly Arg Pro Met Ser
            165                 170                 175

Met Glu Leu Leu Leu Ala Gly Cys Thr Thr Thr Val Thr His Arg Phe
            180                 185                 190

Thr Lys Asn Leu Arg His His Val Glu Asn Ala Asp Leu Leu Ile Val
            195                 200                 205

Ala Val Gly Lys Pro Gly Phe Ile Pro Gly Asp Trp Ile Lys Glu Gly
210                 215                 220

Ala Ile Val Ile Asp Val Gly Ile Asn Arg Leu Glu Asn Gly Lys Val
225                 230                 235                 240

Val Gly Asp Val Val Phe Glu Asp Ala Ala Lys Arg Ala Ser Tyr Ile
            245                 250                 255

Thr Pro Val Pro Gly Gly Val Gly Pro Met Thr Val Ala Thr Leu Ile
            260                 265                 270

Glu Asn Thr Leu Gln Ala Cys Val Glu Tyr His Asp Pro Gln Asp Glu
            275                 280                 285

<210> SEQ ID NO 33
<211> LENGTH: 288
<212> TYPE: PRT
<213> ORGANISM: Escherichia fergusonii (strain ATCC
      35469/DSM 13698/CDC 0568-73)

<400> SEQUENCE: 33

Met Ala Ala Lys Ile Ile Asp Gly Lys Thr Ile Ala Gln Gln Val Arg
1               5                   10                  15

Ser Glu Val Ala Gln Lys Val Gln Ala Arg Val Ala Ala Gly Leu Arg
            20                  25                  30

Ala Pro Gly Leu Ala Val Val Leu Val Gly Ser Asn Pro Ala Ser Gln
            35                  40                  45

Ile Tyr Val Ala Ser Lys Arg Lys Ala Cys Glu Glu Val Gly Phe Val
        50                  55                  60

Ser Arg Ser Tyr Asp Leu Pro Glu Thr Thr Ser Glu Ala Glu Leu Leu
65                  70                  75                  80

Glu Leu Ile Asp Val Leu Asn Ala Asp Asn Thr Ile Asp Gly Ile Leu
            85                  90                  95

Val Gln Leu Pro Leu Pro Ala Gly Ile Asp Asn Val Lys Val Leu Glu
            100                 105                 110

Arg Ile His Pro Asp Lys Asp Val Asp Gly Phe His Pro Tyr Asn Val
            115                 120                 125

Gly Arg Leu Cys Gln Arg Ala Pro Arg Leu Arg Pro Cys Thr Pro Arg
130                 135                 140

```
Gly Ile Val Thr Leu Leu Glu Arg Tyr Asn Ile Asp Thr Phe Gly Leu
145                 150                 155                 160

Asn Ala Val Val Ile Gly Ala Ser Asn Ile Val Gly Arg Pro Met Ser
                165                 170                 175

Met Glu Leu Leu Leu Ala Gly Cys Thr Thr Thr Val Thr His Arg Phe
            180                 185                 190

Thr Lys Asn Leu Arg His His Val Glu Asn Ala Asp Leu Leu Ile Val
        195                 200                 205

Ala Val Gly Lys Pro Gly Phe Ile Pro Gly Asp Trp Ile Lys Glu Gly
    210                 215                 220

Ala Ile Val Ile Asp Val Gly Ile Asn Arg Leu Glu Asn Gly Lys Val
225                 230                 235                 240

Val Gly Asp Val Val Phe Glu Asp Ala Ala Lys Arg Ala Ser Tyr Ile
                245                 250                 255

Thr Pro Val Pro Gly Gly Val Gly Pro Met Thr Val Ala Thr Leu Ile
            260                 265                 270

Glu Asn Thr Leu Gln Ala Cys Val Glu Tyr His Asp Pro Gln Asp Glu
        275                 280                 285
```

<210> SEQ ID NO 34
<211> LENGTH: 288
<212> TYPE: PRT
<213> ORGANISM: Shigella dysenteriae serotype 1 (strain Sd197)

<400> SEQUENCE: 34

Met Ala Ala Lys Ile Ile Asp Gly Lys Thr Ile Ala Gln Gln Val Arg
1 5 10 15

Ser Glu Val Ala Gln Lys Val Gln Ala Arg Ile Ala Ala Gly Leu Arg
20 25 30

Ala Pro Gly Leu Ala Val Val Leu Val Gly Ser Asn Pro Ala Ser Gln
35 40 45

Ile Tyr Val Ala Ser Lys Arg Lys Ala Cys Glu Glu Val Gly Phe Val
50 55 60

Ser Arg Ser Tyr Asp Leu Pro Glu Thr Thr Ser Glu Ala Glu Leu Leu
65 70 75 80

Glu Leu Ile Asp Ala Leu Asn Ala Asp Asn Thr Ile Asp Gly Ile Leu
85 90 95

Val Gln Leu Pro Leu Pro Ala Gly Ile Asp Asn Val Lys Val Leu Glu
100 105 110

Arg Ile His Pro Asp Lys Asp Val Asp Gly Phe His Pro Tyr Asn Val
115 120 125

Gly Arg Leu Cys Gln Arg Ala Pro Arg Leu Arg Pro Cys Thr Pro Arg
130 135 140

Gly Ile Val Thr Leu Leu Glu Arg Tyr Asn Ile Asp Thr Phe Gly Leu
145 150 155 160

Asn Ala Val Val Ile Gly Ala Ser Asn Ile Val Gly Arg Pro Met Ser
165 170 175

Met Glu Leu Leu Leu Ala Gly Cys Thr Thr Thr Val Thr His Arg Phe
180 185 190

Thr Lys Asn Leu Arg His His Val Glu Asn Ala Asp Leu Leu Ile Val
195 200 205

Ala Val Gly Lys Pro Gly Phe Ile Pro Gly Asp Trp Ile Lys Glu Gly
210 215 220

Ala Ile Val Ile Asp Val Gly Ile Asn Arg Leu Glu Asn Gly Lys Val
225 230 235 240

```
Val Gly Asp Val Val Phe Glu Asp Ala Ala Lys His Ala Ser Tyr Ile
                245                 250                 255

Thr Pro Val Pro Gly Val Gly Pro Met Thr Val Ala Thr Leu Ile
            260                 265                 270

Glu Asn Thr Leu Gln Ala Cys Val Glu Tyr His Asp Pro Gln Asp Glu
            275                 280                 285

<210> SEQ ID NO 35
<211> LENGTH: 760
<212> TYPE: PRT
<213> ORGANISM: Escherichia coli (strain K12)

<400> SEQUENCE: 35

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
                20                  25                  30

Asn Tyr Thr Pro Tyr Glu Gly Asp Glu Ser Phe Leu Ala Gly Ala Thr
            35                  40                  45

Glu Ala Thr Thr Thr Leu Trp Asp Lys Val Met Glu Gly Val Lys Leu
50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
                100                 105                 110

Phe Gly Gly Ile Lys Met Ile Glu Gly Ser Cys Lys Ala Tyr Asn Arg
            115                 120                 125

Glu Leu Asp Pro Met Ile Lys Lys Ile Phe Thr Glu Tyr Arg Lys Thr
130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
            260                 265                 270

Ala Ala Met Ser Phe Gly Arg Thr Ser Thr Phe Leu Asp Val Tyr Ile
        275                 280                 285

Glu Arg Asp Leu Lys Ala Gly Lys Ile Thr Glu Gln Glu Ala Gln Glu
    290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
```

```
                    325                 330                 335
Glu Ser Ile Gly Gly Met Gly Leu Asp Gly Arg Thr Leu Val Thr Lys
                340                 345                 350
Asn Ser Phe Arg Phe Leu Asn Thr Leu Tyr Thr Met Gly Pro Ser Pro
                355                 360                 365
Glu Pro Asn Met Thr Ile Leu Trp Ser Glu Lys Leu Pro Leu Asn Phe
370                 375                 380
Lys Lys Phe Ala Ala Lys Val Ser Ile Asp Thr Ser Ser Leu Gln Tyr
385                 390                 395                 400
Glu Asn Asp Asp Leu Met Arg Pro Asp Phe Asn Asn Asp Asp Tyr Ala
                405                 410                 415
Ile Ala Cys Cys Val Ser Pro Met Ile Val Gly Lys Gln Met Gln Phe
                420                 425                 430
Phe Gly Ala Arg Ala Asn Leu Ala Lys Thr Met Leu Tyr Ala Ile Asn
                435                 440                 445
Gly Gly Val Asp Glu Lys Leu Lys Met Gln Val Gly Pro Lys Ser Glu
                450                 455                 460
Pro Ile Lys Gly Asp Val Leu Asn Tyr Asp Glu Val Met Glu Arg Met
465                 470                 475                 480
Asp His Phe Met Asp Trp Leu Ala Lys Gln Tyr Ile Thr Ala Leu Asn
                485                 490                 495
Ile Ile His Tyr Met His Asp Lys Tyr Ser Tyr Glu Ala Ser Leu Met
                500                 505                 510
Ala Leu His Asp Arg Asp Val Ile Arg Thr Met Ala Cys Gly Ile Ala
                515                 520                 525
Gly Leu Ser Val Ala Ala Asp Ser Leu Ser Ala Ile Lys Tyr Ala Lys
                530                 535                 540
Val Lys Pro Ile Arg Asp Glu Asp Gly Leu Ala Ile Asp Phe Glu Ile
545                 550                 555                 560
Glu Gly Glu Tyr Pro Gln Phe Gly Asn Asn Asp Pro Arg Val Asp Asp
                565                 570                 575
Leu Ala Val Asp Leu Val Glu Arg Phe Met Lys Lys Ile Gln Lys Leu
                580                 585                 590
His Thr Tyr Arg Asp Ala Ile Pro Thr Gln Ser Val Leu Thr Ile Thr
                595                 600                 605
Ser Asn Val Val Tyr Gly Lys Lys Thr Gly Asn Thr Pro Asp Gly Arg
                610                 615                 620
Arg Ala Gly Ala Pro Phe Gly Pro Gly Ala Asn Pro Met His Gly Arg
625                 630                 635                 640
Asp Gln Lys Gly Ala Val Ala Ser Leu Thr Ser Val Ala Lys Leu Pro
                645                 650                 655
Phe Ala Tyr Ala Lys Asp Gly Ile Ser Tyr Thr Phe Ser Ile Val Pro
                660                 665                 670
Asn Ala Leu Gly Lys Asp Asp Glu Val Arg Lys Thr Asn Leu Ala Gly
                675                 680                 685
Leu Met Asp Gly Tyr Phe His His Glu Ala Ser Ile Glu Gly Gly Gln
                690                 695                 700
His Leu Asn Val Asn Val Met Asn Arg Glu Met Leu Leu Asp Ala Met
705                 710                 715                 720
Glu Asn Pro Glu Lys Tyr Pro Gln Leu Thr Ile Arg Val Ser Gly Tyr
                725                 730                 735
Ala Val Arg Phe Asn Ser Leu Thr Lys Glu Gln Gln Gln Asp Val Ile
                740                 745                 750
```

Thr Arg Thr Phe Thr Gln Ser Met
        755                 760

<210> SEQ ID NO 36
<211> LENGTH: 764
<212> TYPE: PRT
<213> ORGANISM: Escherichia coli (strain K12)

<400> SEQUENCE: 36

Met Lys Val Asp Ile Asp Thr Ser Asp Lys Leu Tyr Ala Asp Ala Trp
1               5                   10                  15

Leu Gly Phe Lys Gly Thr Asp Trp Lys Asn Glu Ile Asn Val Arg Asp
            20                  25                  30

Phe Ile Gln His Asn Tyr Thr Pro Tyr Glu Gly Asp Glu Ser Phe Leu
        35                  40                  45

Ala Glu Ala Thr Pro Ala Thr Thr Glu Leu Trp Glu Lys Val Met Glu
    50                  55                  60

Gly Ile Arg Ile Glu Asn Ala Thr His Ala Pro Val Asp Phe Asp Thr
65                  70                  75                  80

Asn Ile Ala Thr Thr Ile Thr Ala His Asp Ala Gly Tyr Ile Asn Gln
                85                  90                  95

Pro Leu Glu Lys Ile Val Gly Leu Gln Thr Asp Ala Pro Leu Lys Arg
            100                 105                 110

Ala Leu His Pro Phe Gly Gly Ile Asn Met Ile Lys Ser Ser Phe His
        115                 120                 125

Ala Tyr Gly Arg Glu Met Asp Ser Glu Phe Glu Tyr Leu Phe Thr Asp
    130                 135                 140

Leu Arg Lys Thr His Asn Gln Gly Val Phe Asp Val Tyr Ser Pro Asp
145                 150                 155                 160

Met Leu Arg Cys Arg Lys Ser Gly Val Leu Thr Gly Leu Pro Asp Gly
                165                 170                 175

Tyr Gly Arg Gly Arg Ile Ile Gly Asp Tyr Arg Arg Val Ala Leu Tyr
            180                 185                 190

Gly Ile Ser Tyr Leu Val Arg Glu Arg Glu Leu Gln Phe Ala Asp Leu
        195                 200                 205

Gln Ser Arg Leu Glu Lys Gly Glu Asp Leu Glu Ala Thr Ile Arg Leu
    210                 215                 220

Arg Glu Glu Leu Ala Glu His Arg His Ala Leu Leu Gln Ile Gln Glu
225                 230                 235                 240

Met Ala Ala Lys Tyr Gly Phe Asp Ile Ser Arg Pro Ala Gln Asn Ala
                245                 250                 255

Gln Glu Ala Val Gln Trp Leu Tyr Phe Ala Tyr Leu Ala Ala Val Lys
            260                 265                 270

Ser Gln Asn Gly Gly Ala Met Ser Leu Gly Arg Thr Ala Ser Phe Leu
        275                 280                 285

Asp Ile Tyr Ile Glu Arg Asp Phe Lys Ala Gly Val Leu Asn Glu Gln
    290                 295                 300

Gln Ala Gln Glu Leu Ile Asp His Phe Ile Met Lys Ile Arg Met Val
305                 310                 315                 320

Arg Phe Leu Arg Thr Pro Glu Phe Asp Ser Leu Phe Ser Gly Asp Pro
                325                 330                 335

Ile Trp Ala Thr Glu Val Ile Gly Gly Met Gly Leu Asp Gly Arg Thr
            340                 345                 350

Leu Val Thr Lys Asn Ser Phe Arg Tyr Leu His Thr Leu His Thr Met

```
            355                 360                 365
Gly Pro Ala Pro Glu Pro Asn Leu Thr Ile Leu Trp Ser Glu Leu
370                 375                 380
Pro Ile Ala Phe Lys Lys Tyr Ala Ala Gln Val Ser Ile Val Thr Ser
385                 390                 395                 400
Ser Leu Gln Tyr Glu Asn Asp Asp Leu Met Arg Thr Asp Phe Asn Ser
                405                 410                 415
Asp Asp Tyr Ala Ile Ala Cys Cys Val Ser Pro Met Val Ile Gly Lys
            420                 425                 430
Gln Met Gln Phe Phe Gly Ala Arg Ala Asn Leu Ala Lys Thr Leu Leu
        435                 440                 445
Tyr Ala Ile Asn Gly Gly Val Asp Glu Lys Leu Lys Ile Gln Val Gly
    450                 455                 460
Pro Lys Thr Ala Pro Leu Met Asp Asp Val Leu Asp Tyr Asp Lys Val
465                 470                 475                 480
Met Asp Ser Leu Asp His Phe Met Asp Trp Leu Ala Val Gln Tyr Ile
                485                 490                 495
Ser Ala Leu Asn Ile Ile His Tyr Met His Asp Lys Tyr Ser Tyr Glu
            500                 505                 510
Ala Ser Leu Met Ala Leu His Asp Arg Asp Val Tyr Arg Thr Met Ala
        515                 520                 525
Cys Gly Ile Ala Gly Leu Ser Val Ala Thr Asp Ser Leu Ser Ala Ile
    530                 535                 540
Lys Tyr Ala Arg Val Lys Pro Ile Arg Asp Glu Asn Gly Leu Ala Val
545                 550                 555                 560
Asp Phe Glu Ile Asp Gly Glu Tyr Pro Gln Tyr Gly Asn Asn Asp Glu
                565                 570                 575
Arg Val Asp Ser Ile Ala Cys Asp Leu Val Glu Arg Phe Met Lys Lys
            580                 585                 590
Ile Lys Ala Leu Pro Thr Tyr Arg Asn Ala Val Pro Thr Gln Ser Ile
        595                 600                 605
Leu Thr Ile Thr Ser Asn Val Val Tyr Gly Gln Lys Thr Gly Asn Thr
    610                 615                 620
Pro Asp Gly Arg Arg Ala Gly Thr Pro Phe Ala Pro Gly Ala Asn Pro
625                 630                 635                 640
Met His Gly Arg Asp Arg Lys Gly Ala Val Ala Ser Leu Thr Ser Val
                645                 650                 655
Ala Lys Leu Pro Phe Thr Tyr Ala Lys Asp Gly Ile Ser Tyr Thr Phe
            660                 665                 670
Ser Ile Val Pro Ala Ala Leu Gly Lys Glu Asp Pro Val Arg Lys Thr
        675                 680                 685
Asn Leu Val Gly Leu Leu Asp Gly Tyr Phe His His Glu Ala Asp Val
    690                 695                 700
Glu Gly Gly Gln His Leu Asn Val Asn Val Met Asn Arg Glu Met Leu
705                 710                 715                 720
Leu Asp Ala Ile Glu His Pro Glu Lys Tyr Pro Asn Leu Thr Ile Arg
                725                 730                 735
Val Ser Gly Tyr Ala Val Arg Phe Asn Ala Leu Thr Arg Glu Gln Gln
            740                 745                 750
Gln Asp Val Ile Ser Arg Thr Phe Thr Gln Ala Leu
        755                 760

<210> SEQ ID NO 37
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 37

His His His His His His
1               5
```